United States Patent
Xu et al.

(10) Patent No.: US 10,183,010 B2
(45) Date of Patent: Jan. 22, 2019

(54) 2-OXO-1,2-DIHYDROBENZO[CD]INDOLE COMPOUND AND USE THEREOF

(71) Applicant: Guangzhou Institutes of Biomedicine and Health, Chinese Academy of Sciences, Guangzhou (CN)

(72) Inventors: Yong Xu, Guangzhou (CN); Xiaoqian Xue, Guangzhou (CN); Yan Zhang, Guangzhou (CN); Ming Song, Guangzhou (CN)

(73) Assignee: GUANGZHOU INSTITUTES OF BIOMEDICINE AND HEALTH, CHINESE ACADEMY OF SCIENCES, Guangzhou (CN)

( * ) Notice: Subject to any disclaimer, the term of this patent is extended or adjusted under 35 U.S.C. 154(b) by 0 days.

(21) Appl. No.: 15/546,251

(22) PCT Filed: Jan. 27, 2016

(86) PCT No.: PCT/CN2016/072266
§ 371 (c)(1),
(2) Date: Jul. 25, 2017

(87) PCT Pub. No.: WO2016/119690
PCT Pub. Date: Aug. 4, 2016

(65) Prior Publication Data
US 2018/0008574 A1 Jan. 11, 2018

(30) Foreign Application Priority Data
Jan. 28, 2015 (CN) .......................... 2015 1 0043387

(51) Int. Cl.
| C07D 209/92 | (2006.01) |
| A61K 31/403 | (2006.01) |
| C07D 403/12 | (2006.01) |
| A61K 31/422 | (2006.01) |
| A61K 31/454 | (2006.01) |
| A61K 31/5377 | (2006.01) |
| C07D 401/12 | (2006.01) |
| C07D 405/12 | (2006.01) |
| C07D 409/12 | (2006.01) |
| C07D 413/12 | (2006.01) |
| A61K 45/06 | (2006.01) |

(52) U.S. Cl.
CPC .......... *A61K 31/403* (2013.01); *A61K 31/422* (2013.01); *A61K 31/454* (2013.01); *A61K 31/5377* (2013.01); *A61K 45/06* (2013.01); *C07D 209/92* (2013.01); *C07D 401/12* (2013.01); *C07D 403/12* (2013.01); *C07D 405/12* (2013.01); *C07D 409/12* (2013.01); *C07D 413/12* (2013.01)

(58) Field of Classification Search
CPC ........................... C07D 209/92; A61K 31/403
See application file for complete search history.

(56) References Cited

U.S. PATENT DOCUMENTS

| 4,728,663 A | * | 3/1988 | Tomcufcik | ........... | C07D 231/12 |
| | | | | | 514/394 |
| 5,081,131 A | * | 1/1992 | Tomcufcik | ........... | C07D 231/12 |
| | | | | | 514/333 |
| 7,615,563 B2 | | 11/2009 | Gonzalez, III et al. | | |
| 2007/0105835 A1 | | 5/2007 | Kazantsev | | |

FOREIGN PATENT DOCUMENTS

| CN | 1062904 | 7/1992 |
| CN | 104530014 | 4/2015 |
| JP | 2003-137866 | 5/2003 |
| WO | 2007/0050795 | 5/2007 |
| WO | 2009/016081 | 2/2009 |
| WO | 2014/173241 | 10/2014 |

OTHER PUBLICATIONS

Shibata et al (2003): STN International, HCAPLUS database (Columbus, Ohio), Accession No. 2003: 366795.*
Gonzalez et al (2006): STN International, HCAPLUS database (Columbus, Ohio), Accession No. 2006: 103871.*
Kazantsev et al (2007): STN International, HCAPLUS database (Columbus, Ohio), Accession No. 2007: 507490.*
Xue et al, "Discovery of Benzo[cd]indo1-2(1H)-ones as Potent and Specific BET Bromodomain Inhibitors: Structure-Based Virtual Screening, Optimization, and Biological Evaluation", Journal of Medicinal Chemistry, vol. 59, Jan. 5, 2016, pp. 1565-1579.
Zhang et al., "Discovery of 2-oxo-1,2-dihydrobenzo[cd]indole-6-sulfonamide derivatives as new RORγ inhibitors using virtual screening, synthesis and biological evaluation", European Journal of Medicinal Chemistry, vol. 78, Mar. 22, 2014, pp. 431-441.
Begley et al., "Fragment-based discovery of novel thymidylate synthase leads by NMR screening and group epitope mapping", Chem Biol Drug Des, vol. 76, May 17, 2010, pp. 218-233.

* cited by examiner

*Primary Examiner* — Golam M Shameem
(74) *Attorney, Agent, or Firm* — Fay Kaplun & Marcin, LLP

(57) ABSTRACT

The present invention relates to the technical field of medicinal chemistry, and in particular discloses a 2-oxo-1,2-dihydrobenzo[cd]indole compound and use thereof. The compound and pharmaceutically acceptable salt, isomer, racemate, prodrug, co-crystallized complex, hydrate, and solvate thereof can effectively inhibit the BET bromodomain receptor, and can be used for preparing a medicine for treating cancers, cell proliferative disorders, inflammatory diseases, and autoimmune disorders, sepsis, and viral infections.

5 Claims, No Drawings

2-OXO-1,2-DIHYDROBENZO[CD]INDOLE COMPOUND AND USE THEREOF

TECHNICAL FIELD

The present invention relates to the technical field of chemical medicines, and specifically to a 2-oxo-1,2-dihydrobenzo[cd]indole compound and use thereof.

BACKGROUND ART

The bromodomain (BRD) family of proteins recognizes and binds to the acetylated lysine acting as a reader of lysine acetylation state. These "epigenetic readers" bind to acetyllysine residues on the tails of histones H3 and H4, and regulate chromatin structure and gene expression. There is increasing evidence of their role in human disease, and recently a number of small-molecule nihibitors have been reported. There is increasing evidence for the roles of BRDs in disease including inflammation, neurological indications, viral infection, cancers, and autoimmune disorder.

An analysis of the human proteome has revealed that there are eight distinct BRD families, representing 61 different BRDs from 46 separate proteins, although others may still be undiscovered. The BET family of BRDs is a subset of this larger bromodomain family and is made up of four members: BRD2, BRD3, BRD4, and BRDT in humans. BRD2 and BRD3 are reported to associate with histones along activity transcribed genes and may be involved in facilitating transcriptional elongation, while BRD4 appears to be involved in the recruitment of the P-TEFb complex to inducible genes, resulting in phosphorylation of RNApolymerase and increased transcription output. Chromosomal translocation of BRD3 and BRD4 to the nuclear protein in testis (NUT) locus generates BRD3-NUT or BRD4-NUT fusion protein that results in c-Myc overexpression and NUT midline carcinoma (NMC), an aggressive squamous cell malignancy unresponsive to conventional chemotherapeutics. BRDT is uniquely expressed in the testes and ovary.

Recently, a number of small-molecule compounds with potent inhibitory activity against BET family proteins have been reported. The first potent BET inhibitor was the diazepine JQ1 by nuclear magnetic resonance technology, subsequently, more molecues were reported by epigenetic screening and targeted biochemistry. By these potent inhibitors, more knowledge about the relationship of BET proteins and diseases was disclosed. Rapid progress in the development of bromodomain ligands has stimulated extensive interest and has led to several BET bromodomain inhibitors reaching clinical trials for cancers and inflammations.

CONTENTS OF THE INVENTION

The technical problem to be solved by the present invention is: providing a 2-oxo-1,2-dihydrobenzo[cd]indole compound, which is effective in inhibiting the BET bromodomain receptor and can be used as a therapeutic medicine for cancer, cell proliferation disorders, inflammatory diseases and autoimmune diseases, sepsis, viral infections.

The above-mentioned problems are solved by the present invention according to the following technical solutions:

A 2-oxo-1,2-dihydrobenzo[cd]indole compound or pharmaceutically acceptable salts, isomers, racemates, prodrugs, cocrystalline complexes, hydrates, or solvates thereof, having a structure represented by formula I, II, III or IV:

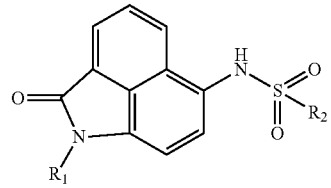
(I)

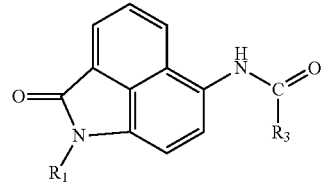
(II)

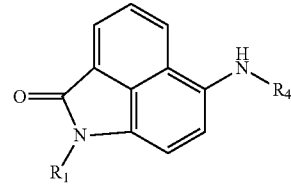
(III)

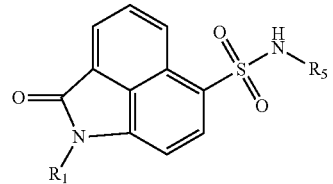
(IV)

In formula I, $R_1$ is selected from H or $C_1$-$C_4$ linear or branched alkyl; $R_2$ is selected from $C_1$-$C_7$ alkyl, $C_1$-$C_4$ alkylene-$R_6$ or $C_0$-$C_4$ alkylene-$R_7$-cyclic ring; wherein $R_6$ is selected from —$OR_8$, —$COR_8$, —$CONHR_8$, —$COOR_8$, —$S(O)_mR_8$, —$S(O)_mR_8$, —$NHCOOR_8$, —$NHCOR_8$ or —$NH_2$, wherein m is 0 or 2, and $R_8$ is selected from hydrogen or $C_1$-$C_3$ alkyl; wherein $R_7$ is selected from —$COR_9$, —$COOR_9$, —$OR_9$ or unselected, wherein $R_9$ is selected from $C_1$-$C_3$ alkylene; wherein cyclic ring is selected from $C_3$-$C_{10}$ cycloalkyl, phenyl, or heterocyclic group;

In formula II, $R_1$ is selected from H or $C_1$-$C_4$ linear or branched alkyl; $R_3$ is selected from $C_1$-$C_7$ alkyl, $C_1$-$C_4$ alkylene-$R_6$ or $C_0$-$C_4$ alkylene-$R_7$-cyclic ring; wherein $R_6$ is selected from —$OR_8$, —$COR_8$, —$CONHR_8$, —$COOR_8$, —$S(O)_mR_8$ or —$S(O)_mR_8$, wherein m is 0 or 2, and $R_8$ is selected from hydrogen, $C_1$-$C_3$ alkyl; wherein $R_7$ is selected from —$COR_9$, —$COOR_9$, —$OR_9$ or unselected, wherein $R_9$ is selected from $C_1$-$C_3$ alkylene; wherein cyclic ring is selected from $C_3$-$C_{10}$ cycloalkyl, phenyl, or heterocyclic group; In formula III, $R_1$ is selected from H or $C_1$-$C_4$ linear or branched alkyl; $R_4$ is selected from $C_1$-$C_7$ alkyl, $C_1$-$C_4$ alkylene-$R_6$ or $C_0$-$C_4$ alkylene-$R_7$-cyclic ring; wherein $R_6$ is selected from —$OR_8$, —$COR_8$, —$CONHR_8$, —$COOR_8$, —$S(O)_mR_8$, —$S(O)_mR_8$, —$NHCOOR_8$ or —$NHCOR_8$, wherein m is 0 or 2, and $R_8$ is selected from hydrogen or $C_1$-$C_3$ alkyl; wherein $R_7$ is selected from —$COR_9$, —$COOR_9$, —$OR_9$ or unselected, wherein $R_9$ is selected from $C_1$-$C_3$ alkylene; wherein cyclic ring is selected from $C_3$-$C_{10}$ cycloalkyl, phenyl, or heterocyclic group;

In formula IV, $R_1$ is selected from H or $C_1$-$C_4$ linear or branched alkyl; $R_5$ is selected from $C_1$-$C_7$ alkyl, $C_1$-$C_4$ alkylene-$R_6$ or $C_0$-$C_4$ alkylene-$R_7$-cyclic ring; wherein $R_6$ is selected from —OR$_8$, —COR$_8$, —CONHR$_8$, —COOR$_8$, —S(O)$_m$R$_8$, —S(O)$_m$R$_8$, —NHCOOR$_8$ or —NHCOR$_8$, wherein m is 0 or 2, and R$_8$ is selected from hydrogen, C$_1$-C$_3$ alkyl; wherein R$_7$ is selected from —COR$_9$, —COOR$_9$, —OR$_9$ or unselected, wherein R$_9$ is selected from C$_1$-C$_3$ alkylene; wherein cyclic ring is selected from C$_3$-C$_{10}$ cycloalkyl, phenyl, or heterocyclic group;

Preferably, the R$_1$ in formula I, II, III and IV is selected from H, methyl, ethyl, propyl, isopropyl or tert-butyl.

Preferably, in formula I, the cyclic ring in the C$_0$-C$_4$ alkylene-R$_7$-cyclic ring is selected from cyclopropane, cyclobutane, cyclopentane, cyclohexane, cycloheptane, phenyl, naphthyl, azetidine, oxetane, azacyclopentane, oxacyclopentane, azacyclohexane, oxacyclohexane, azacyclohexyl, imidazol-2-one ring, imidazolyl, furyl, thienyl, oxazolyl, isoxazolyl, pyrimidinyl, pyrrolyl, piperazinyl, tetrahydropyrrolyl, piperidinyl, morpholinyl, 1,3-dioxolanyl or benzo[d]thiazolyl, and these cycloalkyls are substituted by 0, 1, 2 or 3 group(s) selected from halogen, methyl, ethyl, propyl, isopropyl, tert-butyl, trifluoromethyl, cyano, nitro, amino, amide, —COOR$_{10}$, —COR$_{10}$, —OR$_{10}$, —NHCOR$_{10}$, —NHCOOR$_{10}$, —C$_6$H$_5$R$_{11}$, morpholinyl, piperidinyl, tetrahydrofuranyl or pyridyl, wherein R$_{10}$ is selected from hydrogen, C$_1$-C$_4$ alkyl or phenyl, and R$_{11}$ is selected from C$_1$-C$_4$ alkyl, halogen, acetyl, methoxy or ethoxy;

In formula II, the cyclic ring in the C$_0$-C$_4$ alkylene-R$_7$-cyclic ring is selected from cyclopropane, cyclobutane, cyclopentane, cyclohexane, cycloheptane, phenyl, azetidine, oxetane, azacyclopentane, oxacyclopentane, azacyclohexane, oxacyclohexane, azacyclohexyl, furyl, thienyl, oxazolyl, isoxazolyl, pyrimidinyl, pyrrolyl, tetrahydropyrrolyl, piperidinyl, morpholinyl, 1,3-dioxolanyl or benzo[d]thiazolyl, and these cycloalkyls are substituted by 0, 1, 2 or 3 group(s) selected from halogen, methyl, ethyl, propyl, isopropyl, tert-butyl, trifluoromethyl, cyano, carboxyl, nitro, amino, —CONH$_2$, —COOR$_{10}$, —COR$_{10}$, —OR$_{10}$, —NHCOR$_{10}$, —NHCOOR$_{10}$, —C$_6$H$_5$R$_{11}$, morpholinyl, piperidinyl, tetrahydrofuranyl or pyridyl, wherein R$_{10}$ is selected from hydrogen, C$_1$-C$_4$ alkyl or phenyl, and R$_{11}$ is selected from C$_1$-C$_4$ alkyl, halogen, acetyl, methoxy or ethoxy;

In formula III, the cyclic ring in the C$_0$-C$_4$ alkylene-R$_7$-cyclic ring is selected from cyclopropane, cyclobutane, cyclopentane, cyclohexane, cycloheptane, phenyl, azetidine, oxetane, azacyclopentane, oxacyclopentane, azacyclohexane, oxacyclohexane, azacyclohexyl, imidazol-2-one ring, imidazolyl, furyl, thienyl, oxazolyl, isoxazolyl, pyrimidinyl, pyrrolyl, piperazinyl, tetrahydropyrrolyl, piperidinyl, morpholinyl, 1,3-dioxolanyl or benzo[d]thiazolyl, and these cycloalkyls are substituted by 0, 1, 2 or 3 group(s) selected from halogen, methyl, ethyl, propyl, isopropyl, tert-butyl, trifluoromethyl, cyano, nitro, amino, —CONH$_2$, —COOR$_{10}$, —COR$_{10}$, —OR$_{10}$, —NHCOR$_{10}$, —NHCOOR$_{10}$, —C$_6$H$_5$R$_{11}$, morpholinyl, piperidinyl, tetrahydrofuranyl or pyridyl, wherein R$_{10}$ is selected from hydrogen, C$_1$-C$_4$ alkyl and phenyl, and R$_{11}$ is selected from C$_1$-C$_4$ alkyl, halogen, acetyl, methoxy or ethoxy;

In formula IV, the cyclic ring in the C$_0$-C$_4$ alkylene-R$_7$-cyclic ring is selected from cyclopropane, cyclobutane, cyclopentane, cyclohexane, cycloheptane, phenyl, azetidine, oxetane, azacyclopentane, oxacyclopentane, azacyclohexane, oxacyclohexane, azacyclohexyl, imidazol-2-one ring, furyl, thienyl, oxazolyl, isoxazolyl, pyrrolyl, piperazinyl, tetrahydropyrrolyl, piperidinyl, morpholinyl, 1,3-dioxolanyl or 1H-indolyl, and these heterocyclic rings can be substituted by 0, 1, 2 or 3 group(s) selected from halogen, methyl, ethyl, propyl, isopropyl, tert-butyl, trifluoromethyl, nitro, amino, amide, —COOR$_9$, —COR$_9$, —OR$_9$, —NHCOR$_9$, —NHCOOR$_9$, —C$_6$H$_5$R$_{10}$, morpholinyl, piperidinyl, tetrahydrofuranyl and pyridyl, wherein R$_9$ is selected from C$_1$-C$_4$ alkyl and phenyl, and R$_{10}$ is selected from hydrogen, C$_1$-C$_4$ alkyl, halogen, acetyl, methoxy or ethoxy.

More preferably, in formula I, wherein C$_1$-C$_7$ alkyl is selected from methyl, ethyl, propyl, isopropyl, n-butyl, tert-butyl, n-pentyl, n-hexyl or n-heptyl; for C$_1$-C$_4$ alkylene-R$_6$, R$_6$ is selected from —OR$_8$, —COR$_8$, —CONHR$_8$, —COOR$_8$, —S(O)$_m$R$_8$, —S(O)$_m$R$_8$, —NHCOOR$_8$ and —NHCOR$_8$, wherein m is 0 or 2, and R$_8$ is selected from hydrogen, methyl, ethyl, propyl, tert-butyl; for C$_0$-C$_4$ alkylene-R$_7$-cyclic ring, R$_7$ is selected from —COR$_9$, —COOR$_9$, —OR$_9$ or unselected, wherein R$_9$ is selected from C$_1$-C$_3$ alkylene, and the cyclic ring is selected from cyclopropane, cyclobutane, cyclopentane, cyclohexane, cycloheptane, phenyl, azetidine, oxetane, azacyclopentane, oxacyclopentane, azacyclohexane, oxacyclohexane, azacyclohexyl, imidazol-2-one ring or 1,3-dioxolanyl, and these cycloalkyls are substituted by 0, 1, 2 or 3 group(s) selected from halogen, methyl, ethyl, propyl, isopropyl, tert-butyl, trifluoromethyl, cyano, nitro, amino, amide, —COOR$_{10}$, —COR$_{10}$, —OR$_{10}$, —NHCOR$_{10}$, —NHCOOR$_{10}$, —C$_6$H$_5$R$_{11}$, morpholinyl, piperidinyl, tetrahydrofuranyl or pyridyl, wherein R$_{10}$ is selected from hydrogen, C$_1$-C$_4$ alkyl and phenyl, and R$_{11}$ is selected from methyl, ethyl, propyl, fluorine, chlorine, bromine, acetyl, methoxy, ethoxy.

More preferably, in formula II, wherein C$_1$-C$_7$ alkyl is selected from methyl, ethyl, propyl, isopropyl, n-butyl, tert-butyl, n-pentyl, n-hexyl or n-heptyl; for C$_1$-C$_4$ alkylene-R$_6$, R$_6$ is selected from —OR$_8$, —COR$_8$, —CONHR$_8$, —COOR$_8$, —S(O)$_m$R$_8$, —S(O)$_m$R$_8$, —NHCOOR$_8$ or —NHCOR$_8$, wherein m is 0 or 2, and R$_8$ is selected from hydrogen, methyl, ethyl, propyl, tert-butyl; for C$_0$-C$_4$ alkylene-R$_7$-cyclic ring, R$_7$ is selected from —COR$_9$, —COOR$_9$, —OR$_9$ or unselected, wherein R$_9$ is selected from C$_1$-C$_3$ alkylene, and the cyclic ring is selected from cyclopropane, cyclobutane, cyclopentane, cyclohexane, cycloheptane, phenyl, azetidine, oxetane, azacyclopentane, oxacyclopentane, azacyclohexane, oxacyclohexane, azacyclohexyl, furyl, thienyl, oxazolyl, isoxazolyl, pyrimidinyl, pyrrolyl, tetrahydropyrrolyl, piperidinyl, morpholinyl, 1,3-dioxolanyl or benzo[d]thiazolyl, and these cycloalkyls are substituted by 0, 1, 2 or 3 group(s) selected from halogen, methyl, ethyl, propyl, isopropyl, tert-butyl, trifluoromethyl, cyano, nitro, amino, amide, —COOR$_{10}$, —COR$_{10}$, —OR$_{10}$, —NHCOR$_{10}$, —NHCOOR$_{10}$, —C$_6$H$_5$R$_{11}$, morpholinyl, piperidinyl, tetrahydrofuranyl and pyridyl, wherein R$_{10}$ is selected from hydrogen, C$_1$-C$_4$ alkyl and phenyl, and R$_{11}$ is selected from methyl, ethyl, propyl, fluorine, chlorine, bromine, acetyl, methoxy or ethoxy.

More preferably, in formula III, wherein C$_1$-C$_7$ alkyl is selected from methyl, ethyl, propyl, isopropyl, n-butyl, tert-butyl, n-pentyl, n-hexyl, n-heptyl; for C$_1$-C$_4$ alkylene-R$_6$, R$_6$ is selected from —OR$_8$, —COR$_8$, —CONHR$_8$, —COOR$_8$, —S(O)$_m$R$_8$, —NHCOOR$_8$ or —NHCOR$_8$, wherein m is 0 or 2, and R$_8$ is selected from hydrogen, methyl, ethyl, propyl or tert-butyl; for C$_0$-C$_4$ alkylene-R$_7$-cyclic ring, R$_7$ is selected from —COR$_9$, —COOR$_9$, —OR$_9$ or unselected, wherein R$_9$ is selected from C$_1$-C$_3$ alkylene, and the cyclic ring is selected from cyclopropane, cyclobutane, cyclopentane, cyclohexane, cycloheptane, phenyl, azetidine, oxetane, azacyclopentane, oxacyclopentane, azacyclohexane, oxacyclohexane, azacyclohexyl, imidazol-2-one ring, imidazolyl, furyl, thienyl, oxazolyl, isoxazolyl, pyrimidinyl, pyrrolyl, piperazinyl, tetrahydropyrrolyl, piperidinyl, morpholinyl, 1,3-dioxolanyl or benzo[d]thiazolyl, and these cycloalkyls are substituted by 0, 1, 2 or 3 group(s) selected from halogen, methyl, ethyl, propyl, isopropyl, tert-butyl, trifluoromethyl, cyano, nitro, amino, amide, —COOR$_{10}$, —COR$_{10}$, —OR$_{10}$, —NHCOR$_{10}$, —NHCOOR$_{10}$, —C$_6$H$_5$R$_{11}$, morpholinyl, piperidinyl, tetrahydrofuranyl and pyridyl, wherein R$_{10}$ is selected from hydrogen, C$_1$-C$_4$ alkyl and phenyl, and R$_{11}$ is selected from methyl, ethyl, propyl, fluorine, chlorine, bromine, acetyl, methoxy or ethoxy.

More preferably, in formula IV, wherein C$_1$-C$_7$ alkyl is selected from methyl, ethyl, propyl, isopropyl, n-butyl, tert-butyl, n-pentyl, n-hexyl or n-heptyl; for C$_1$-C$_4$ alkylene-R$_6$, R$_6$ is selected from —OR$_8$, —COR$_8$, —CONHR$_8$, —COOR$_8$, —S(O)$_m$R$_8$ or —NHCOOR$_8$, —NHCOR$_8$, wherein m is 0 or 2, and R$_8$ is selected from hydrogen, methyl, ethyl, propyl, tert-butyl; for C$_0$-C$_4$ alkylene-R$_7$-cyclic ring, R$_7$ is selected from —COR$_9$, —COOR$_9$, —OR$_9$ or unselected, wherein R$_9$ is selected from C$_1$-C$_3$ alkylene, and the cyclic ring is selected from cyclopropane, cyclobutane, cyclopentane, cyclohexane, cycloheptane, phenyl, azetidine, oxetane, azacyclopentane, oxacyclopentane, azacyclohexane, oxacyclohexane, azacyclohexyl, imidazol-2-one ring, furyl, thienyl, oxazolyl, isoxazolyl, pyrrolyl, piperazinyl, tetrahydropyrrolyl, piperidinyl, morpholinyl, 1,3-dioxolanyl or 1H-indolyl, and these cycloalkyls are substituted by 0, 1, 2 or 3 group(s) selected from halogen, methyl, ethyl, propyl, isopropyl, tert-butyl, trifluoromethyl, cyano, nitro, amino, amide, —COOR$_{10}$, —COR$_{10}$, —OR$_{10}$, —NHCOR$_{10}$, —NHCOOR$_{10}$, —C$_6$H$_5$R$_{11}$, morpholinyl, piperidinyl, tetrahydrofuranyl or pyridyl, wherein R$_{10}$ is selected from hydrogen, C$_1$-C$_4$ alkyl and phenyl, and R$_{11}$ is selected from methyl, ethyl, propyl, fluorine, chlorine, bromine, acetyl, methoxy or ethoxy.

In particular embodiments, the compound of formula I, II, III, IV is selected from the group consisting of:

N-(1-ethyl-2-oxo-1,2-dihydrobenzo[cd]indol-6-yl)butane-1-sulfonamide;
2-chloro-N-(1-ethyl-2-oxo-1,2-dihydrobenzo[cd]indol-6-yl)-4-fluorobenzenesulfonamide;
N-(1-ethyl-2-oxo-1,2-dihydrobenzo[cd]indol-6-yl)thiophene-2-sulfonamide;
5-chloro-N-(1-ethyl-2-oxo-1,2-dihydrobenzo[cd]indol-6-yl)-2-methoxybenzenesulfonamide;
N-(1-ethyl-2-oxo-1,2-dihydrobenzo[cd]indol-6-yl)cyclohexanesulfonamide;
2-(N-(1-ethyl-2-oxo-1,2-dihydrobenzo[cd]indol-6-yl)sulfamoyl)benzoate;
2-(N-(1-ethyl-2-oxo-1,2-dihydrobenzo[cd]indol-6-yl)sulfamoyl)benzoic acid;
N-(1-ethyl-2-oxo-1,2-dihydrobenzo[cd]indol-6-yl)benzenesulfonamide;
N-(1-ethyl-2-oxo-1,2-dihydrobenzo[cd]indol-6-yl)-4-fluorobenzenesulfonamide;
N-(1-ethyl-2-oxo-1,2-dihydrobenzo[cd]indol-6-yl)-3-fluorobenzenesulfonamide;
N-(1-ethyl-2-oxo-1,2-dihydrobenzo[cd]indol-6-yl)ethanesulfonamide;
N-(1-ethyl-2-oxo-1,2-dihydrobenzo[cd]indol-6-yl)-4-methoxybenzenesulfonamide;
4-cyano-N-(1-ethyl-2-oxo-1,2-dihydrobenzo[cd]indol-6-yl)benzenesulfonamide;
N-(1-ethyl-2-oxo-1,2-dihydrobenzo[cd]indol-6-yl)-4-nitrobenzenesulfonamide;
4-(tert-butyl)-N-(1-ethyl-2-oxo-1,2-dihydrobenzo[cd]indol-6-yl)benzenesulfonamide;
N-(1-ethyl-2-oxo-1,2-dihydrobenzo[cd]indol-6-yl)-4-(trifluoromethoxy)benzenesulfonamide;
3-chloro-N-(1-ethyl-2-oxo-1,2-dihydrobenzo[cd]indol-6-yl)-2-fluorobenzenesulfonamide;
N-(1-ethyl-2-oxo-1,2-dihydrobenzo[cd]indol-6-yl)-4-methylbenzenesulfonamide;
N-(1-ethyl-2-oxo-1,2-dihydrobenzo[cd]indol-6-yl)-2,4-difluorobenzenesulfonamide;
N-(1-ethyl-2-oxo-1,2-dihydrobenzo[cd]indol-6-yl)propane-1-sulfonamide;
N-(1-ethyl-2-oxo-1,2-dihydrobenzo[cd]indol-6-yl)cyclopentanesulfonamide;
N-(1-ethyl-2-oxo-1,2-dihydrobenzo[cd]indol-6-yl)-4-(trifluoromethyl)benzenesulfonamide;
N-(1-ethyl-2-oxo-1,2-dihydrobenzo[cd]indol-6-yl)-3-(methylsulfonyl)benzenesulfonamide;
N-(1-ethyl-2-oxo-1,2-dihydrobenzo[cd]indol-6-yl)naphthalene-2-sulfonamide;
4-(N-(1-ethyl-2-oxo-1,2-dihydrobenzo[cd]indol-6-yl)sulfamoyl)benzoate;
4-(N-(1-ethyl-2-oxo-1,2-dihydrobenzo[cd]indol-6-yl)sulfamoyl)benzoic acid;
3-(N-(1-ethyl-2-oxo-1,2-dihydrobenzo[cd]indol-6-yl)sulfamoyl)benzoate;
3-(N-(1-ethyl-2-oxo-1,2-dihydrobenzo[cd]indol-6-yl)sulfamoyl)benzoic acid;
N-(1-ethyl-2-oxo-1,2-dihydrobenzo[cd]indol-6-yl)-2,3-dihydrobenzo[b][1,4]dioxine-6-sulfonamide;
2-bromo-N-(1-ethyl-2-oxo-1,2-dihydrobenzo[cd]indol-6-yl)benzenesulfonamide;
5-bromo-N-(1-ethyl-2-oxo-1,2-dihydrobenzo[cd]indol-6-yl)-2-methoxybenzenesulfonamide;
2,6-dichloro-N-(1-ethyl-2-oxo-1,2-dihydrobenzo[cd]indol-6-yl)benzenesulfonamide;
N-(1-ethyl-2-oxo-1,2-dihydrobenzo[cd]indol-6-yl)-2,3-dimethoxybenzenesulfonamide;
3,5-dichloro-N-(1-ethyl-2-oxo-1,2-dihydrobenzo[cd]indol-6-yl)benzenesulfonamide;
2,3-dichloro-N-(1-ethyl-2-oxo-1,2-dihydrobenzo[cd]indol-6-yl)benzenesulfonamide;
4-((N-(1-ethyl-2-oxo-1,2-dihydrobenzo[cd]indol-6-yl)sulfamoyl)methyl)benzoate;
4-((N-(1-ethyl-2-oxo-1,2-dihydrobenzo[cd]indol-6-yl)sulfamoyl)methyl)benzoic acid;
N-(1-ethyl-2-oxo-1,2-dihydrobenzo[cd]indol-6-yl)-1-(3-fluorophenyl)methanesulfonamide;
3-((N-(1-ethyl-2-oxo-1,2-dihydrobenzo[cd]indol-6-yl)sulfamoyl)methyl)benzoate;
N-(1-ethyl-2-oxo-1,2-dihydrobenzo[cd]indol-6-yl)-1-(4-(trifluoromethyl)phenyl)methanesulfonamide;
N-(1-ethyl-2-oxo-1,2-dihydrobenzo[cd]indol-6-yl)-1-(p-tolyl)methanesulfonamide;
N-(1-ethyl-2-oxo-1,2-dihydrobenzo[cd]indol-6-yl)-1-(2-fluorophenyl)methanesulfonamide;
1-(4-chlorophenyl)-N-(1-ethyl-2-oxo-1,2-dihydrobenzo[cd]indol-6-yl)methanesulfonamide;
1-(4-cyanophenyl)-N-(1-ethyl-2-oxo-1,2-dihydrobenzo[cd]indol-6-yl)methanesulfonamide;
N-(1-ethyl-2-oxo-1,2-dihydrobenzo[cd]indol-6-yl)-1-(4-fluorophenyl)methanesulfonamide;
N-(1-ethyl-2-oxo-1,2-dihydrobenzo[cd]indol-6-yl)-4-fluorobenzamide;
2-(4-chlorophenyl)-N-(1-ethyl-2-oxo-1,2-dihydrobenzo[cd]indol-6-yl)acetamide;
2-(3,4-dimethoxyphenyl)-N-(1-ethyl-2-oxo-1,2-dihydrobenzo[cd]indol-6-yl)acetamide;
2-(2,4-dichlorophenyl)-N-(1-ethyl-2-oxo-1,2-dihydrobenzo[cd]indol-6-yl)acetamide;
N-(1-ethyl-2-oxo-1,2-dihydrobenzo[cd]indol-6-yl)-3-phenylpropanamide;

N-(1-ethyl-2-oxo-1,2-dihydrobenzo[cd]indol-6-yl)-4,4,4-trifluorobutanamide;
N-(1-ethyl-2-oxo-1,2-dihydrobenzo[cd]indol-6-yl)propionamide;
4-chloro-N-(1-ethyl-2-oxo-1,2-dihydrobenzo[cd]indol-6-yl)benzamide;
N-(1-ethyl-2-oxo-1,2-dihydrobenzo[cd]indol-6-yl)-2-(p-tolyl)acetamide;
(E)-N-(1-ethyl-2-oxo-1,2-dihydrobenzo[cd]indol-6-yl)-3-(furan-2-yl)acrylamide;
1-ethyl-6-((3-phenylpropyl)amino)benzo[cd]indol-2(1H)-one;
1-ethyl-6-((3-morpholinopropyl)amino)benzo[cd]indol-2(1H)-one;
1-ethyl-6-((4-methoxybenzyl)amino)benzo[cd]indol-2(1H)-one;
1-ethyl-6-((4-methylbenzyl)amino)benzo[cd]indol-2(1H)-one;
1-ethyl-6-((4-(trifluoromethyl)benzyl)amino)benzo[cd]indol-2 (1H)-one;
6-((4-chlorobenzyl)amino)-1-ethylbenzo[cd]indol-2(1H)-one;
1-ethyl-6-((4-fluorobenzyl)amino)benzo[cd]indol-2(1H)-one;
N-((1-acetylpiperidin-4-yl)methyl)-1-ethyl-2-oxo-1,2-dihydrobenzo[cd]indole-6-sulfonamide;
1-((1-ethyl-2-oxo-1,2-dihydrobenzo[cd]indole)-6-sulfonamido)cyclohexane-1-carboxamide;
1-ethyl-N-((3-isopropyl-4,5-dihydroisoxazol-5-yl)methyl)-2-oxo-1,2-dihydrobenzo[cd]indole-6-sulfonamide;
N-((3,5-dimethyl-4,5-dihydroisoxazol-5-yl)methyl)-1-ethyl-2-oxo-1,2-dihydrobenzo[cd]indole-6-sulfonamide;
N-(4-acetylphenyl)-1-ethyl-2-oxo-1,2-dihydrobenzo[cd]indole-6-sulfonamide;
N-(2-chlorobenzyl)-1-ethyl-2-oxo-1,2-dihydrobenzo[cd]indole-6-sulfonamide;
1-ethyl-N-(2-fluorobenzyl)-2-oxo-1,2-dihydrobenzo[cd]indole-6-sulfonamide;
N-(1-acetylpiperidin-4-yl)-1-ethyl-2-oxo-1,2-dihydrobenzo[cd]indole-6-sulfonamide;
Tert-butyl 4-(1-ethyl-2-oxo-1,2-dihydrobenzo[cd]indole-6-sulfonamido)piperidine-1-carboxylate;
N-cyclopentyl-1-ethyl-2-oxo-1,2-dihydrobenzo[cd]indole-6-sulfonamide;
Ethyl 1-((1-ethyl-2-oxo-1,2-dihydrobenzo[cd]indole-6-sulfonamido)methyl)cyclopentanecarboxylate;
1-((1-ethyl-2-oxo-1,2-dihydrobenzo[cd]indole-6-sulfonamido)methyl)cyclopentanecarboxylic acid;
N-(4-(1-ethyl-2-oxo-1,2-dihydrobenzo[cd]indole-6-sulfonamido)phenyl)acetamide;
2-(1-ethyl-2-oxo-1,2-dihydrobenzo[cd]indole-6-sulfonamido)benzoic acid;
1-ethyl-N-(4-fluorophenyl)-2-oxo-1,2-dihydrobenzo[cd]indole-6-sulfonamide;
N-butyl-1-ethyl-2-oxo-1,2-dihydrobenzo[cd]indole-6-sulfonamide;
N-(2-(1-ethyl-2-oxo-1,2-dihydrobenzo[cd]indole-6-sulfonamido)ethyl)acetamide;
1-ethyl-N-(2-(methylsulfonyl)ethyl)-2-oxo-1,2-dihydrobenzo[cd]indole-6-sulfonamide;
1-ethyl-2-oxo-N-(2-(2-oxoimidazolidin-1-yl)ethyl)-1,2-dihydrobenzo[cd]indole-6-sulfonamide;
Tert-butyl(4-(1-ethyl-2-oxo-1,2-dihydrobenzo[cd]indole-6-sulfonamido)butyl)carbamate;
N-(5-(1-ethyl-2-oxo-1,2-dihydrobenzo[cd]indole-6-sulfonamido)pyridin-2-yl)acetamide;
Tert-butyl 3-(1-ethyl-2-oxo-1,2-dihydrobenzo[cd]indole-6-sulfonamido)pyrrolidine-1-carboxylate;
Tert-butyl 3-(1-ethyl-2-oxo-1,2-dihydrobenzo[cd]indole-6-sulfonamido)azetidine-1-carboxylate;
N-(2-cyclohexylethyl)-1-ethyl-2-oxo-1,2-dihydrobenzo[cd]indole-6-sulfonamide;
1-ethyl-2-oxo-N-(pyrrolidin-3-yl)-1,2-dihydrobenzo[cd]indole-6-sulfonamide;
N-(azetidin-3-yl)-1-ethyl-2-oxo-1,2-dihydrobenzo[cd]indole-6-sulfonamide;
1-ethyl-N-hexyl-2-oxo-1,2-dihydrobenzo[cd]indole-6-sulfonamide;
1-ethyl-2-oxo-N-(2-(pyrrolidin-1-yl)ethyl)-1,2-dihydrobenzo[cd]indole-6-sulfonamide;
1-ethyl-2-oxo-N-(2-(tetrahydro-2H-pyran-4-yl)ethyl)-1,2-dihydrobenzo[cd]indole-6-sulfonamide;
1-ethyl-2-oxo-N-(tetrahydrofuran-3-yl)-1,2-dihydrobenzo[cd]indole-6-sulfonamide;
N-(2-(4-chlorophenoxy)ethyl)-1-ethyl-2-oxo-1,2-dihydrobenzo[cd]indole-6-sulfonamide;
N,1-diethyl-2-oxo-1,2-dihydrobenzo[cd]indole-6-sulfonamide;
1-ethyl-2-oxo-n-pentyl-1,2-dihydrobenzo[cd]indole-6-sulfonamide;
1-ethyl-N-methyl-2-oxo-1,2-dihydrobenzo[cd]indole-6-sulfonamide;
N-cyclohexyl-1-ethyl-2-oxo-1,2-dihydrobenzo[cd]indole-6-sulfonamide;
Tert-butyl 3-(1-ethyl-2-oxo-1,2-dihydrobenzo[cd]indole-6-sulfonamido)piperidine-1-carboxylate;
1-ethyl-N-isobutyl-2-oxo-1,2-dihydrobenzo[cd]indole-6-sulfonamide;
1-ethyl-2-oxo-N-propyl-1,2-dihydrobenzo[cd]indole-6-sulfonamide;
1-ethyl-N-(3-(4-methylpiperazin-1-yl)propyl)-2-oxo-1,2-dihydrobenzo[cd]indole-6-sulfonamide;
1-ethyl-2-oxo-N-(2-(piperidin-1-yl)ethyl)-1,2-dihydrobenzo[cd]indole-6-sulfonamide;
N-(4,4-diethoxybutyl)-1-ethyl-2-oxo-1,2-dihydrobenzo[cd]indole-6-sulfonamide;
Ethyl 3-(1-ethyl-2-oxo-1,2-dihydrobenzo[cd]indole-6-sulfonamido)propanoate;
1-ethyl-N-((1-ethylpyrrolidin-2-yl)methyl)-2-oxo-1,2-dihydrobenzo[cd]indole-6-sulfonamide;
1-ethyl-N-(1-methylpiperidin-4-yl)-2-oxo-1,2-dihydrobenzo[cd]indole-6-sulfonamide;
N-cycloheptyl-1-ethyl-2-oxo-1,2-dihydrobenzo[cd]indole-6-sulfonamide;
1-ethyl-2-oxo-N-(tetrahydro-2H-pyran-4-yl)-1,2-dihydrobenzo[cd]indole-6-sulfonamide;
Tert-butyl 4-(2-(1-ethyl-2-oxo-1,2-dihydrobenzo[cd]indole-6-sulfonamido)ethyl)piperazine-1-carboxylate;
N-cyclohexyl-1-methyl-2-oxo-1,2-dihydrobenzo[cd]indole-6-sulfonamide;
N-butyl-1-methyl-2-oxo-1,2-dihydrobenzo[cd]indole-6-sulfonamide;
N-cyclohexyl-2-oxo-1-propyl-1,2-dihydrobenzo[cd]indole-6-sulfonamide;
2-oxo-N, 1-dipropyl-1,2-dihydrobenzo[cd]indole-6-sulfonamide;
N-butyl-2-oxo-1-propyl-1,2-dihydrobenzo[cd]indole-6-sulfonamide;
N-butyl-2-oxo-1,2-dihydrobenzo[cd]indole-6-sulfonamide;
N-butyl-1-isobutyl-2-oxo-1,2-dihydrobenzo[cd]indole-6-sulfonamide;
N-cyclohexyl-1-isobutyl-2-oxo-1,2-dihydrobenzo[cd]indole-6-sulfonamide;

N-cyclohexyl-2-oxo-1,2-dihydrobenzo[cd]indole-6-sulfonamide;
N-(3-acetylphenyl)-1-ethyl-2-oxo-1,2-dihydrobenzo[cd]indole-6-sulfonamide;
N-(4-chlorophenyl)-1-ethyl-2-oxo-1,2-dihydrobenzo[cd]indole-6-sulfonamide;
1-ethyl-2-oxo-N-phenyl-1,2-dihydrobenzo[cd]indole-6-sulfonamide;
N-(2-chlorophenyl)-1-ethyl-2-oxo-1,2-dihydrobenzo[cd]indole-6-sulfonamide;
N-(3-chlorophenyl)-1-ethyl-2-oxo-1,2-dihydrobenzo[cd]indole-6-sulfonamide;

In some embodiments, the present invention provides a method of treating a conditions or disease by administering a therapeutically effective amount of compounds of structural formula I, II, III, IV or pharmaceutically acceptable salts, isomers, racemates, prodrugs, cocrystalline complexes, hydrates, and solvates thereof. The disease or condition of interest is treatable by inhibition of BET bromodomains, for Example, a cancer, a cellar proliferative disorder, an inflammatory condition, an autoimmune disorder, sepsis, or a viral infection.

Preferably, the disease to be treated by a compound and method of the present invention is cancer. Examples of treatable cancers include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, actue promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cellieukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcmosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neunnoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor Tlymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer.

Preferably, the present invention provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Preferably, the compounds and methods of the present invention also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystus, agammaglobulinemia, psoriasis, allergy, Crohn's disease, irrtiable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, athersclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierna, mycosis fungoides, acute inflammatory responses (such as acute respiratory distress syndrome and ischemia/reperfusion injury), and Graves' disease.

Preferably, the invention further provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

A compound of structural formula I, II, II, IV can be administered by any suitable route, for Example by oral, buccal, inhalation, sublingual, rectal, vaginal, intracisternal or intrathecal through lumbar puncture, transurethral, nasal, percutaneous, trans dermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration.

In some embodiments, the present invention provides a combination of drugs of structural formula I, II, III, IV or pharmaceutically acceptable salts, isomers, racemates, prodrugs, cocrystalline complexes, hydrates, and solvates thereof.

In some embodiments, the composite can be showed as liquid, semi-liquid or solid form. The method is suitable for the way the medicine is used. The composite can be administered by any suitable route, for Example by oral, parenteral, intraperitoneal, intravenous, subcutaneous, sublingual, intramuscular, rectal, buccal, intranasal, liposome.

In some embodiments, the oral composite can be showed as solid, gel or liquid form. Solid formulations include, but are not limited to, tablets, capsules, granules and bulk powder. These formulations can contain adhesive, thinner, disintegrant, lubricant, flux, sweetener and deodorant. Adhesive include, but are not limited to, microcrystalline cellulose, glucose solution, Arabic jelly, gelatin solution, sucrose and starch paste; Lubricant include, but are not limited to, talc, starch, magnesium stearate, calcium stearate, stearic acid; Thinner include, but are not limited to, lactose, sucrose, starch, glycose and dicalcium phosphate; Flux include, but are not limited to, silicon dioxide; Disintegrant include, but are not limited to, crosslinked carboxymethyl cellulose sodium, starch hydroxyacetate, alginate, corn starch, potato starch, methyl cellulose, AGAR and carboxymethyl cellulose.

In some embodiments, the composite can be formulated for parenteral administration by injection, e.g., intravenous, intramuscular or intravenous injection. Injection can be made as pharmaceutically acceptable forms, e.g., liquid, solution or suspension, a solid form suitable for dissolving or suspending in a liquid prior to injection or an emulsion. The composite can be readily combined with pharmaceutically acceptable carriers well-known in the art, e.g., waterborne carriers, non-aqueous carriers, antimicrobial agents, isotonic agents, buffers, antioxidants, suspensions and dispersants, emulsifiers, chelating agents and other pharmaceutically acceptable substances. Waterborne carriers include, but are not limited to, sodium chloride injection, forest gel injection, isotonic glucose injection, sterile water injection, glucose and lactated Ringer's injection; Non-aqueous carriers include, but are not limited to, fixed oil, cottonseed oil, corn oil, sesame oil and peanut oil; Antimicrobial agents include, but are not limited to, M-cresol, benzyl alcohol, chlorobutanol, benzalkonium chloride; Isotonic agents include, but are not limited to, sodium chloride and glucose; Buffers include, but are not limited to, phosphate and citrate.

In some embodiments, the composite can be formulated for sterile lyophilized powder injection. The composite can be dissolved in sodium phosphate buffer solution (include glucose or other suitable excipient), and then the solution was sterile filtered, followed by lyophilization to give the desired formulation.

As an additional embodiment: the present invention provides compounds of a novel 2-oxo-1,2-dihydrobenzo[cd]indole as scaffold; These compounds can inhibit BET bromodomain protein. Diseases and conditions treatable by a method of the present invention include, but are not limited to, cancers and other proliferative disorders, inflammatory diseases, sepsis, autoimmune disease, and viral infectios.

DETAILED DESCRIPTION

In the compounds of the present invention, when any variable (e.g., $R_1$, $R_2$, etc.) appears more than once in any component, the definition of each occurrence is independent of the other occurrence of each occurrence. Likewise, a combination of substituents and variables is allowed, as long as the combination stabilizes the compound. The lines from the substituents into the ring system indicate that the indicated bond can be attached to any of the substitutable ring atoms. If the ring system is a polycyclic, it means that the bond is only attached to any suitable carbon atom adjacent to the ring. It is to be understood that one of ordinary skill in the art can select the substituents and substitutions of the compounds of the present invention to provide compounds that are chemically stable and readily synthesizable from readily available starting materials by techniques of the art and the methods set forth below. If the substituents themselves are substituted by more than one group, it is to be understood that these groups may be on the same carbon atom or on different carbon atoms as long as the structure is stable. The term "alkyl", "alkylene" as used herein mean to include branched and straight chain saturated aliphatic hydrocarbon groups having a specific number of carbon atoms. For Example, the definition of "C1-C4" in the "C1-C4" alkyl group includes a group having 1, 2, 3, 4 carbon atoms in a straight chain or branched chain. For Example, the "C1-C4" alkyl group specifically includes methyl, ethyl, n-propyl, isopropyl, n-butyl, tert-butyl and isobutyl. Unless additional defined, alkyl, cycloalkyl and heterocyclyl substituents may be unsubstituted or substituted. For Example, the C1-C4 alkyl group may be substituted by one, two or three substituents selected from halogen, methyl, ethyl, propyl, isopropyl, tert-butyl, trifluoromethyl, cyano, amino, phenyl diazenyl, —$CONH_2$, —COOR, —$COR_7$, —$OR_7$, —$NHCOR_7$, —$NHCOOR_7$, —$C_6H_5R_8$, morpholinyl, piperidinyl, tetrahydrofuranyl, pyridyl, wherein $R_7$ is selected from C1-C4 alkyl, phenyl; $R_8$ is optionally substituted with a substituent selected from C1 to C4 alkyl, halogen, acetyl, methoxy, ethoxy.

The present invention includes compounds of formulas I, II, III, IV, and their pharmaceutically acceptable salts and stereoisomers thereof. Pharmaceutically acceptable salts include not only exemplary salts of specific compounds described herein, and also included pharmaceutically acceptable salts from compounds of formula I, II, III, IV or the free form of the compound-specific salt can be isolated using techniques known in the art. For Example, when treated with a suitable dilute aqueous solution of dilute aqueous solution, such as NaOH, $K_2CO_3$, dilute aqueous ammonia, and $NaHCO_3$, the free form of formula I, II, III, IV was regenerated. The free form may be different from salt forms in some physical properties, such as the dissociation in polar solvents, but for the purposes of this invention, the acid salts and base salts are comparable to their respective free forms in other pharmaceuticals.

The pharmaceutically acceptable salts of the present invention can be synthesized from compounds containing the basic or acidic moiety by conventional chemical methods. Typically, the salt of the basic compound is prepared by ion exchange chromatography, or free base with reaction of stoichiometric or excess amount of inorganic/organic acid in a suitable solvent or combination of a plurality of solvents. Similarly, salts of acidic compounds are formed by reaction with an appropriate inorganic/organic base.

Thus, the pharmaceutically acceptable salts of the compounds of the present invention include conventional non-toxic salts by the reaction of a compound of the present invention with an inorganic or organic acid. For Example, conventional non-toxic salts include those derived from inorganic acids, e.g. from hydrochloric acid, hydrobromic acid, sulfuric acid, sulfamic acid, phosphoric acid, nitric acid; from organic acids, e.g. from acetic acid, propionic acid, glycolic acid, lactic acid, malic acid, tartaric acid, citric acid, ascorbic acid, picric acid, maleic acid, hydroxymaleic acid, phenylacetic acid, glutamic acid, benzoic acid, water 2-acetoxy-benzoic acid, fumaric acid, toluenesulfonic acid, methanesulfonic acid, ethane disulfonic acid, oxalic acid, isethionate, trifluoroacetic acid.

For Example, conventional non-toxic salts include those derived from inorganic bases, e.g. from aluminum salts, ammonium salts, calcium salts, copper salts, iron salts, ferrous salts, lithium salts, magnesium salts, manganese salts, manganese salts, potassium salts, sodium salts and zinc salts. Particularly preferred are ammonium salts, calcium salts, magnesium salts, potassium salts and sodium salts; from organic bases, e.g., from primary amine, secondary amine, tertiary amine and naturally substituted amines, cyclic amines and basic ion exchange resins, such as arginine, betaine, caffeine, choline, N,N'-dibenzylethylenediamine, diethylamine, 2-diethylamino ethanol, 2-dimethylaminoethanol, aminoethanol, ethanolamine, ethylenediamine, N-ethylmorpholine, N-ethylpiperidine, glucosamine, glucosamine, histidine, hydroxypropylamine, isopropylamine, lysine, methylglucosamine, morpholine, piperazine, piperidine, guanza, polyamine resin, procaine, purine, theobromine, triethylamine, trimethylamine, tripropylamine, tromethamine.

In addition to the standard methods known in the literature or exemplified in the experimental procedure, the compounds of the present invention can be prepared using the reactions shown in the following schemes. Accordingly, the following illustrative protocols are for illustrative purposes and are not intended to be limited to the listed compounds or any particular substituents. The number of substituents shown in the scheme is not necessarily to be used in the claims. For the sake of clarity, monosubstituted group is attached to a compound showed in invention which is allowed to have a plurality of substituents under the definitions of the formulas I, II, III, IV.

Synthetic Procedures

Synthesis of compounds of formula I. The compounds may be prepared by reacting the 1,8-naphthalenedicarboxylic anhydride as a starting material in 6 steps:

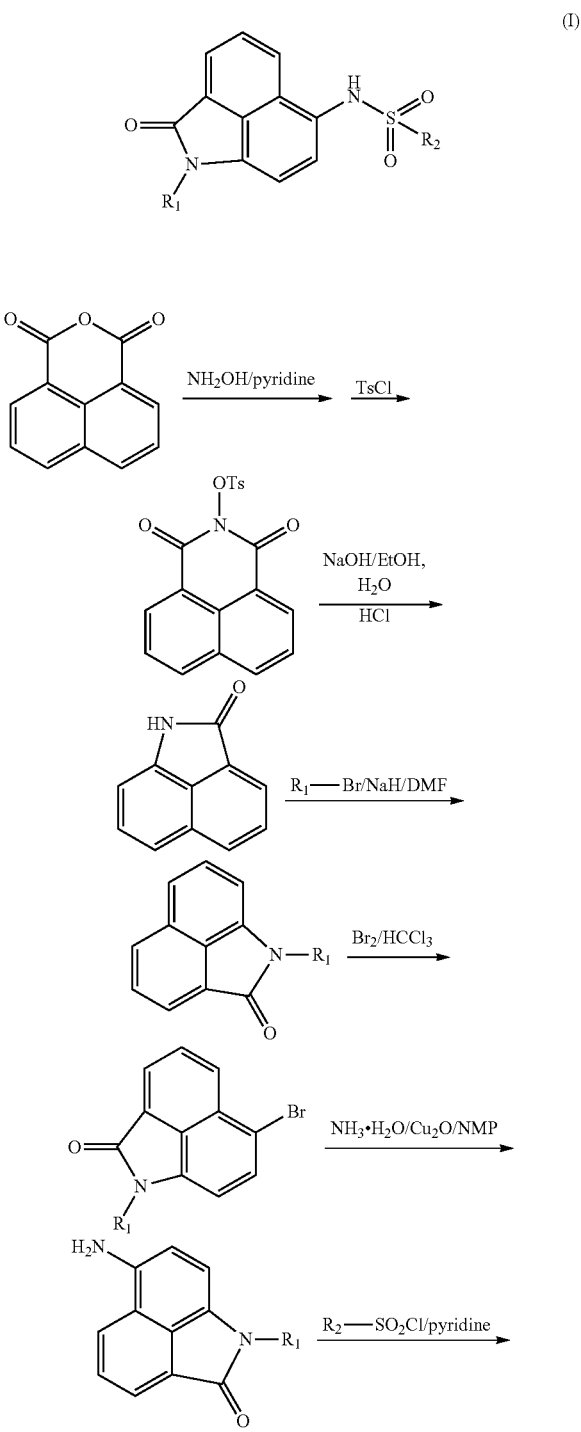

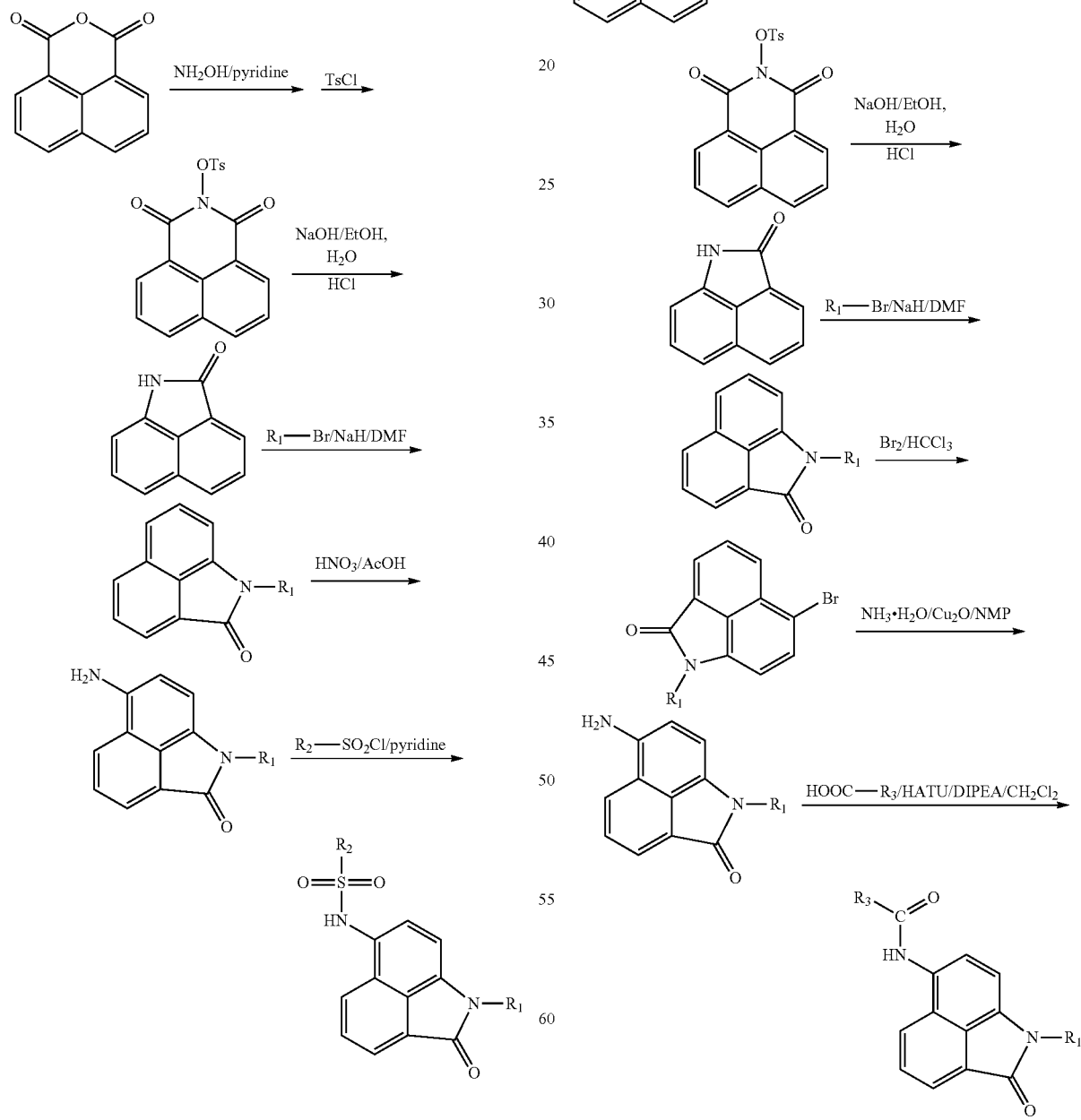
Or by reacting the 1,8-naphthalenedicarboxylic anhydride as a starting material in 5 steps:
Synthesis of compounds of formula II. The compounds may be prepared by reacting the 1,8-naphthalenedicarboxylic anhydride as a starting material in 6 steps:
Or by reacting the 1,8-naphthalenedicarboxylic anhydride as a starting material in 5 steps:

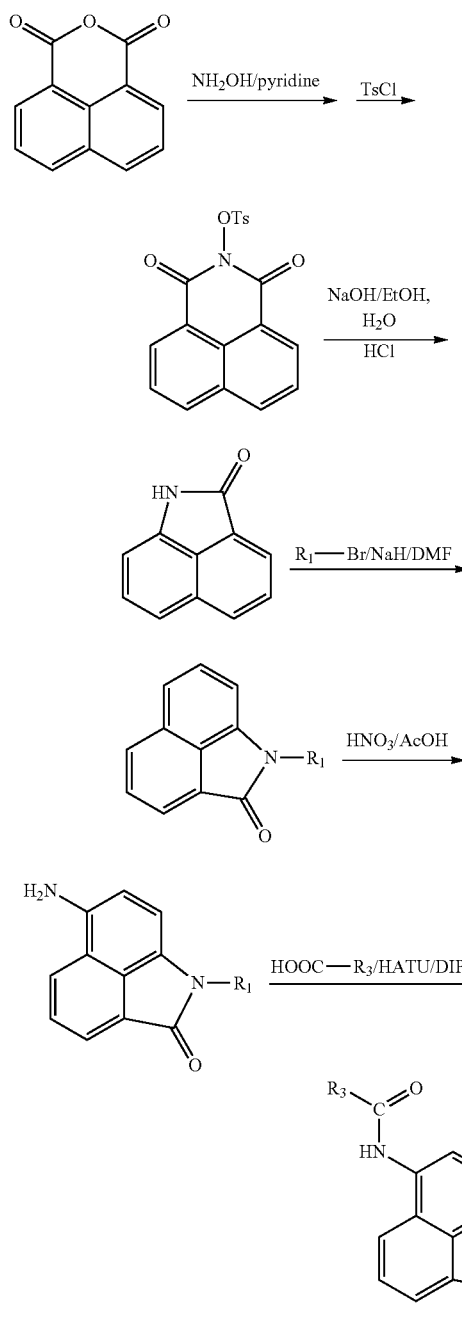
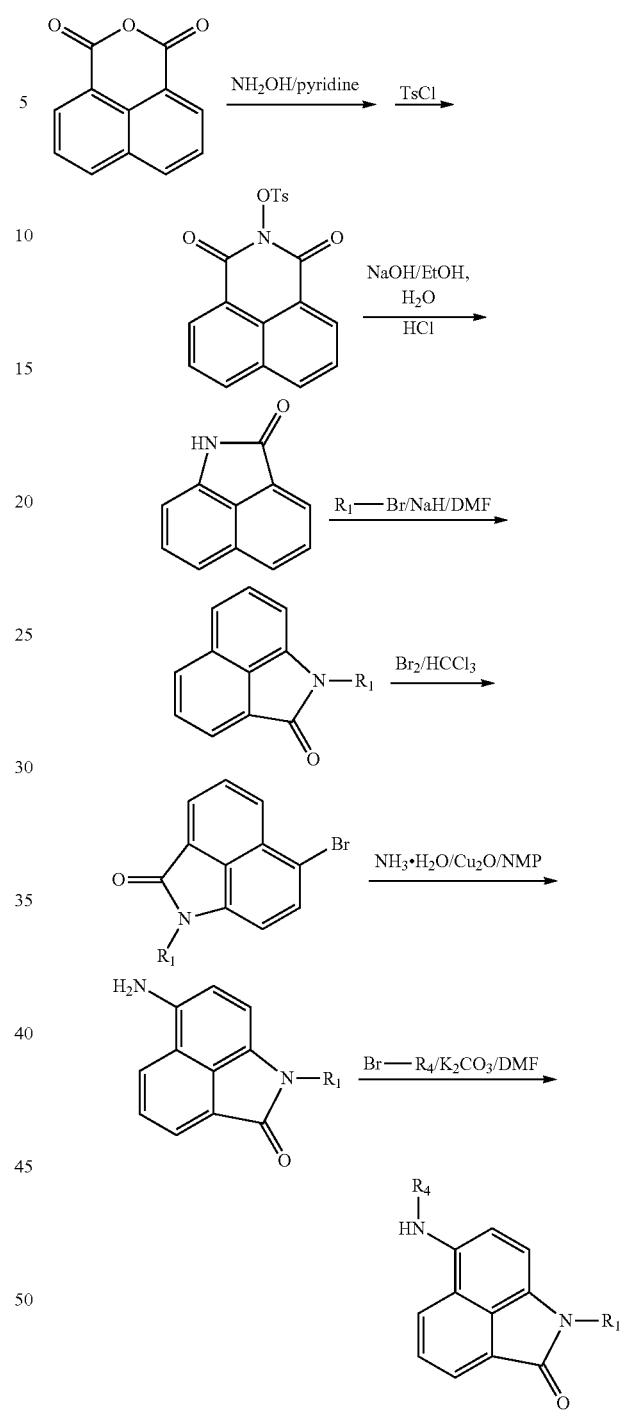
Synthesis of compounds of formula III. The compounds may be prepared by reacting the 1,8-naphthalenedicarboxylic anhydride as a starting material in 6 steps:
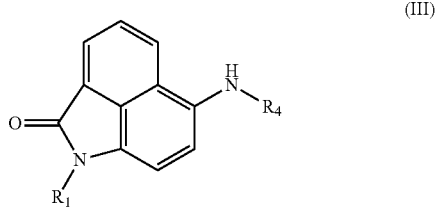
(III)
Or by reacting the 1,8-naphthalenedicarboxylic anhydride as a starting material in 5 steps:
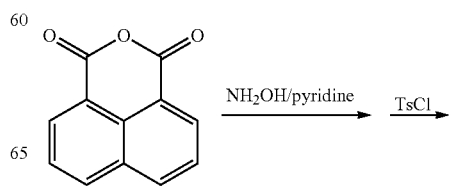

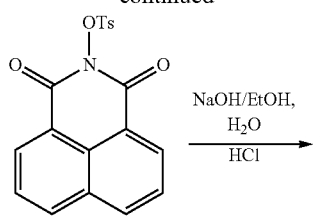
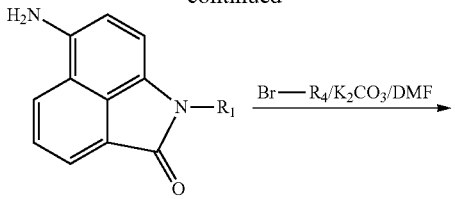
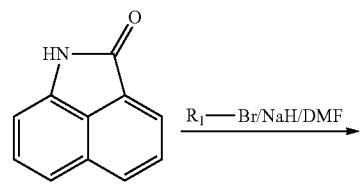
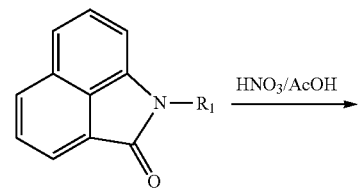
Synthesis of compounds of formula IV. The compounds may be prepared by reacting the 1,8-naphthalenedicarboxylic anhydride as a starting material in 5 steps:
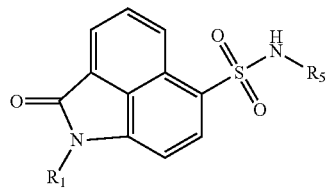
(IV)
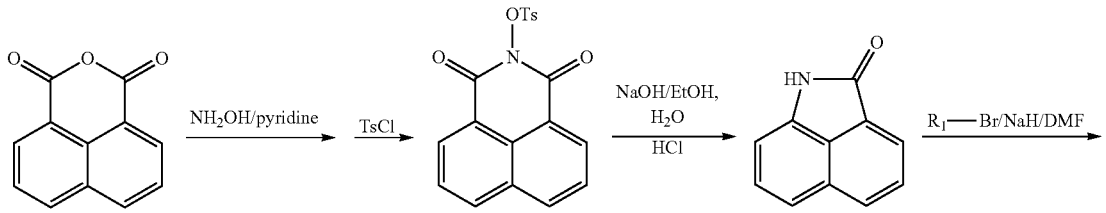
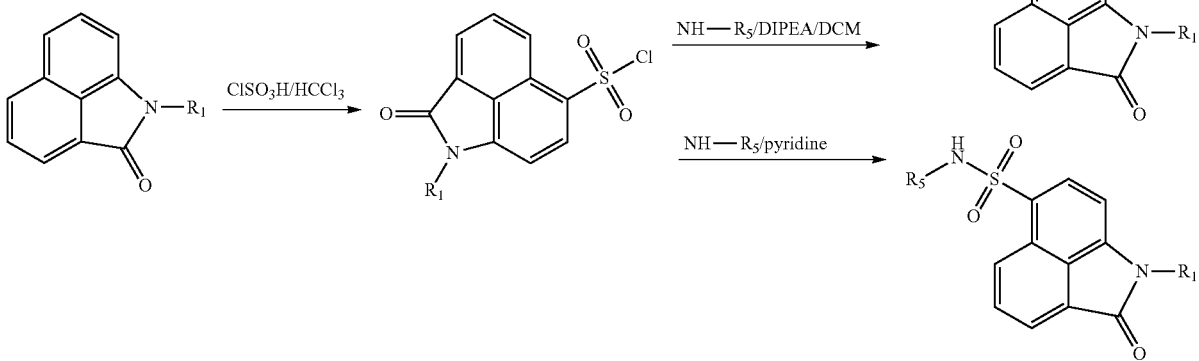

EXAMPLES

The synthesis of formula I:

Example 1

Synthesis of N-ethyl-2-oxo-1,2-dihydrobenzo[cd]indol-6-yl)butane-1-sulfonamide

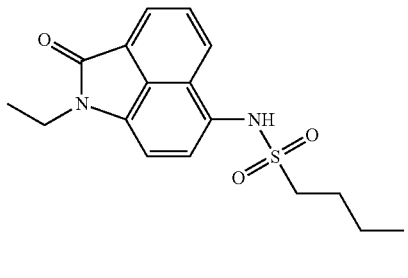 [SMILES: CCCCS(=O)(=O)Nc1ccc2c3c(cccc13)C(=O)N2CC]

Step 1. Synthesis of 1,3-dioxo-1H-benzo[de]isoquinolin-2(3H)-yl 4-methylbenzenesulfonate

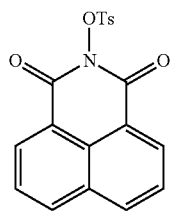 [SMILES: Cc1ccc(S(=O)(=O)ON2C(=O)c3cccc4cccc(c34)C2=O)cc1]

1,8-naphthalenedicarboxylic anhydride (11.9 g, 0.06 mol) and hydroxylamine hydrochloride (4.18 g, 0.06 mol) were combined as a solution in pyridine (70 mL). The reaction was conducted under reflux for 1 h followed by cooling to 80° C. To the reaction system mixture was added powdered p-toluenesulfonyl chloride (22.88 g, 0.12 mol). After the addition, the reaction was performed under reflux for 1 h. After cooling to room temperature, the reaction mixture was poured into ice water (200 mL) and stirred to precipitate crystals. The precipitate was filtered and rinsed with additional cool water (100 mL) and saturated NaHCO$_3$ (100 mL) to give 1,3-dioxo-1H-benzo[de]isoquinolin-2(3H)-yl 4-methyl benzenesulfonate (17 g, 78%) as a yellow solid.

Step 2. Synthesis of benzo[cd]indol-2(1H)-one

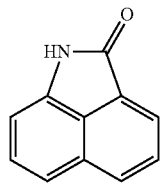

To a solution of 1,3-dioxo-1H-benzo[de]isoquinolin-2(3H)-yl 4-methyl benzenesulfonate (17 g, 0.048 mol) in ethanol (50 mL) and water (40 mL) was added an aqueous solution of sodium hydroxide (2.7 mol/L, 60 mL) at room temperature. The mixture was heated to reflux temperature for 3 h while distilling the ethanol. After the reaction was completed, the reaction mixture was cooled to 75° C., concentrated hydrochloric acid was added dropwise, and a yellow precipitate was formed. Then, the mixture was further cooled. The precipitate was collected by filtration and washed with water (100 mL×2). The resulting crude product was purified by silica gel chromatography with dichloromethane to give Benzo[cd]indol-2(1H)-one (6.65 g, 82%) as a yellow solid. MS (ESI), m/z: M+170.0.

Step 3. Synthesis of 1-ethylbenzo[cd]indol-2(1H)-one

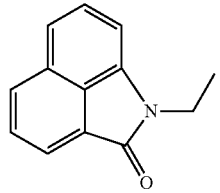

The product benzo[cd]indol-2(1H)-one (6.65 g, 0.04 mol) and NaH (2.81 g, 0.18 mol) were dissolved in DMF (100 mL). Ethyl iodide (7.33 g, 0.047 mol) was added dropwise at 0° C. The reaction mixture was stirred at rt 3 h. The reaction mixture was extracted with ethyl acetate (150 mL×2). The organic layer was washed with brine and dried over Na$_2$SO$_4$. The solid was filtered off, and the filtrate was concentrated under reduced pressure. The resulting crude product was purified by silica gel chromatography with petroleum ether/ethyl acetate (10/1, v/v) to yield 1-ethylbenzo[cd]indol-2(1H)-one (6.46 g, 84%) as a yellow oil. MS (ESI), m/z: M$^+$ 198.0.

Step 4. Synthesis of 1-ethyl-6-nitrobenzo[cd]indol-2(1H)-one

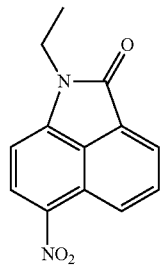 [SMILES: CCN1C(=O)c2cccc3c([N+](=O)[O-])ccc1c23]

To a solution of 1-ethylbenzo[cd]indol-2(1H)-one (500 mg, 2.53 mmol) in AcOH (5 mL) was added HNO$_3$ (154 mg, 2.53 mmol) at 0° C. then the reaction mixture was stirred at 50° C. for 1 h. After the reaction was completed, the reaction mixture was cooled to rt. The reaction mixture was extracted with ethyl acetate (150 mL×2). The organic layer was washed with brine and dried over Na$_2$SO$_4$. The solid was filtered off, and the filtrate was concentrated under reduced pressure. The resulting crude product was purified by silica gel chromatography with petroleum ether/ethyl acetate (6/1, v/v) to yield 1-ethyl-6-nitrobenzo[cd]indol-2(1H)-one (400 mg, 65%) as a yellow solid.

Step 5. Synthesis of 6-amino-1-ethylbenzo[cd]indol-2(1H)-one

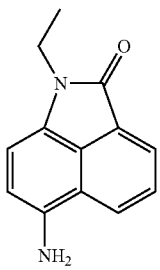

A reaction mixture of Fe power (462 mg, 8.26 mmol) and NH₄Cl (131 mg, 2.47 m mol) in AcOH (2 mL) and water (20 mL) was heated at 50° C. for 5 min. 1-ethyl-6-nitro benzo[cd]indol-2(1H)-one (400 mg, 1.65 mmol) was dissolved in DMF (10 mL) and added to the reaction mixture. After the reaction was completed, the reaction mixture was cooled to rt. The reaction mixture was extracted with ethyl acetate (150 mL×2). The organic layer was washed with brine and dried over Na₂SO₄. The solid was filtered off, and the filtrate was concentrated under reduced pressure. The resulting crude product was purl fled by silica gel chromatography with petroleum ether/ethyl acetate (3/1, v/v) to yield 6-amino-1-ethylbenzo[cd]indol-2(1H)-one (316 mg, 90%) as a yellow solid.

Step 6. Synthesis of N-ethyl-2-oxo-1,2-dihydrobenzo[cd]indol-6-yl)butane-1-sulfonamide A reaction mixture of compound 6-amino-1-ethylbenzo[cd]indol-2(1H)-one (80 mg, 0.38 mmol) and butane-1-sulfonyl chloride (89 mg, 0.57 mmol) in pyridine (5 mL) was stir red at 80° C. for 1 h. Dilute HCl was added, the aqueous layer was extracted with ethyl acetate (50 mL×3), and the organic layer was washed with water and brine, dried with Na₂SO₄ and evaporated. The residue was purified by silica gel chromatography with petroleum and ether/ethyl acetate (4/1, v/v) to afford N-ethyl-2-oxo-1,2-dihydrobenzo[cd]indol-6-yl)butane-1-sulfonamide (66 mg, 52%). ¹H NMR (400 MHz, CDCl₃) δ 8.21 (d, J=8.4 Hz, 1H), 8.10 (d, J=7.2 Hz, 1H), 7.90-7.69 (m, 1H), 7.53 (d, J=7.6 Hz, 1H), 6.88 (d, J=7.6 Hz, 1H), 6.77 (s, 1H), 3.97 (q, J=7.2 Hz, 2H), 3.27-2.89 (m, 2H), 1.94-1.75 (m, 2H), 1.51-1.30 (m, 5H), 0.90 (t, J=7.2 Hz, 3H).

Example 2

Synthesis of 2-chloro-N-(1-ethyl-2-oxo-1,2-dihydrobenzo[cd]indol-6-yl)-4-fluorobenzenesulfonamide

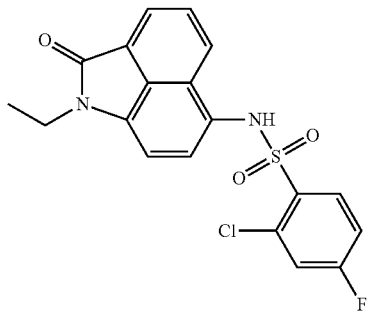 [SMILES: CCN1C(=O)c2cccc3c(NS(=O)(=O)c4ccc(F)cc4Cl)ccc1c23]

The synthesis can refer to Example 1. ¹H NMR (400 MHz, CDCl₃) δ 8.22 (d, J=8.4 Hz, 1H), 8.06 (d, J=7.2 Hz, 1H), 7.86 (dd, J=8.8, 5.6 Hz, 1H), 7.82-7.65 (m, 1H), 7.33 (dd, J=8.0, 2.4 Hz, 1H), 7.26 (s, 1H), 7.13 (d, J=7.6 Hz, 1H), 7.00-6.83 (m, 1H), 6.71 (d, J=7.6 Hz, 1H), 3.91 (q, J=7.2 Hz, 2H), 1.32 (t, J=7.2 Hz, 3H).

Example 3

Synthesis of N-(1-ethyl-2-oxo-1,2-dihydrobenzo[cd]indol-6-yl)thiophene-2-sulfonamide

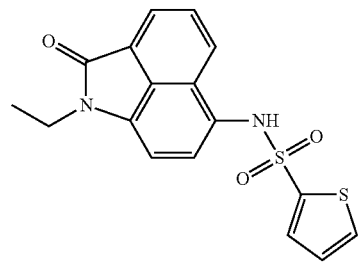 [SMILES: CCN1C(=O)c2cccc3c(NS(=O)(=O)c4cccs4)ccc1c23]

The synthesis can refer to Example 1. ¹H NMR (400 MHz, CDCl₃) δ 8.03 (d, J=7.2 Hz, 1H), 7.92 (d, J=8.4 Hz, 1H), 7.74-7.58 (m, 1H), 7.52 (d, J=5.2 Hz, 1H), 7.41 (d, J=3.6 Hz, 1H), 7.31 (d, J=7.6 Hz, 1H), 7.01-6.93 (m, 1H), 6.91 (s, 1H), 6.82 (d, J=7.6 Hz, 1H), 3.95 (q, J=7.2 Hz, 2H), 1.36 (t, J=7.2 Hz, 3H).

Example 4

Synthesis of 5-chloro-N-(1-ethyl-2-oxo-1,2-dihydrobenzo[cd]indol-6-yl)-2-methoxybenzenesulfonamide

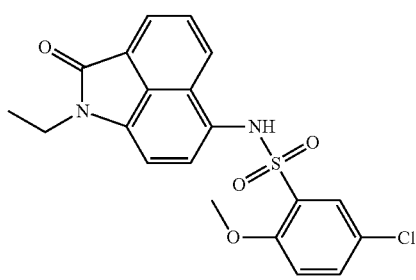 [SMILES: CCN1C(=O)c2cccc3c(NS(=O)(=O)c4cc(Cl)ccc4OC)ccc1c23]

The synthesis can refer to Example 1. ¹H NMR (400 MHz, CDCl₃) δ 8.18 (d, J=8.4 Hz, 1H), 8.05 (d, J=7.2 Hz, 1H), 7.71 (dd, J=15.2, 5.2 Hz, 2H), 7.45 (dd, J=8.8, 2.4 Hz, 1H), 7.25 (s, 1H), 7.13 (d, J=7.6 Hz, 1H), 7.00 (d, J=8.8 Hz, 1H), 6.72 (d, J=7.6 Hz, 1H), 4.08 (s, 3H), 3.91 (q, J=7.2 Hz, 2H), 1.32 (t, J=7.2 Hz, 3H).

Example 5

Synthesis of N-(1-ethyl-2-oxo-1,2-dihydrobenzo[cd]indol-6-yl)cyclohexanesulfonamide

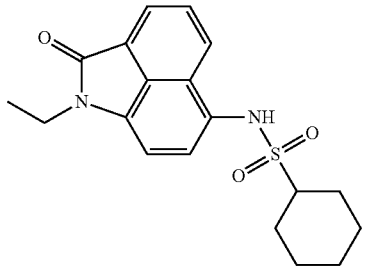 [SMILES: CCN1C(=O)c2cccc3c(NS(=O)(=O)C4CCCCC4)ccc1c23]

The synthesis can refer to Example 1. $^1$H NMR (400 MHz, CDCl$_3$) δ 8.23 (d, J=8.4 Hz, 1H), 8.09 (d, J=7.2 Hz, 1H), 7.78 (t, J=7.6 Hz, 1H), 7.55 (d, J=7.6 Hz, 1H), 7.00-6.72 (m, 2H), 3.96 (q, J=7.2 Hz, 2H), 3.21-2.96 (m, 1H), 2.23 (d, J=112.0 Hz, 2H), 1.87 (d, J=7.6 Hz, 2H), 1.65-1.61 (m, 4H), 1.37 (t, J=7.2 Hz, 3H), 1.19 (d, J=9.2 Hz, 2H).

Example 6

Synthesis of Methyl 2-(N-(1-ethyl-2-oxo-1,2-dihydrobenzo[cd]indol-6-yl)sulfamoyl)benzoate

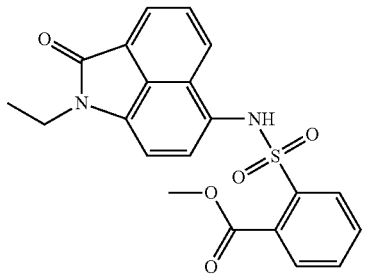 [SMILES: CCN1C(=O)c2cccc3c(NS(=O)(=O)c4ccccc4C(=O)OC)ccc1c23]

The synthesis can refer to Example 1. $^1$H NMR (400 MHz, CDCl$_3$) δ 8.27 (s, 1H), 8.14 (d, J=8.4 Hz, 1H), 8.01 (d, J=7.2 Hz, 1H), 7.86 (d, J=7.2 Hz, 1H), 7.72-7.49 (m, 3H), 7.41 (t, J=7.6 Hz, 1H), 7.33-7.14 (m, 2H), 6.75 (d, J=7.6 Hz, 1H), 4.12 (s, 3H), 3.92 (q, J=7.2 Hz, 2H), 1.34 (t, J=7.2 Hz, 3H).

Example 7

Synthesis of 2-(N-(1-ethyl-2-oxo-1,2-dihydrobenzo[cd]indol-6-yl)sulfamoyl)benzoic acid

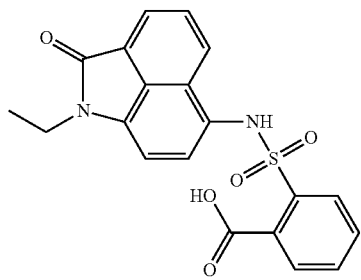 [SMILES: CCN1C(=O)c2cccc3c(NS(=O)(=O)c4ccccc4C(=O)O)ccc1c23]

The synthesis of methyl 2-(N-(1-ethyl-2-oxo-1,2-dihydrobenzo[cd]indol-6-yl)sulfamoyl)benzoate can refer Example 6.

Methyl 2-(N-(1-ethyl-2-oxo-1,2-dihydrobenzo[cd]indol-6-yl)sulfamoyl)benzoate (50 mg, 0.12 mmol) was dissolved in THF (5 mL) and 2 mol/L NaOH aqueous solution (5 mL). The mixture was stirred at room temperature for 2 h. The solvent was removed and diluted hydrochloric acid was added dropwise, and a yellow precipitate was formed. The precipitate was collected by filtration and washed with water (10 mL×2). The resulting crude product was purified by recrystallization with petroleum and ether/ethyl acetate to afford 2-(N-(1-ethyl-2-oxo-1,2-dihydrobenzo[cd]indol-6-yl)sulfamoyl)benzoic acid (33 mg, 69%) as a yellow solid. $^1$H NMR (400 MHz, d-DMSO) δ 10.04 (s, 1H), 8.18 (d, J=8.4 Hz, 1H), 7.98 (d, J=7.2 Hz, 1H), 7.75-7.66 (m, 2H), 7.63 (t, J=7.6 Hz, 1H), 7.57 (d, J=8.0 Hz, 1H), 7.45 (t, J=7.6 Hz, 1H), 7.22 (d, J=7.6 Hz, 1H), 7.10 (d, J=7.6 Hz, 1H), 3.87 (q, J=7.2 Hz, 2H), 1.23 (t, J=7.2 Hz, 3H).

Example 8

Synthesis of N-(1-ethyl-2-oxo-1,2-dihydrobenzo[cd]indol-6-yl)benzenesulfonamide

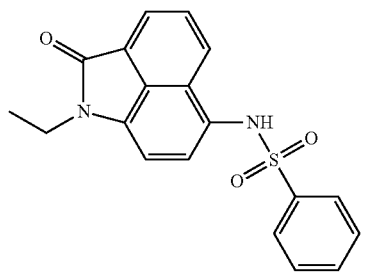 [SMILES: CCN1C(=O)c2cccc3c(NS(=O)(=O)c4ccccc4)ccc1c23]

The synthesis can refer to Example 1. $^1$H NMR (400 MHz, CDCl$_3$) δ 8.00 (d, J=7.2 Hz, 1H), 7.90 (d, J=8.4 Hz, 1H), 7.74 (d, J=7.6 Hz, 2H), 7.60 (t, J=7.6 Hz, 1H), 7.54-7.49 (m, 1H), 7.39 (t, J=7.6 Hz, 2H), 7.21 (d, J=7.6 Hz, 1H), 7.06 (s, 1H), 6.77 (d, J=7.6 Hz, 1H), 3.93 (q, J=7.2 Hz, 2H), 1.34 (t, J=7.2 Hz, 3H).

Example 9

Synthesis of N-(1-ethyl-2-oxo-1,2-dihydrobenzo[cd]indol-6-yl)-4-fluorobenzenesulfonamide

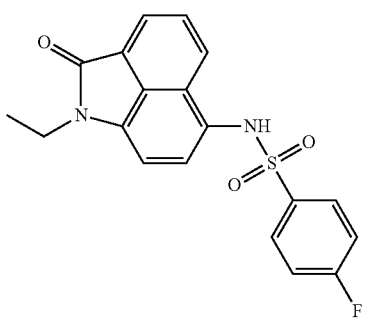 [SMILES: CCN1C(=O)c2cccc3c(NS(=O)(=O)c4ccc(F)cc4)ccc1c23]

The synthesis can refer to Example 1. $^1$H NMR (400 MHz, d-DMSO) δ 10.29 (s, 1H), 8.03 (dd, J=16.4, 7.6 Hz, 2H), 7.84-7.63 (m, 3H), 7.33 (t, J=8.8 Hz, 2H), 7.13 (s, 2H), 3.87 (q, J=7.2 Hz, 2H), 1.23 (t, J=7.2 Hz, 3H).

Example 10

Synthesis of N-(1-ethyl-2-oxo-1,2-dihydrobenzo[cd]indol-6-yl)-3-fluorobenzenesulfonamide

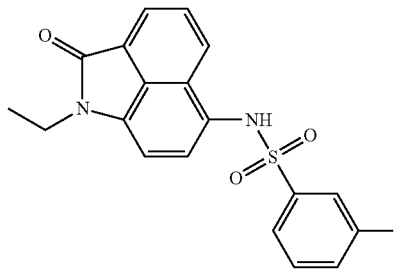

The synthesis can refer to Example 1. ¹H NMR (400 MHz, CDCl$_3$) δ 8.03 (d, J=7.2 Hz, 1H), 7.91 (d, J=8.4 Hz, 1H), 7.65 (t, J=7.6 Hz, 1H), 7.66-7.45 (m, 2H), 7.38 (dd, J=13.2, 8.0 Hz, 1H), 7.25 (d, J=4.8 Hz, 1H), 7.20 (s, 1H), 6.79 (d, J=7.6 Hz, 1H), 3.94 (q, J=7.2 Hz, 2H), 1.35 (t, J=7.2 Hz, 3H).

Example 11

Synthesis of N-(1-ethyl-2-oxo-1,2-dihydrobenzo[cd]indol-6-yl)ethanesulfonamide

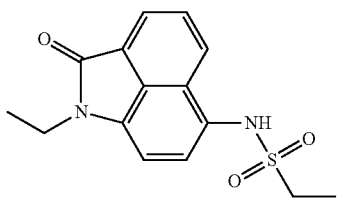 [SMILES: CCN1C(=O)c2cccc3c(NS(=O)(=O)CC)ccc1c23]

The synthesis can refer to Example 1. ¹H NMR (400 MHz, CDCl$_3$) δ 8.22 (d, J=8.4 Hz, 1H), 8.10 (d, J=7.2 Hz, 1H), 7.80 (t, J=7.6 Hz, 1H), 7.54 (d, J=7.6 Hz, 1H), 6.93-6.76 (m, 2H), 3.97 (q, J=7.2 Hz, 2H), 3.16 (q, J=7.2 Hz, 2H), 1.43 (t, J=7.2 Hz, 3H), 1.37 (t, J=7.2 Hz, 3H).

Example 12

Synthesis of N-(1-ethyl-2-oxo-1,2-dihydrobenzo[cd]indol-6-yl)-4-methoxybenzenesulfonamide

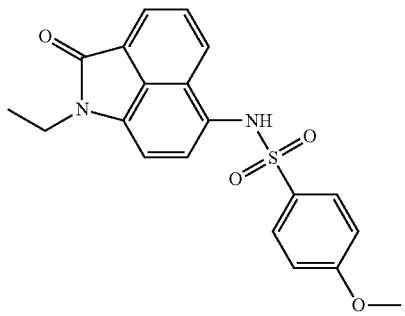 [SMILES: CCN1C(=O)c2cccc3c(NS(=O)(=O)c4ccc(OC)cc4)ccc1c23]

The synthesis can refer to Example 1. ¹H NMR (400 MHz, CDCl$_3$) δ 8.02 (d, J=7.2 Hz, 1H), 7.95 (d, J=8.4 Hz, 1H), 7.79-7.51 (m, 3H), 7.20 (d, J=7.6 Hz, 1H), 6.89 (s, 1H), 6.84 (d, J=8.8 Hz, 2H), 6.77 (d, J=7.6 Hz, 1H), 3.93 (q, J=7.2 Hz, 2H), 1.35 (t, J=7.2 Hz, 3H).

Example 13

Synthesis of 4-cyano-N-(1-ethyl-2-oxo-1,2-dihydrobenzo[cd]indol-6-yl)benzenesulfonamide

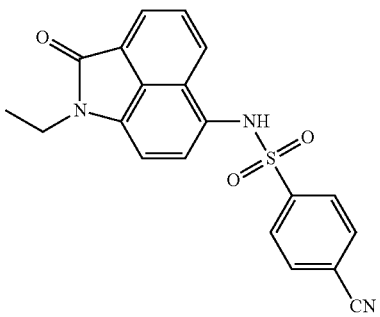 [SMILES: CCN1C(=O)c2cccc3c(NS(=O)(=O)c4ccc(C#N)cc4)ccc1c23]

The synthesis can refer to Example 1. ¹H NMR (400 MHz, CDCl$_3$) δ 8.04 (d, J=7.2 Hz, 1H), 7.89 (d, J=8.4 Hz, 1H), 7.85 (d, J=8.4 Hz, 2H), 7.74-7.57 (m, 3H), 7.17 (d, J=7.6 Hz, 1H), 7.11 (s, 1H), 6.79 (d, J=7.6 Hz, 1H), 3.94 (q, J=7.2 Hz, 2H), 1.35 (t, J=7.2 Hz, 3H).

Example 14

Synthesis of N-(1-ethyl-2-oxo-1,2-dihydrobenzo[cd]indol-6-yl)-4-nitrobenzenesulfonamide

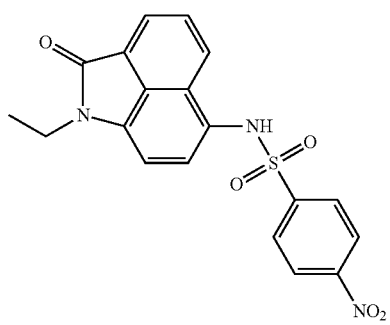 [SMILES: CCN1C(=O)c2cccc3c(NS(=O)(=O)c4ccc([N+](=O)[O-])cc4)ccc1c23]

The synthesis can refer to Example 1. ¹H NMR (400 MHz, CDCl$_3$) δ 8.25 (d, J=8.8 Hz, 2H), 8.05 (d, J=7.2 Hz, 1H), 7.92 (d, J=9.2 Hz, 3H), 7.67 (t, J=7.6 Hz, 1H), 7.17 (d, J=7.6 Hz, 1H), 6.95 (s, 1H), 6.79 (d, J=7.6 Hz, 1H), 3.94 (q, J=7.2 Hz, 2H), 1.36 (t, J=7.2 Hz, 3H).

Example 15

Synthesis of 4-(tert-butyl)-N-(1-ethyl-2-oxo-1,2-dihydrobenzo[cd]indol-6-yl)benzenesulfonamide

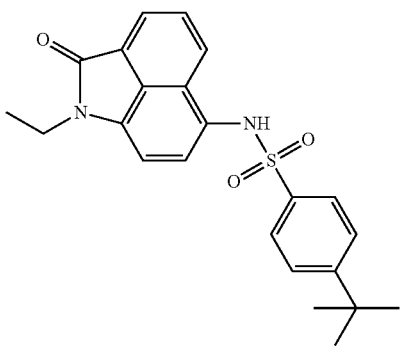 [SMILES: CCN1C(=O)c2cccc3c(NS(=O)(=O)c4ccc(C(C)(C)C)cc4)ccc1c23]

The synthesis can refer to Example 1. ¹H NMR (400 MHz, CDCl₃) δ 7.99 (d, J=7.2 Hz, 1H), 7.78 (d, J=8.4 Hz, 1H), 7.63 (d, J=8.4 Hz, 2H), 7.60-7.48 (m, 1H), 7.37 (d, J=8.4 Hz, 2H), 7.28 (s, 1H), 6.80 (d, J=7.6 Hz, 2H), 3.94 (q, J=7.2 Hz, 2H), 1.36 (t, J=7.2 Hz, 3H), 1.27 (s, 9H).

Example 16

Synthesis of N-(1-ethyl-2-oxo-1,2-dihydrobenzo[cd]indol-6-yl)-4-(trifluoromethoxy)benzenesulfonamide

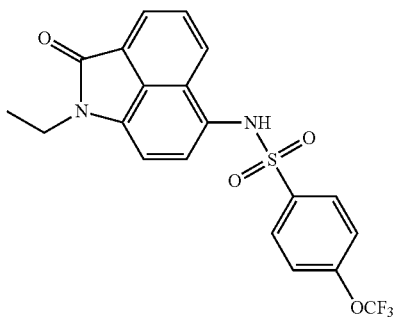 [SMILES: CCN1C(=O)c2cccc3c(NS(=O)(=O)c4ccc(OC(F)(F)F)cc4)ccc1c23]

The synthesis can refer to Example 1. ¹H NMR (400 MHz, CDCl₃) δ 8.05 (d, J=7.2 Hz, 1H), 7.86 (d, J=8.4 Hz, 1H), 7.79 (d, J=8.8 Hz, 2H), 7.71-7.53 (m, 1H), 7.23 (d, J=7.6 Hz, 3H), 6.87 (s, 1H), 6.82 (d, J=7.6 Hz, 1H), 3.97 (q, J=7.2 Hz, 2H), 1.38 (t, J=7.2 Hz, 3H).

Example 17

Synthesis of 3-chloro-N-(1-ethyl-2-oxo-1,2-dihydrobenzo[cd]indol-6-yl)-2-fluorobenzenesulfonamide

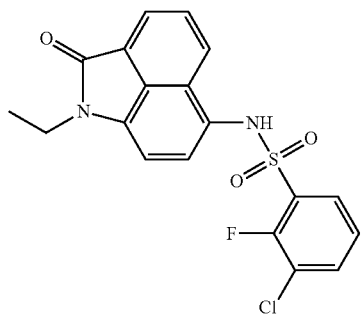 [SMILES: CCN1C(=O)c2cccc3c(NS(=O)(=O)c4cccc(Cl)c4F)ccc1c23]

The synthesis can refer to Example 1. ¹H NMR (400 MHz, d-DMSO) δ 10.82 (s, 1H), 8.12 (d, J=8.4 Hz, 1H), 8.03 (d, J=6.8 Hz, 1H), 7.82 (dd, J=17.6, 10.0 Hz, 1H), 7.76 (d, J=7.2 Hz, 1H), 7.59 (t, J=7.2 Hz, 1H), 7.28 (t, J=8.0 Hz, 1H), 7.22 (d, J=7.6 Hz, 1H), 7.13 (d, J=7.6 Hz, 1H), 3.87 (q, J=7.2 Hz, 2H), 1.23 (t, J=7.2 Hz, 3H).

Example 18

Synthesis of N-(1-ethyl-2-oxo-1,2-dihydrobenzo[cd]indol-6-yl)-4-methylbenzenesulfonamide

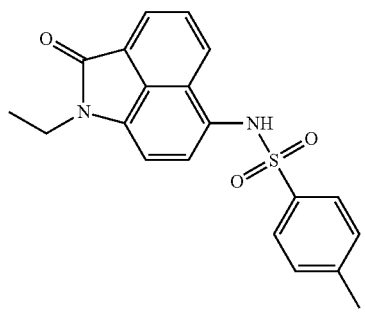 [SMILES: CCN1C(=O)c2cccc3c(NS(=O)(=O)c4ccc(C)cc4)ccc1c23]

The synthesis can refer to Example 1. ¹H NMR (400 MHz, CDCl₃) δ 8.02 (d, J=7.2 Hz, 1H), 7.93 (d, J=8.4 Hz, 1H), 7.63 (t, J=8.4 Hz, 3H), 7.19 (dd, J=7.6, 5.2 Hz, 3H), 6.85 (s, 1H), 6.77 (d, J=7.6 Hz, 1H), 3.93 (q, J=7.2 Hz, 2H), 2.36 (s, 3H), 1.35 (t, J=7.2 Hz, 3H).

Example 19

Synthesis of N-(1-ethyl-2-oxo-1,2-dihydrobenzo[cd]indol-6-yl)-2,4-difluorobenzenesulfonamide

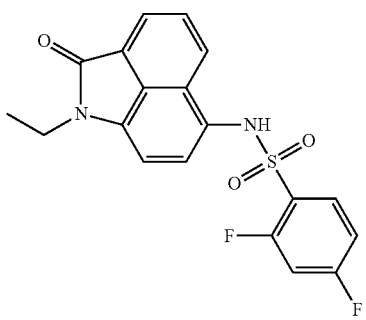 [SMILES: CCN1C(=O)c2cccc3c(NS(=O)(=O)c4ccc(F)cc4F)ccc1c23]

The synthesis can refer to Example 1. ¹H NMR (400 MHz, CDCl₃) δ 8.14 (d, J=8.4 Hz, 1H), 8.05 (d, J=7.2 Hz, 1H), 7.75-7.70 (m, 2H), 7.23 (d, J=7.6 Hz, 1H), 7.07 (s, 1H), 7.01-6.91 (m, 1H), 6.87 (dd, J=11.6, 5.2 Hz, 1H), 6.75 (d, J=7.6 Hz, 1H), 3.92 (q, J=7.2 Hz, 2H), 1.33 (t, J=7.2 Hz, 3H).

Example 20

Synthesis of N-(1-ethyl-2-oxo-1,2-dihydrobenzo[cd]indol-6-yl)propane-1-sulfonamide

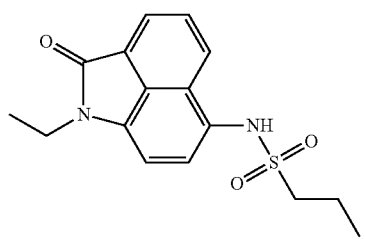 [SMILES: CCCS(=O)(=O)Nc1ccc2c3c(cccc13)C(=O)N2CC]

The synthesis can refer to Example 1. ¹H NMR (400 MHz, CDCl₃) δ 8.22 (d, J=8.0 Hz, 1H), 8.09 (d, J=6.8 Hz, 1H), 7.79 (t, J=7.2 Hz, 1H), 7.53 (d, J=7.2 Hz, 1H), 6.99 (s, 1H), 6.88 (d, J=7.2 Hz, 1H), 3.97 (q, J=7.2 Hz, 2H), 3.30-2.79 (m, 2H), 1.91 (dd, J=14.8, 7.2 Hz, 2H), 1.37 (t, J=6.8 Hz, 3H), 1.02 (t, J=7.2 Hz, 3H).

Example 21

Synthesis of N-(1-ethyl-2-oxo-1,2-dihydrobenzo[cd]indol-6-yl)cyclopentanesulfonamide

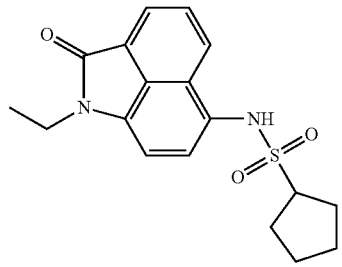 [SMILES: CCN1C(=O)c2cccc3c(NS(=O)(=O)C4CCCC4)ccc1c23]

The synthesis can refer to Example 1. ¹H NMR (400 MHz, CDCl₃) δ 8.25 (d, J=8.0 Hz, 1H), 8.08 (d, J=6.8 Hz, 1H), 7.77 (t, J=7.2 Hz, 1H), 7.58 (d, J=7.2 Hz, 1H), 7.16 (s, 1H), 6.86 (d, J=7.2 Hz, 1H), 3.96 (q, J=7.2 Hz, 2H), 3.51-3.46 (m, 1H), 2.13-2.03 (m, 4H), 1.95-1.78 (m, 4H), 1.36 (t, J=7.2 Hz, 3H).

Example 22

Synthesis of N-(1-ethyl-2-oxo-1,2-dihydrobenzo[cd]indol-6-yl)-4-(trifluoromethyl)benzenesulfonamide

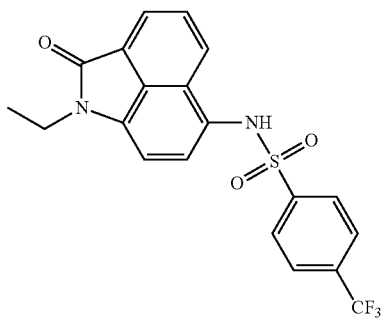 [SMILES: CCN1C(=O)c2cccc3c(NS(=O)(=O)c4ccc(C(F)(F)F)cc4)ccc1c23]

The synthesis can refer to Example 1. ¹H NMR (400 MHz, CDCl₃) δ 8.04 (d, J=6.8 Hz, 1H), 7.96-7.73 (m, 3H), 7.68-7.62 (m, 3H), 7.18 (d, J=7.6 Hz, 1H), 6.88 (s, 1H), 6.79 (d, J=7.2 Hz, 1H), 3.94 (q, J=7.2 Hz, 2H), 1.36 (t, J=7.2 Hz, 3H).

Example 23

Synthesis of N-(1-ethyl-2-oxo-1,2-dihydrobenzo[cd]indol-6-yl)-3-(methylsulfonyl)benzenesulfonamide

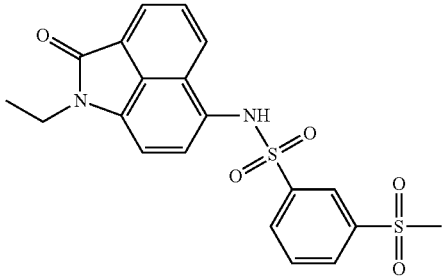 [SMILES: CCN1C(=O)c2cccc3c(NS(=O)(=O)c4cccc(S(C)(=O)=O)c4)ccc1c23]

The synthesis can refer to Example 1. ¹H NMR (400 MHz, d-DMSO) δ 10.49 (s, 1H), 8.14 (d, J=9.6 Hz, 2H), 8.00 (d, J=7.2 Hz, 2H), 7.93 (d, J=7.6 Hz, 1H), 7.77 (t, J=7.6 Hz, 1H), 7.69 (t, J=7.6 Hz, 1H), 7.13 (s, 2H), 3.87 (d, J=7.2 Hz, 2H), 3.17 (s, 3H), 1.23 (t, J=6.8 Hz, 3H).

Example 24

Synthesis of N-(1-ethyl-2-oxo-1,2-dihydrobenzo[cd]indol-6-yl)naphthalene-1-sulfonamide

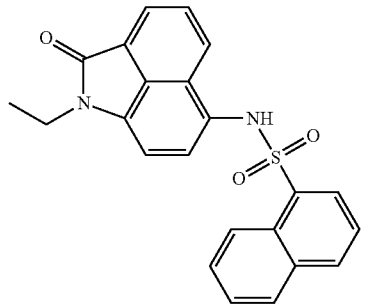 [SMILES: CCN1C(=O)c2cccc3c(NS(=O)(=O)c4cccc5ccccc45)ccc1c23]

The synthesis can refer to Example 1. ¹H NMR (400 MHz, d-DMSO) δ 10.61 (s, 1H), 8.80 (d, J=8.4 Hz, 1H), 8.15 (d, J=8.0 Hz, 1H), 8.04 (d, J=7.6 Hz, 1H), 7.98 (d, J=7.2 Hz, 1H), 7.92 (t, J=7.6 Hz, 2H), 7.72-7.65 (m, 2H), 7.53-7.49 (m, 2H), 7.09 (d, J=7.6 Hz, 1H), 7.02 (d, J=7.6 Hz, 1H), 3.82 (q, J=7.2 Hz, 2H), 1.18 (t, J=7.2 Hz, 3H).

Example 25

Synthesis of Methyl 4-(N-(1-ethyl-2-oxo-1,2-dihydrobenzo[cd]indol-6-yl)sulfamoyl)benzoate

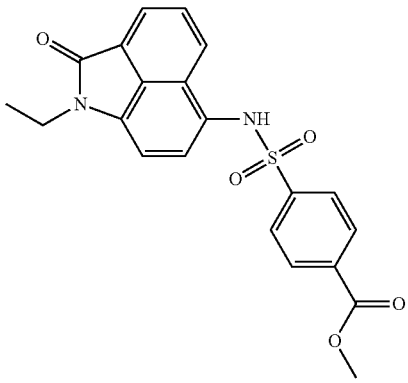 [SMILES: CCN1C(=O)c2cccc3c(NS(=O)(=O)c4ccc(C(=O)OC)cc4)ccc1c23]

The synthesis can refer to Example 1. ¹H NMR (400 MHz, d-DMSO) δ 10.46 (s, 1H), 8.04 (d, J=8.4 Hz, 3H), 8.00 (d, J=7.2 Hz, 1H), 7.80 (d, J=8.4 Hz, 2H), 7.70 (t, J=7.6 Hz, 1H), 7.11 (s, 2H), 3.87 (q, J=7.2 Hz, 5H), 1.23 (t, J=7.2 Hz, 3H).

Example 26

Synthesis of 4-(N-(1-ethyl-2-oxo-1,2-dihydrobenzo [cd]indol-6-yl)sulfamoyl)benzoic acid

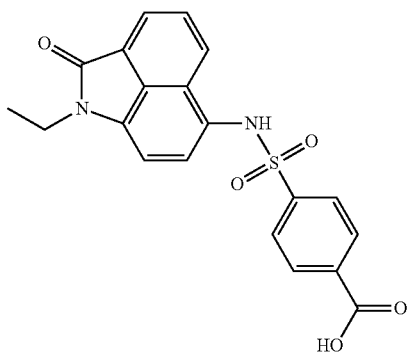 [SMILES: CCN1C(=O)c2cccc3c(NS(=O)(=O)c4ccc(C(=O)O)cc4)ccc1c23]

The synthesis can refer to Example 7. ¹H NMR (400 MHz, d-DMSO) δ 13.41 (s, 1H), 10.44 (s, 1H), 8.17-7.92 (m, 4H), 7.77 (d, J=8.0 Hz, 2H), 7.70 (t, J=7.6 Hz, 1H), 7.11 (s, 2H), 3.86 (q, J=7.2 Hz, 2H), 1.23 (t, J=7.2 Hz, 3H).

Example 27

Synthesis of methyl 3-(N-(1-ethyl-2-oxo-1,2-dihydrobenzo[cd]indol-6-yl)sulfamoyl)benzoate

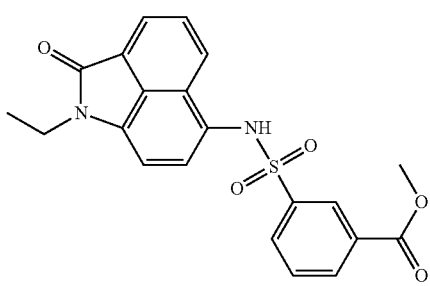 [SMILES: CCN1C(=O)c2cccc3c(NS(=O)(=O)c4cccc(C(=O)OC)c4)ccc1c23]

The synthesis can refer to Example 1. ¹H NMR (400 MHz, d-DMSO) δ 10.43 (s, 1H), 8.22 (s, 1H), 8.12 (d, J=7.6 Hz, 1H), 8.04-7.98 (m, 2H), 7.86 (d, J=7.6 Hz, 1H), 7.70-7.61 (m, 2H), 7.11 (s, 2H), 3.93-3.77 (m, 5H), 1.22 (t, J=7.1 Hz, 3H).

Example 28

Synthesis of 3-(N-(1-ethyl-2-oxo-1,2-dihydrobenzo [cd]indol-6-yl)sulfamoyl)benzoic acid

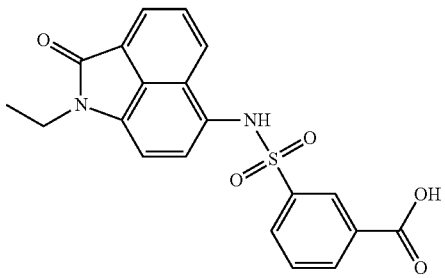 [SMILES: CCN1C(=O)c2cccc3c(NS(=O)(=O)c4cccc(C(=O)O)c4)ccc1c23]

The synthesis can refer to Example 7. ¹H NMR (400 MHz, d-DMSO) δ 13.27 (s, 1H), 10.39 (s, 1H), 8.21 (s, 1H), 8.10 (d, J=7.6 Hz, 1H), 8.01-7.98 (m, 2H), 7.84 (d, J=7.6 Hz, 1H), 7.68 (t, J=7.6 Hz, 1H), 7.61 (t, J=7.6 Hz, 1H), 7.11 (s, 2H), 3.86 (q, J=7.2 Hz, 2H), 1.22 (t, J=7.2 Hz, 3H).

Example 29

Synthesis of N-(1-ethyl-2-oxo-1,2-dihydrobenzo[cd] indol-6-yl)-2,3-dihydrobenzo[b][1,4]dioxine-6-sulfonamide

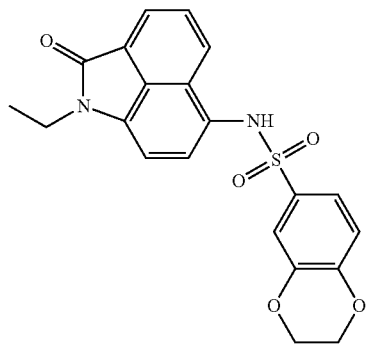 [SMILES: CCN1C(=O)c2cccc3c(NS(=O)(=O)c4ccc5c(c4)OCCO5)ccc1c23]

The synthesis can refer to Example 1. ¹H NMR (400 MHz, d-DMSO) δ 10.14 (s, 1H), 8.10 (d, J=8.4 Hz, 1H), 8.01 (d, J=6.8 Hz, 1H), 7.73 (t, J=7.6 Hz, 1H), 7.26-7.00 (m, 4H), 6.91 (d, J=8.4 Hz, 1H), 4.25 (d, J=9.2 Hz, 4H), 3.87 (q, J=7.2 Hz, 2H), 1.23 (t, J=7.2 Hz, 3H).

Example 30

Synthesis of 2-bromo-N-(1-ethyl-2-oxo-1,2-dihydrobenzo[cd]indol-6-yl)benzenesulfonamide

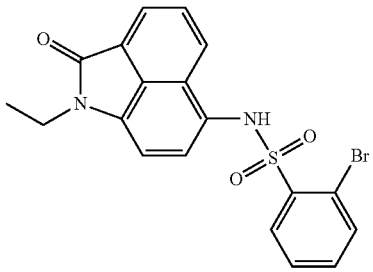 [SMILES: CCN1C(=O)c2cccc3c(NS(=O)(=O)c4ccccc4Br)ccc1c23]

The synthesis can refer to Example 1. ¹H NMR (400 MHz, CDCl₃) δ 8.26 (d, J=8.4 Hz, 1H), 8.05 (d, J=7.2 Hz, 1H), 7.87 (d, J=7.6 Hz, 1H), 7.80 (d, J=7.6 Hz, 1H), 7.73 (t, J=7.6 Hz, 1H), 7.40 (t, J=7.6 Hz, 1H), 7.36-7.28 (m, 2H), 7.11 (d, J=7.6 Hz, 1H), 6.69 (d, J=7.6 Hz, 1H), 3.90 (q, J=7.2 Hz, 2H), 1.31 (t, J=7.2 Hz, 3H).

Example 31

Synthesis of 5-bromo-N-(1-ethyl-2-oxo-1,2-dihydrobenzo[cd]indol-6-yl)-2-methoxybenzenesulfonamide

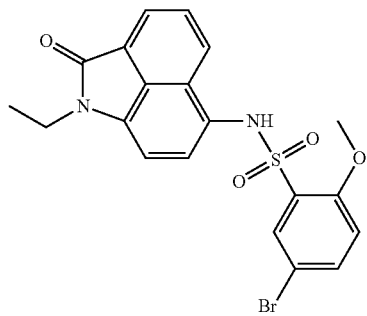 [SMILES: CCN1C(=O)c2cccc3c(NS(=O)(=O)c4cc(Br)ccc4OC)ccc1c23]

The synthesis can refer to Example 1. ¹H NMR (400 MHz, d-DMSO) δ 10.29 (s, 1H), 8.24 (d, J=8.4 Hz, 1H), 8.02 (d, J=6.8 Hz, 1H), 7.79 (t, J=7.6 Hz, 1H), 7.71 (d, J=8.8 Hz, 1H), 7.61 (s, 1H), 7.24 (d, J=7.6 Hz, 1H), 7.15 (d, J=8.8 Hz, 1H), 7.10 (d, J=7.6 Hz, 1H), 3.98-3.57 (m, 5H), 1.22 (t, J=7.2 Hz, 3H).

Example 32

Synthesis of 2,6-dichloro-N-(1-ethyl-2-oxo-1,2-dihydrobenzo[cd]indol-6-yl)benzenesulfonamide

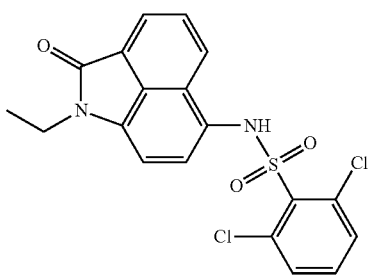 [SMILES: CCN1C(=O)c2cccc3c(NS(=O)(=O)c4c(Cl)cccc4Cl)ccc1c23]

The synthesis can refer to Example 1. ¹H NMR (400 MHz, CDCl₃) δ 8.17 (d, J=8.0 Hz, 1H), 8.05 (d, J=7.2 Hz, 1H), 7.73 (t, J=7.6 Hz, 1H), 7.50 (s, 1H), 7.45 (d, J=8.0 Hz, 2H), 7.38-7.29 (m, 1H), 7.22 (d, J=7.6 Hz, 1H), 6.74 (d, J=7.6 Hz, 1H), 3.92 (q, J=7.2 Hz, 2H), 1.33 (t, J=7.2 Hz, 3H).

Example 33

Synthesis of N-(1-ethyl-2-oxo-1,2-dihydrobenzo[cd]indol-6-yl)-2,5-dimethoxybenzenesulfonamide

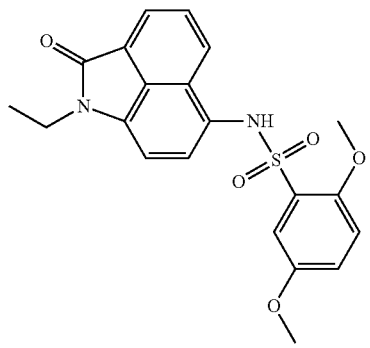 [SMILES: CCN1C(=O)c2cccc3c(NS(=O)(=O)c4cc(OC)ccc4OC)ccc1c23]

The synthesis can refer to Example 1. ¹H NMR (400 MHz, CDCl₃) δ 8.23 (d, J=8.4 Hz, 1H), 8.04 (d, J=7.2 Hz, 1H), 7.72 (t, J=7.6 Hz, 1H), 7.27 (d, J=4.4 Hz, 1H), 7.22 (s, 1H), 7.11 (d, J=7.6 Hz, 1H), 7.02 (s, 2H), 6.70 (d, J=7.6 Hz, 1H), 4.07 (s, 3H), 3.90 (q, J=7.2 Hz, 2H), 3.67 (s, 3H), 1.31 (t, J=7.2 Hz, 3H).

Example 34

Synthesis of 3,5-dichloro-N-(1-ethyl-2-oxo-1,2-dihydrobenzo[cd]indol-6-yl)benzenesulfonamide

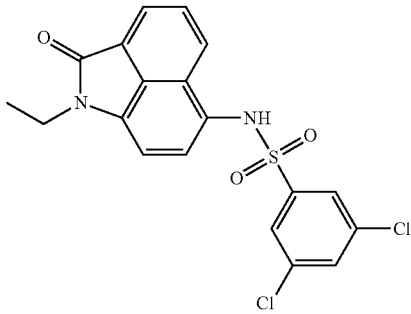 [SMILES: CCN1C(=O)c2cccc3c(NS(=O)(=O)c4cc(Cl)cc(Cl)c4)ccc1c23]

The synthesis can refer to Example 1. ¹H NMR (400 MHz, d-DMSO) δ 10.52 (s, 1H), 8.05 (t, J=8.0 Hz, 2H), 7.93 (s, 1H), 7.76 (t, J=7.6 Hz, 1H), 7.60 (s, 2H), 7.29-6.97 (m, 2H), 3.88 (q, J=7.2 Hz, 2H), 1.23 (t, J=7.2 Hz, 3H).

Example 35

Synthesis of 2,3-dichloro-N-(1-ethyl-2-oxo-1,2-dihydrobenzo[cd]indol-6-yl)benzenesulfonamide

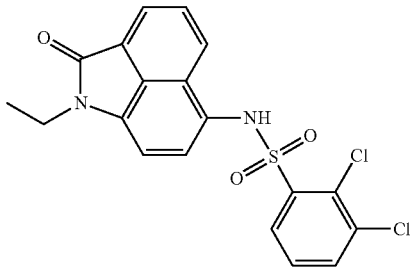 [SMILES: CCN1C(=O)c2cccc3c(NS(=O)(=O)c4cccc(Cl)c4Cl)ccc1c23]

The synthesis can refer to Example 1. ¹H NMR (400 MHz, d-DMSO) δ 10.77 (s, 1H), 8.24 (d, J=8.0 Hz, 1H), 8.03 (d, J=6.8 Hz, 1H), 7.89 (d, J=8.0 Hz, 1H), 7.80 (dd, J=7.6, 4.0 Hz, 2H), 7.42 (t, J=8.0 Hz, 1H), 7.18 (d, J=7.6 Hz, 1H), 7.09 (d, J=7.6 Hz, 1H), 3.85 (q, J=7.2 Hz, 2H), 1.21 (t, J=7.2 Hz, 3H).

Example 36

Synthesis of methyl4-((N-(1-ethyl-2-oxo-1,2-dihydrobenzo[cd]indol-6-yl)sulfamoyl)methyl)benzoate

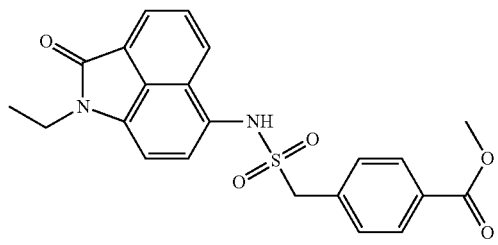 [SMILES: CCN1C(=O)c2cccc3c(NS(=O)(=O)Cc4ccc(C(=O)OC)cc4)ccc1c23]

The synthesis can refer to Example 1. $^1$H NMR (400 MHz, CDCl$_3$) δ 8.10 (d, J=6.8 Hz, 1H), 7.95 (t, J=8.4 Hz, 3H), 7.74 (t, J=7.6 Hz, 1H), 7.52 (d, J=7.6 Hz, 1H), 7.36 (d, J=8.0 Hz, 2H), 6.87 (d, J=7.6 Hz, 1H), 6.82 (s, 1H), 4.43 (s, 2H), 3.97 (q, J=7.2 Hz, 2H), 3.91 (s, 3H), 1.38 (t, J=7.2 Hz, 3H).

Example 37

Synthesis of 4-((N-(1-ethyl-2-oxo-1,2-dihydrobenzo[cd]indol-6-yl)sulfamoyl)methyl)benzoic acid

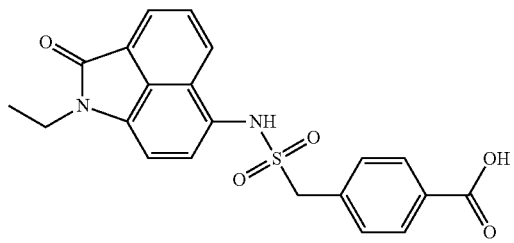 [SMILES: CCN1C(=O)c2cccc3c(NS(=O)(=O)Cc4ccc(C(=O)O)cc4)ccc1c23]

The synthesis can refer to Example 1. $^1$H NMR (400 MHz, d-DMSO) δ 12.92 (s, 1H), 9.96 (s, 1H), 8.31 (d, J=8.4 Hz, 1H), 8.08 (d, J=6.8 Hz, 1H), 7.86-7.80 (m, 3H), 7.48 (d, J=7.6 Hz, 1H), 7.43 (d, J=8.0 Hz, 2H), 7.19 (d, J=7.6 Hz, 1H), 4.59 (s, 2H), 3.92 (q, J=6.8 Hz, 2H), 1.27 (t, J=7.2 Hz, 3H).

Example 38

Synthesis of N-(1-ethyl-2-oxo-1,2-dihydrobenzo[cd]indol-6-yl)-1-(3-fluorophenyl)methanesulfonamide

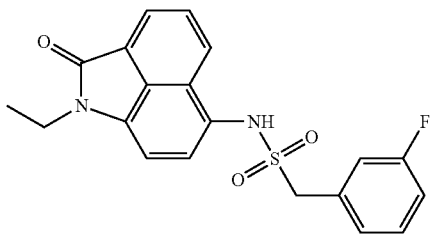 [SMILES: CCN1C(=O)c2cccc3c(NS(=O)(=O)Cc4cccc(F)c4)ccc1c23]

The synthesis can refer to Example 1. $^1$H NMR (400 MHz, CDCl$_3$) δ 8.10 (d, J=7.2 Hz, 1H), 7.96 (d, J=8.4 Hz, 1H), 7.74 (t, J=7.6 Hz, 1H), 7.52 (d, J=7.6 Hz, 1H), 7.32-7.13 (m, 2H), 7.04 (t, J=10.4 Hz, 3H), 6.91-6.66 (m, 2H), 4.37 (s, 2H), 3.98 (q, J=7.2 Hz, 2H), 1.38 (t, J=7.2 Hz, 3H).

Example 39

Synthesis of methyl3-((N-(1-ethyl-2-oxo-1,2-dihydrobenzo[cd]indol-6-yl)sulfamoyl)methyl)benzoate

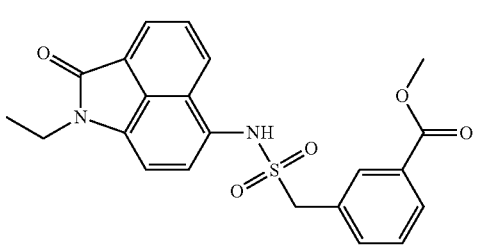 [SMILES: CCN1C(=O)c2cccc3c(NS(=O)(=O)Cc4cccc(C(=O)OC)c4)ccc1c23]

The synthesis can refer to Example 1. $^1$H NMR (400 MHz, d-DMSO) δ 9.94 (s, 1H), 8.27 (d, J=8.4 Hz, 1H), 8.07 (d, J=6.8 Hz, 1H), 7.88 (d, J=7.8 Hz, 1H), 7.86-7.82 (m, 2H), 7.60 (d, J=7.6 Hz, 1H), 7.51-7.35 (m, 2H), 7.17 (d, J=7.6 Hz, 1H), 4.61 (s, 2H), 3.92 (d, J=7.2 Hz, 2H), 3.79 (s, 3H), 1.27 (t, J=7.2 Hz, 3H).

Example 40

Synthesis of N-(1-ethyl-2-oxo-1,2-dihydrobenzo[cd]indol-6-yl)-1-(4-(trifluoromethyl)phenyl)methanesulfonamide

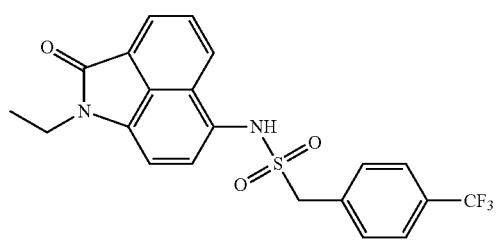 [SMILES: CCN1C(=O)c2cccc3c(NS(=O)(=O)Cc4ccc(C(F)(F)F)cc4)ccc1c23]

The synthesis can refer to Example 1. $^1$H NMR (400 MHz, CDCl$_3$) δ 8.09 (d, J=6.8 Hz, 1H), 7.97 (d, J=8.0 Hz, 1H), 7.73 (t, J=7.6 Hz, 1H), 7.51 (t, J=6.4 Hz, 3H), 7.40 (d, J=7.6 Hz, 2H), 6.94 (s, 1H), 6.86 (d, J=7.6 Hz, 1H), 4.44 (s, 2H), 3.97 (q, J=7.2 Hz, 2H), 1.38 (t, J=7.2 Hz, 3H).

Example 41

Synthesis of N-(1-ethyl-2-oxo-1,2-dihydrobenzo[cd]indol-6-yl)-1-(p-tolyl)methanesulfonamide

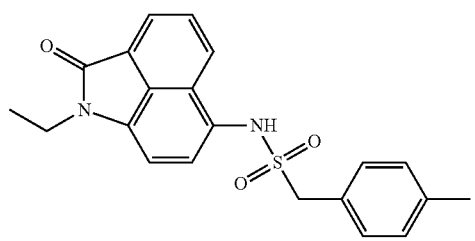 [SMILES: CCN1C(=O)c2cccc3c(NS(=O)(=O)Cc4ccc(C)cc4)ccc1c23]

The synthesis can refer to Example 1. ¹H NMR (400 MHz, d-DMSO) δ 9.84 (s, 1H), 8.32 (d, J=8.4 Hz, 1H), 8.07 (d, J=6.8 Hz, 1H), 7.82 (t, J=7.6 Hz, 1H), 7.47 (d, J=7.6 Hz, 1H), 7.20-7.18 (m, 3H), 7.11 (d, J=7.6 Hz, 2H), 4.42 (s, 2H), 3.92 (q, J=7.2 Hz, 2H), 2.28 (s, 3H), 1.27 (t, J=7.2 Hz, 3H).

Example 42

Synthesis of N-(1-ethyl-2-oxo-1,2-dihydrobenzo[cd]indol-6-yl)-1-(2-fluorophenyl)methanesulfonamide

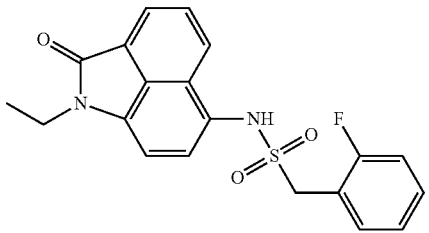 [SMILES: CCN1C(=O)c2cccc3c(NS(=O)(=O)Cc4ccccc4F)ccc1c23]

The synthesis can refer to Example 1. ¹H NMR (400 MHz, d-DMSO) δ 10.03 (s, 1H), 8.34 (d, J=8.4 Hz, 1H), 8.08 (d, J=6.8 Hz, 1H), 7.84 (t, J=7.6 Hz, 1H), 7.50 (d, J=7.6 Hz, 1H), 7.41 (t, J=7.2 Hz, 2H), 7.20-7.16 (m, 3H), 4.53 (s, 2H), 3.93 (q, J=7.2 Hz, 2H), 1.27 (t, J=7.2 Hz, 3H).

Example 43

Synthesis of 1-(4-chlorophenyl)-N-(1-ethyl-2-oxo-1,2-dihydrobenzo[cd]indol-6-yl)methanesulfonamide

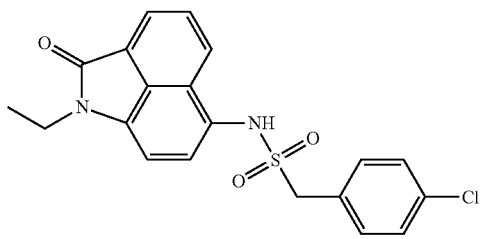 [SMILES: CCN1C(=O)c2cccc3c(NS(=O)(=O)Cc4ccc(Cl)cc4)ccc1c23]

The synthesis can refer to Example 1. ¹H NMR (400 MHz, d-DMSO) δ 9.92 (s, 1H), 8.31 (d, J=8.4 Hz, 1H), 8.07 (d, J=6.8 Hz, 1H), 7.83 (t, J=7.6 Hz, 1H), 7.48 (d, J=7.6 Hz, 1H), 7.35 (q, J=8.4 Hz, 4H), 7.18 (d, J=7.6 Hz, 1H), 4.51 (s, 2H), 3.92 (q, J=7.2 Hz, 2H), 1.27 (t, J=7.2 Hz, 3H).

Example 44

Synthesis of 1-(4-cyanophenyl)-N-(1-ethyl-2-oxo-1,2-dihydrobenzo[cd]indol-6-yl)methanesulfonamide

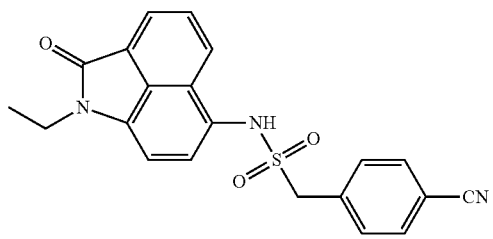 [SMILES: CCN1C(=O)c2cccc3c(NS(=O)(=O)Cc4ccc(C#N)cc4)ccc1c23]

The synthesis can refer to Example 1. ¹H NMR (400 MHz, CDCl₃) δ 10.01 (s, 1H), 8.29 (d, J=8.0 Hz, 1H), 8.08 (d, J=6.8 Hz, 1H), 7.83 (t, J=7.6 Hz, 1H), 7.78 (d, J=8.0 Hz, 2H), 7.52-7.46 (m, 3H), 7.19 (d, J=7.6 Hz, 1H), 4.64 (s, 2H), 3.92 (q, J=6.8 Hz, 2H), 1.27 (t, J=7.2 Hz, 3H).

Example 45

Synthesis of N-(1-ethyl-2-oxo-1,2-dihydrobenzo[cd]indol-6-yl)-1-(4-fluorophenyl)methanesulfonamide

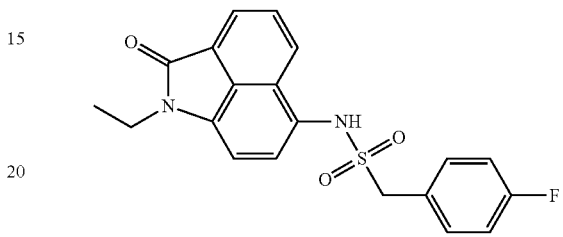

The synthesis can refer to Example 1. ¹H NMR (400 MHz, CDCl₃) δ 8.10 (d, J=7.2 Hz, 1H), 7.96 (d, J=8.4 Hz, 1H), 7.84-7.68 (m, 1H), 7.51 (d, J=7.6 Hz, 1H), 7.25 (d, J=9.2 Hz, 1H), 6.98 (t, J=8.4 Hz, 2H), 6.87 (d, J=7.6 Hz, 1H), 6.71 (s, 1H), 4.36 (s, 2H), 3.98 (q, J=7.2 Hz, 2H), 1.39 (t, J=7.2 Hz, 3H).

The synthesis of formula II:

Example 46

Synthesis of N-(1-ethyl-2-oxo-1,2-dihydrobenzo[cd]indol-6-yl)-4-fluorobenzamide

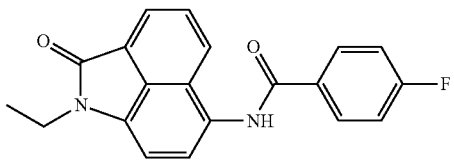 [SMILES: CCN1C(=O)c2cccc3c(NC(=O)c4ccc(F)cc4)ccc1c23]

6-amino-1-ethylbenzo[cd]indol-2(1H)-one can refer to Example 1.

A reaction mixture of 6-amino-1-ethylbenzo[cd]indol-2(1H)-one (100 mg, 0.47 mmol) and 4-fluorobenzoic acid (98 mg, 0.7 mmol) in DCM (20 mL) was stirred at rt for 5 min. HATU (269 mg, 0.71 mmol) and DIPEA (183 mg, 1.41 mmol) was added to the reaction mixture. After the reaction was completed, the reaction mixture was stirred at rt for overnight. The reaction mixture was extracted with ethyl acetate (150 mL×2). The organic layer was washed with brine and dried over Na₂SO₄. The solid was filtered off, and the filtrate was concentrated under reduced pressure. The resulting crude product was purified by silica gel chromatography with petroleum ether/ethyl acetate (3/1, v/v) to yield N-(1-ethyl-2-oxo-1,2-dihydrobenzo[cd]indol-6-yl)-4-fluorobenzamide (90 mg, 57%) as a yellow solid. ¹H NMR (400 MHz, CDCl₃) δ 8.20 (s, 1H), 8.03-7.96 (m, 4H), 7.81 (d, J=7.6 Hz, 1H), 7.68 (t, J=7.6 Hz, 1H), 7.20 (t, J=8.4 Hz, 2H), 6.87 (d, J=7.6 Hz, 1H), 3.96 (q, J=7.2 Hz, 2H), 1.37 (t, J=7.2 Hz, 3H).

Example 47

Synthesis of 2-(4-chlorophenyl)-N-(1-ethyl-2-oxo-1,2-dihydrobenzo[cd]indol-6-yl)acetamide

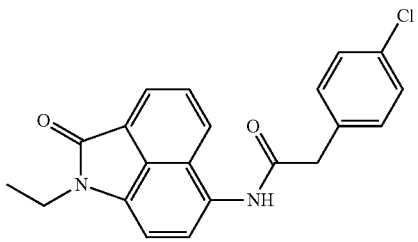 [SMILES: CCN1C(=O)c2cccc3c(NC(=O)Cc4ccc(Cl)cc4)ccc1c23]

The synthesis can refer to Example 46. $^1$H NMR (400 MHz, d-DMSO) δ 10.23 (s, 1H), 8.28 (d, J=8.0 Hz, 1H), 8.06 (d, J=6.8 Hz, 1H), 7.83 (t, J=7.6 Hz, 1H), 7.76 (d, J=7.6 Hz, 1H), 7.61-7.26 (m, 4H), 7.16 (d, J=7.6 Hz, 1H), 3.90 (q, J=7.2 Hz, 2H), 3.82 (s, 2H), 1.25 (t, J=7.2 Hz, 3H).

Example 48

Synthesis of 2-(3,4-dimethoxyphenyl)-N-(1-ethyl-2-oxo-1,2-dihydrobenzo[cd]indol-6-yl)acetamide

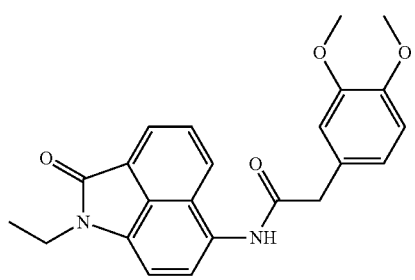 [SMILES: CCN1C(=O)c2cccc3c(NC(=O)Cc4ccc(OC)c(OC)c4)ccc1c23]

The synthesis can refer to Example 46. $^1$H NMR (400 MHz, CDCl$_3$) δ 8.01 (d, J=6.8 Hz, 1H), 7.87 (d, J=7.6 Hz, 1H), 7.62 (t, J=7.6 Hz, 1H), 7.55 (s, 1H), 7.50 (d, J=8.0 Hz, 1H), 6.98-6.94 (m, 3H), 6.85 (d, J=7.6 Hz, 1H), 3.96-3.92 (m, 8H), 3.82 (s, 2H), 1.34 (t, J=7.2 Hz, 3H).

Example 49

Synthesis of 2-(2,4-dichlorophenyl)-N-(1-ethyl-2-oxo-1,2-dihydrobenzo[cd]indol-6-yl)acetamide

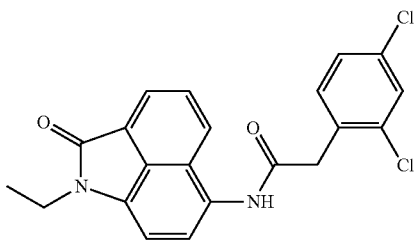 [SMILES: CCN1C(=O)c2cccc3c(NC(=O)Cc4ccc(Cl)cc4Cl)ccc1c23]

The synthesis can refer to Example 46. $^1$H NMR (400 MHz, d-DMSO) δ 10.29 (s, 1H), 8.33 (d, J=8.0 Hz, 1H), 8.07 (d, J=6.8 Hz, 1H), 7.84 (t, J=7.6 Hz, 1H), 7.74 (d, J=7.6 Hz, 1H), 7.63 (s, 1H), 7.52 (d, J=8.4 Hz, 1H), 7.43 (d, J=8.4 Hz, 1H), 7.17 (d, J=7.6 Hz, 1H), 4.01 (s, 2H), 3.91 (q, J=7.2 Hz, 2H), 1.26 (t, J=7.2 Hz, 3H).

Example 50

Synthesis of N-(1-ethyl-2-oxo-1,2-dihydrobenzo[cd]indol-6-yl)-3-phenylpropanamide

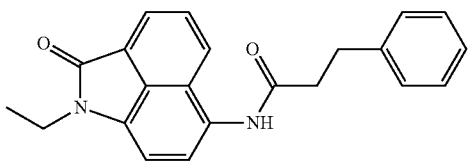 [SMILES: CCN1C(=O)c2cccc3c(NC(=O)CCc4ccccc4)ccc1c23]

The synthesis can refer to Example 46. $^1$H NMR (400 MHz, d-DMSO) δ 9.95 (s, 1H), 8.11 (d, J=8.4 Hz, 1H), 8.05 (d, J=7.2 Hz, 1H), 7.86-7.73 (m, 1H), 7.71 (d, J=7.6 Hz, 1H), 7.31 (d, J=4.0 Hz, 3H), 7.23 (s, 1H), 7.16 (d, J=7.6 Hz, 1H), 3.91 (q, J=7.2 Hz, 2H), 2.98 (t, J=7.6 Hz, 2H), 2.79 (t, J=7.6 Hz, 2H), 1.26 (t, J=7.2 Hz, 3H).

Example 51

Synthesis of N-(1-ethyl-2-oxo-1,2-dihydrobenzo[cd]indol-6-yl)-4,4,4-trifluorobutanamide

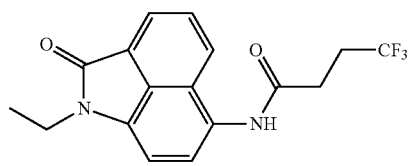 [SMILES: CCN1C(=O)c2cccc3c(NC(=O)CCC(F)(F)F)ccc1c23]

The synthesis can refer to Example 46. $^1$H NMR (400 MHz, d-DMSO) δ 10.14 (s, 1H), 8.32 (d, J=8.4 Hz, 1H), 8.07 (d, J=6.8 Hz, 1H), 7.83 (t, J=7.6 Hz, 1H), 7.77 (d, J=7.6 Hz, 1H), 7.18 (d, J=7.6 Hz, 1H), 3.91 (q, J=7.2 Hz, 2H), 2.88-2.71 (m, 2H), 2.71-2.51 (m, 2H), 1.26 (t, J=7.2 Hz, 3H).

Example 52

Synthesis of N-(1-ethyl-2-oxo-1,2-dihydrobenzo[cd]indol-6-yl)propionamide

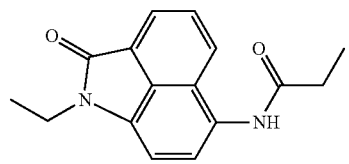 [SMILES: CCC(=O)Nc1ccc2c3c(cccc13)C(=O)N2CC]

The synthesis can refer to Example 46. $^1$H NMR (400 MHz, d-DMSO) δ 9.92 (s, 1H), 8.30 (d, J=8.4 Hz, 1H), 8.06 (d, J=6.8 Hz, 1H), 7.89-7.62 (m, 2H), 7.16 (d, J=7.6 Hz, 1H), 3.91 (q, J=7.2 Hz, 2H), 2.46 (q, J=7.6 Hz, 2H), 1.26 (t, J=7.2 Hz, 3H), 1.16 (t, J=7.6 Hz, 3H).

Example 53

Synthesis of 4-chloro-N-(1-ethyl-2-oxo-1,2-dihydrobenzo[cd]indol-6-yl)benzamide

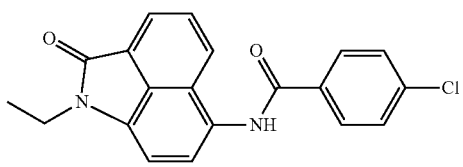

The synthesis can refer to Example 46. $^1$H NMR (400 MHz, d-DMSO) δ 10.55 (s, 1H), 8.20 (d, J=8.0 Hz, 1H), 8.09 (t, J=8.8 Hz, 3H), 7.81 (t, J=7.6 Hz, 1H), 7.65 (d, J=8.4 Hz, 3H), 7.23 (d, J=7.6 Hz, 1H), 3.94 (q, J=7.2 Hz, 2H), 1.29 (t, J=7.2 Hz, 3H).

Example 54

Synthesis of N-(1-ethyl-2-oxo-1,2-dihydrobenzo[cd]indol-6-yl)-2-(p-tolyl)acetamide

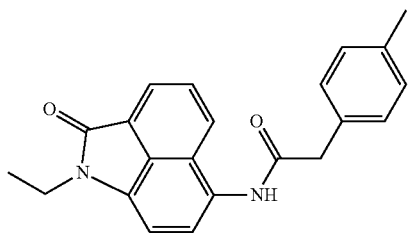 [SMILES: CCN1C(=O)c2cccc3c(NC(=O)Cc4ccc(C)cc4)ccc1c23]

The synthesis can refer to Example 46. $^1$H NMR (400 MHz, d-DMSO) δ 10.19 (s, 1H), 8.27 (d, J=8.0 Hz, 1H), 8.06 (d, J=6.8 Hz, 1H), 7.82 (t, J=7.6 Hz, 1H), 7.75 (d, J=7.6 Hz, 1H), 7.30 (d, J=7.6 Hz, 2H), 7.16 (d, J=7.6 Hz, 3H), 3.90 (q, J=7.2 Hz, 2H), 3.75 (s, 2H), 2.29 (s, 3H), 1.25 (t, J=7.2 Hz, 3H).

Example 55

Synthesis of (E)-N-(1-ethyl-2-oxo-1,2-dihydrobenzo[cd]indol-6-yl)-3-(furan-2-yl)acrylamide

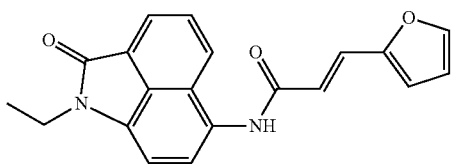 [SMILES: CCN1C(=O)c2cccc3c(NC(=O)/C=C/c4ccco4)ccc1c23]

The synthesis can refer to Example 46. $^1$H NMR (400 MHz, d-DMSO) δ 10.24 (s, 1H), 8.43 (d, J=8.0 Hz, 1H), 8.07 (t, J=7.6 Hz, 2H), 7.84 (t, J=11.2 Hz, 2H), 7.45 (d, J=11.2 Hz, 1H), 7.20 (d, J=7.6 Hz, 1H), 7.04-6.75 (m, 2H), 6.64 (s, 1H), 3.92 (q, J=6.8 Hz, 2H), 1.27 (t, J=7.2 Hz, 3H).

The synthesis of formula III:

Example 56

Synthesis of I-ethyl-6-((3-phenylpropyl)amino)benzo[cd]indol-2(1H)-one

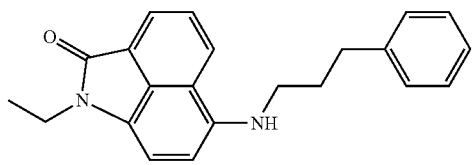 [SMILES: CCN1C(=O)c2cccc3c(NCCCc4ccccc4)ccc1c23]

6-amino-1-ethylbenzo[cd]indol-2(1H)-one can refer to Example 1.

A reaction mixture of 6-amino-1-ethylbenzo[cd]indol-2 (1H)-one (100 mg, 0.47 mmol) and (3-chloropropyl)benzene (73 mg, 0.47 mmol) in CH$_3$CN (20 mL) was stirred at rt. K$_2$CO$_3$ (195 mg, 1.41 mmol) was added to the reaction mixture, and stirred at 70° C. for overnight. The reaction mixture was extracted with ethyl acetate (150 mL×2). The organic layer was washed with brine and dried over Na$_2$SO$_4$. The solid was filtered off, and the filtrate was concentrated under reduced pressure. The resulting crude product was purified by silica gel chromatography with petroleum ether/ethyl acetate (5/1, v/v) to yield 1-ethyl-6-((3-phenylpropyl)amino)benzo[cd]indol-2(1H)-one (60 mg, 38%) as a yellow solid. $^1$H NMR (400 MHz, CDCl$_3$) δ 8.06 (d, J=7.2 Hz, 11H), 7.84 (d, J=8.0 Hz, 1H), 7.63 (t, J=7.6 Hz, 1H), 7.32 (t, J=7.6 Hz, 2H), 7.26-7.04 (m, 3H), 6.77 (d, J=7.6 Hz, 1H), 6.34 (d, J=7.2 Hz, 1H), 4.24 (s, 1H), 3.94 (q, J=7.2 Hz, 2H), 3.30 (t, J=6.8 Hz, 2H), 2.83 (t, J=7.2 Hz, 2H), 2.21-2.03 (m, 2H), 1.36 (t, J=7.2 Hz, 3H).

Example 56

Synthesis of 1-ethyl-6-((3-morpholinopropyl)amino)benzo[cd]indol-2(1H)-one

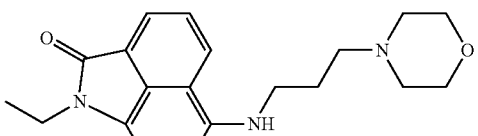

The synthesis can refer to Example 56. $^1$H NMR (400 MHz, CDCl$_3$) δ 8.07 (d, J=7.6 Hz, 2H), 7.66 (t, J=7.6 Hz, 1H), 6.79 (d, J=7.6 Hz, 1H), 6.35 (d, J=7.6 Hz, 1H), 5.81 (s, 1H), 3.95 (q, J=7.2 Hz, 2H), 3.82 (t, J=4.4 Hz, 4H), 3.35 (t, J=6.0 Hz, 2H), 2.60-2.54 (m, 6H), 2.02-1.87 (m, 2H), 1.36 (t, J=7.2 Hz, 3H).

Example 58

Synthesis of 1-ethyl-6-((4-methoxybenzyl)amino)
benzo[cd]indol-2(1H)-one

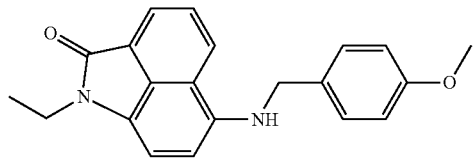 [SMILES: CCN1C(=O)c2cccc3c(NCc4ccc(OC)cc4)ccc1c23]

The synthesis can refer to Example 56. $^1$H NMR (400 MHz, d-DMSO) δ 8.51 (d, J=8.0 Hz, 1H), 7.98 (d, J=7.2 Hz, 1H), 7.71 (t, J=7.6 Hz, 1H), 7.33 (d, J=8.4 Hz, 2H), 7.05 (s, 1H), 6.88 (d, J=8.4 Hz, 3H), 6.21 (d, J=7.6 Hz, 1H), 4.40 (d, J=4.4 Hz, 2H), 3.82 (q, J=7.2 Hz, 2H), 3.70 (d, J=8.8 Hz, 3H), 1.20 (t, J=7.2 Hz, 3H).

Example 59

Synthesis of 1-ethyl-6-((4-methylbenzyl)amino)
benzo[cd]indol-2(1H)-one

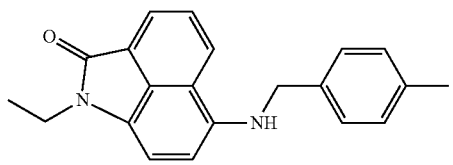 [SMILES: CCN1C(=O)c2cccc3c(NCc4ccc(C)cc4)ccc1c23]

The synthesis can refer to Example 56. $^1$H NMR (400 MHz, d-DMSO) δ 8.52 (d, J=8.0 Hz, 1H), 7.99 (d, J=6.8 Hz, 1H), 7.71 (t, J=7.6 Hz, 1H), 7.29 (d, J=7.6 Hz, 2H), 7.12 (d, J=7.6 Hz, 3H), 6.87 (d, J=7.6 Hz, 1H), 6.17 (d, J=7.6 Hz, 1H), 4.42 (s, 2H), 3.81 (q, J=7.2 Hz, 2H), 2.26 (s, 3H), 1.20 (t, J=7.2 Hz, 3H).

Example 60

Synthesis of 1-ethyl-6-((4-(trifluoromethyl)benzyl)
amino)benzo[cd]indol-2(1H)-one

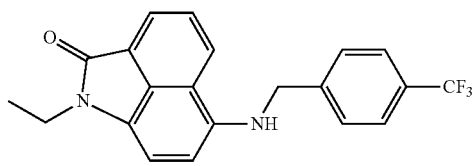

The synthesis can refer to Example 56. $^1$H NMR (400 MHz, d-DMSO) δ 8.52 (d, J=8.0 Hz, 1H), 8.00 (d, J=6.8 Hz, 1H), 7.74 (t, J=7.6 Hz, 1H), 7.69 (d, J=8.0 Hz, 2H), 7.63 (d, J=8.0 Hz, 2H), 7.26 (s, 1H), 6.87 (d, J=7.6 Hz, 1H), 6.14 (d, J=7.6 Hz, 1H), 4.58 (d, J=5.2 Hz, 2H), 3.81 (q, J=7.2 Hz, 2H), 1.20 (t, J=7.2 Hz, 3H).

Example 61

Synthesis of 6-((4-chlorobenzyl)amino)-1-ethyl-
benzo[cd]indol-2(1H)-one

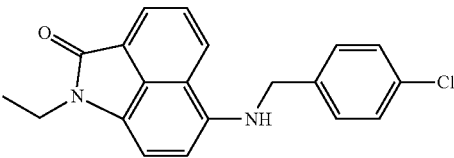 [SMILES: CCN1C(=O)c2cccc3c(NCc4ccc(Cl)cc4)ccc1c23]

The synthesis can refer to Example 56. $^1$H NMR (400 MHz, d-DMSO) δ 8.51 (d, J=8.4 Hz, 1H), 8.00 (d, J=6.8 Hz, 1H), 7.73 (t, J=7.6 Hz, 1H), 7.43 (d, J=8.4 Hz, 2H), 7.37 (d, J=8.4 Hz, 2H), 7.18 (t, J=6.0 Hz, 1H), 6.88 (d, J=7.6 Hz, 1H), 6.15 (d, J=7.6 Hz, 1H), 4.47 (d, J=6.0 Hz, 2H), 3.82 (q, J=7.2 Hz, 2H), 1.20 (t, J=7.2 Hz, 3H).

Example 62

Synthesis of 1-ethyl-6-((4-fluorobenzyl)amino)
benzo[cd]indol-2(1H)-one

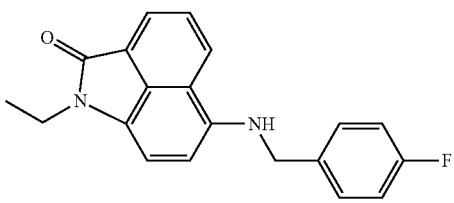 [SMILES: CCN1C(=O)c2cccc3c(NCc4ccc(F)cc4)ccc1c23]

The synthesis can refer to Example 56. $^1$H NMR (400 MHz, CDCl$_3$) δ 8.07 (d, J=7.2 Hz, 1H), 8.00 (d, J=8.2 Hz, 1H), 7.66 (t, J=7.6 Hz, 1H), 7.41 (dd, J=8.4, 5.6 Hz, 2H), 7.06 (t, J=8.4 Hz, 2H), 6.75 (d, J=7.6 Hz, 1H), 6.38 (d, J=7.6 Hz, 1H), 4.66 (s, 1H), 4.45 (s, 2H), 3.94 (q, J=7.2 Hz, 2H), 1.35 (t, J=7.2 Hz, 3H).

The synthesis of formula IV:

Example 63

Synthesis of N-((1-acetylpiperidin-4-yl)methyl)-1-
ethyl-2-oxo-1,2-dihydrobenzo[cd]indole-6-sulfona-
mide

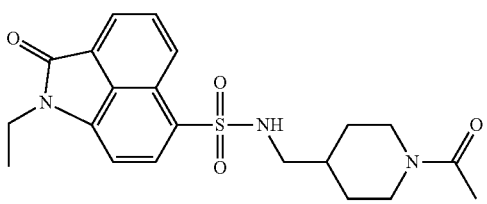 [SMILES: CCN1C(=O)c2cccc3c(S(=O)(=O)NCC4CCN(C(C)=O)CC4)ccc1c23]

The synthesis of 1-ethylbenzo[cd]indol-2(1H)-one can refer to Example 1.

Step 1. Synthesis of 1-ethyl-2-oxo-1,2-dihydrobenzo[cd]indole-6-sulfonyl chloride

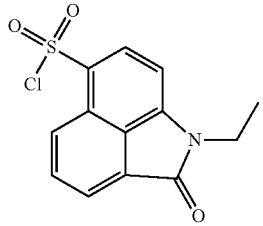 [SMILES: CCN1C(=O)c2cccc3c(S(=O)(=O)Cl)ccc1c23]

To a solution of 1-ethylbenzo[cd]indol-2(1H)-one (6.46 g, 0.03 mol) in chloroform (100 mL) was added batches of chlorosulfonic (11.5 g, 0.1 mol) at 0° C. for 10 min. The reaction mixture was heated at 50° C. for 6 h. The mixture was then poured into ice water and extracted with DCM (150 mL×2). The organic layer was washed with brine and dried over Na₂SO₄. The solid was filtered off, and the filtrate was concentrated under reduced pressure. The resulting crude product was purified by silica gel chromatography with petroleum ether/ethyl acetate (5/1, v/v) to yield 1-ethyl-2-oxo-1,2-dihydrobenzo[cd]indole-6-sulfonyl chloride (5.75 g, 59%) as a yellow solid. MS (ESI), m/z: M⁺ 297.1.

A reaction mixture of 1-ethyl-2-oxo-1,2-dihydrobenzo[cd]indole-6-sulfonyl chloride (100 mg, 0.34 mmol) and 1-(4-(aminomethyl)piperidin-1-yl)ethan-1-one (64 mg, 0.41 mmol) in pyridine (5 mL) was stirred at 80° C. for 1 h. Dilute HCl was added, the aqueous layer was extracted with ethyl acetate (50 mL×3), and the organic layer was washed with water and brine, dried with Na₂SO₄ and evaporated. The residue was purified by silica gel chromatography with petroleum and ether/ethyl acetate (4/1, v/v) to afford N-((1-acetylpiperidin-4-yl)methyl)-1-ethyl-2-oxo-1,2-dihydrobenzo[cd]indole-6-sulfonamide (92 mg, 65%). ¹H-NMR (400 MHz, d-DMSO) δ 8.69 (d, J=8.4 Hz,1H), 8.16 (d, J=6.8 Hz,1H), 8.07 (d, J=7.6 Hz, 1H), 7.96 (t, J=7.2 Hz,1H), 7.86 (t, J=6.0 Hz,1H), 7.31 (d, J=7.6 Hz,1H), 4.24 (d, J=8.0 Hz,1H), 3.93 (q, J=6.8 Hz, 2H), 3.69 (d, J=12.4 Hz, 1H), 2.87 (t, J=13.2 Hz,1H), 2.64 (t, J=6.0 Hz,2H), 2.36 (t, J=12.0 Hz, 1H). 1.92 (s, 3H). 1.56-1.51 (m, 3H), 1.28 (t, J=7.2 Hz, 3H).MS (ESI), m/z: M⁺ 417.0; M⁻ 415.0.

Example 64

Synthesis of N-(1-acetylcyclohexyl)-1-ethyl-2-oxo-1,2-dihydrobenzo[cd]indole-6-sulfonamide

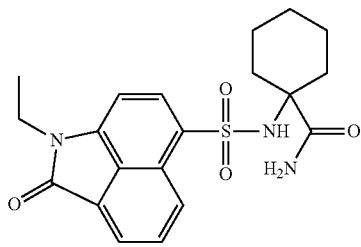 [SMILES: CCN1C(=O)c2cccc3c(S(=O)(=O)NC4(C(N)=O)CCCCC4)ccc1c23]

The synthesis can refer to Example 63. ¹H-NMR (400 MHz, d-DMSO) d 8.58 (d, J=8.4 Hz,1H), 8.15 (d, J=7.2 Hz,1H), 8.09 (d, J=7.6 Hz, 1H), 7.96 (t, J=8.0 Hz, 1H), 7.31 (d, J=7.6 Hz,1H), 3.92 (q, J=6.8 Hz,2H), 3.26-3.21 (m, 4H), 1.25 (t, J=7.2 Hz, 3H), 1.01-0.98 (m, 6H).MS (ESI), m/z: M⁻ 400.8.

Example 65

Synthesis of 1-ethyl-N-((3-isopropyl-4,5-dihydroisoxazol-5-yl)methyl)-2-oxo-1,2-dihydrobenzo[cd]indole-6-sulfonamide

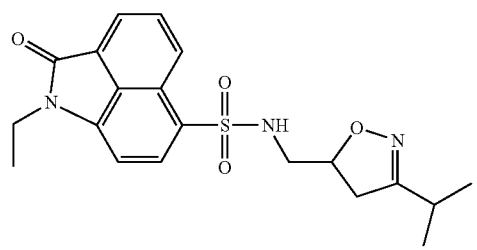 [SMILES: CCN1C(=O)c2cccc3c(S(=O)(=O)NCC4CC(C(C)C)=NO4)ccc1c23]

The synthesis can refer to Example 63. ¹H-NMR (400 MHz, d-DMSO) δ 8.70 (d, J=8.0 Hz,1H), 8.14-8.09 (m, 2H), 8.06 (d, J=7.6 Hz, 1H), 7.94 (t, J=7.6 Hz,1H), 7.29 (d, J=7.2 Hz, 1H), 4.43-4.39 (m,1H), 3.93 (q, J=6.8 Hz, 2H),2.84-2.83 (m,2H), 2.48 (s,3H), 1.26 (t, J=6.8 Hz, 1H), 0.98 (s, 6H). MS (ESI), m/z: M⁻ 400.0.

Example 66

Synthesis of N-((3,5-dimethyl-4,5-dihydroisoxazol-5-yl)methyl)-1-ethyl-2-oxo-1,2-dihydrobenzo[cd]indole-6-sulfonamide

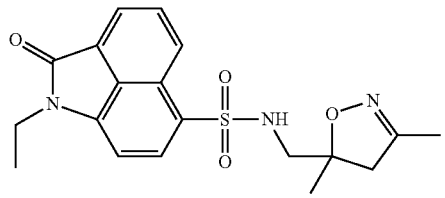 [SMILES: CCN1C(=O)c2cccc3c(S(=O)(=O)NCC4(C)CC(C)=NO4)ccc1c23]

The synthesis can refer to Example 63. ¹H-NMR (400 MHz, d-DMSO) δ 8.72 (d, J=8.4 Hz,1H), 8.15-8.10 (m,2H), 8.07 (d, J=7.6 Hz, 1H), 7.94 (t, J=7.2 Hz,1H), 7.30 (d, J=7.6 Hz,1H), 3.93 (q, J=7.2 Hz, 2H), 2.85-2.82 (m,3H), 2.58 (s, 1H), 1.75 (s, 3H), 1.27-1.22 (m, 4H), 1.17 (s,2H). MS (ESI), m/z: M⁻ 386.0.

Example 67

Synthesis of N-(4-acetylphenyl)-1-ethyl-2-oxo-1,2-dihydrobenzo[cd]indole-6-sulfonamide

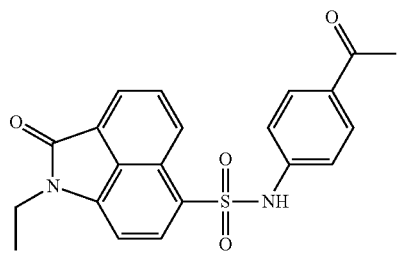 [SMILES: CCN1C(=O)c2cccc3c(S(=O)(=O)Nc4ccc(C(C)=O)cc4)ccc1c23]

The synthesis of 1-ethyl-2-oxo-1,2-dihydrobenzo[cd]indole-6-sulfonyl chloride can refer to Example 63.

A reaction mixture of 1-ethyl-2-oxo-1,2-dihydrobenzo[cd]indole-6-sulfonyl chloride (100 mg, 0.34 mmol) and 1-(4-aminophenyl)ethan-1-one (55 mg, 0.41 mmol) in pyridine (3 mL) was stirred at rt for overnight. Dilute HCl was added, the aqueous layer was extracted with ethyl acetate (50 mL×3), and the organic layer was washed with water and brine, dried with Na$_2$SO$_4$ and evaporated. The residue was purified by silica gel chromatography with petroleum and ether/ethyl acetate (4/1, v/v) to afford N-((1-acetylpiperidin-4-yl)methyl)-1-ethyl-2-oxo-1,2-dihydrobenzo[cd]indole-6-sulfonamide (80 mg, 60%). $^1$H-NMR (400 MHz, d-DMSO) δ10.82(s,1H), 8.69 (d, J=8.4 Hz,1H), 8.19 (d, J=7.6 Hz,1H), 8.09 (d, J=7.2 Hz, 1H), 7.94(t, J=8.0 Hz, 1H), 7.58-7.53 (m,2H),7.31 (d, J=5.6 Hz,2H), 7.25 (d, J=7.6 Hz,1H), 3.86 (q, J=6.8 Hz, 2H), 2.43 (s,3H),1.22 (t, J=6.8 Hz, 3H).MS (ESI), m/z: M+395.0; M$^-$393.0.

Example 68

Synthesis of N-(2-chlorobenzyl)-1-ethyl-2-oxo-1,2-dihydrobenzo[cd]indole-6-sulfonamide

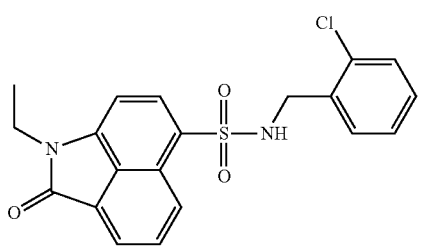 [SMILES: CCN1C(=O)c2cccc3c(S(=O)(=O)NCc4ccccc4Cl)ccc1c23]

The synthesis can refer to Example 63. $^1$H-NMR (400 MHz, d-DMSO) δ 8.68 (d, J=8.0 Hz, 1H), 8.13 (d, J=7.2 Hz, 1H), 8.04 (d, J=7.6 Hz, 1H), 7.92 (t, J=7.2 Hz, 1H), 7.27-7.29 (m, 3H),7.12-7.02 (m, 2H),4.12 (s, 2H), 3.93 (q, J=7.2 Hz, 1H), 1.27 (t, J=7.2 Hz, 3H).MS (ESI), m/z: M$^-$ 399.0.

Example 69

Synthesis of 1-ethyl-N-(2-fluorobenzyl)-2-oxo-1,2-dihydrobenzo[cd]indole-6-sulfonamide

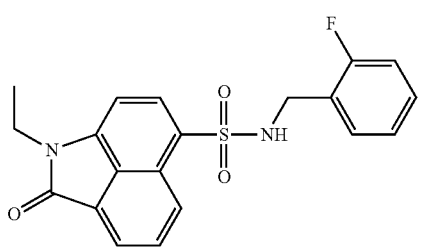

The synthesis can refer to Example 63. $^1$H-NMR (400 MHz, d-DMSO) δ 8.64 (d, J=8.4 Hz,1H), 8.41 (s,1H), 8.12 (d, J=6.8 Hz,1H), 8.03(d, J=8.0 Hz,1H), 7.91 (t, J=7.2 Hz,1H),7.21 (d, J=7.6 Hz,1H),7.15 (t, J=8.0 Hz,1H), 7.07-7.05 (m, 1H),7.91-7.83 (m, 2H), 4.06 (s, 2H), 3.92 (q, J=7.2 Hz, 2H), 1.29 (t,J=7.2 Hz,3H). MS (ESI), m/z: M$^-$ 383.0.

Example 70

Synthesis of N-(1-acetylpiperidin-4-yl)-1-ethyl-2-oxo-1,2-dihydrobenzo[cd]indole-6-sulfonamide

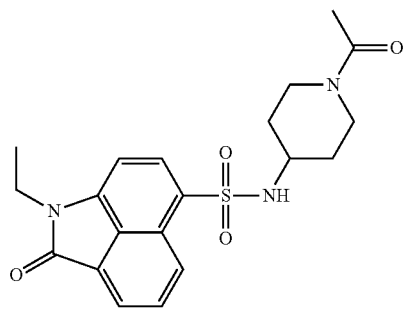 [SMILES: CCN1C(=O)c2cccc3c(S(=O)(=O)NC4CCN(C(C)=O)CC4)ccc1c23]

The synthesis can refer to Example 63. $^1$H-NMR (400 MHz, d-DMSO) δ 8.70 (d, J=8.4 Hz,1H), 8.16-8.11 (m,2H), 8.02 (d, J=7.6 Hz,1H), 7.94(q, J=7.2 Hz,1H), 7.30 (d, J=8.0 Hz,1H),4.01 (q, J=6.8 Hz,1H),3.93 (q, J=7.2 Hz,2H), 3.58 (d, J=14.0 Hz,1H), 3.33-3.19 (m, 1H), 2.97-2.90 (m, 1H), 2.62-2.55 (m, 1H), 1.88 (s,3H),1.49 (d, J=10.0 Hz, 2H), 1.28 (t, J=7.2 Hz, 3H), 1.27-1.22(m, 2H).MS (ESI), m/z: M$^+$ 402.1; M$^-$ 400.1.

Example 71

Synthesis of tert-butyl 4-(1-ethyl-2-oxo-1,2-dihydrobenzo[cd]indole-6-sulfonamido)piperidine-1-carboxylate

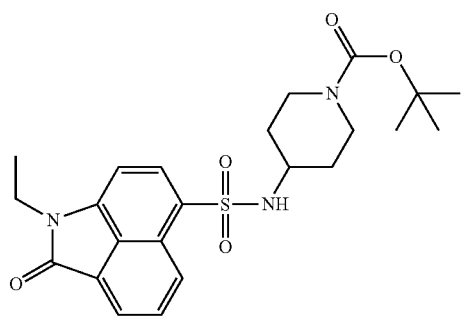 [SMILES: CCN1C(=O)c2cccc3c(S(=O)(=O)NC4CCN(C(=O)OC(C)(C)C)CC4)ccc1c23]

The synthesis can refer to Example 63. $^1$H-NMR (400 MHz, d-DMSO) δ 8.68 (d, J=8.4 Hz,1H), 8.15-8.10 (m, 2H), 7.98-7.92 (m,2H), 7.29(d, J=7.6 Hz, 1H), 3.93 (d, J=7.2 Hz,2H), 3.67-3.64(m,2H),3.18 (s, 1H), 2.69 (s, 2H), 1.47-1.44 (m, 2H), 1.32 (s, 9H), 1.32-1.25 (m, 3H), 1.17-1.51 (m, 2H).MS (ESI), m/z: M$^-$ 458.0.

Example 72

Synthesis of N-cyclopentyl-1-ethyl-2-oxo-1,2-dihydrobenzo[cd]indole-6-sulfonamide

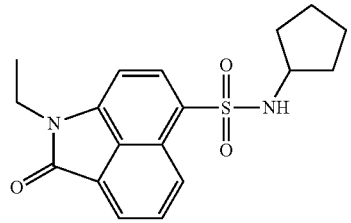 [SMILES: CCN1C(=O)c2cccc3c(S(=O)(=O)NC4CCCC4)ccc1c23]

The synthesis can refer to Example 63. $^1$H-NMR (400 MHz, d-DMSO) δ 8.72 (d, J=8.4 Hz,1H), 8.14 (d, J=6.8 Hz,1H), 8.09 (d, J=7.6 Hz,1H), 7.95 (t, J=7.6 Hz,1H), 7.80 (d, J=7.2 Hz,1H), 7.26 (d, J=7.6 Hz,1H), 3.95 (q, J=7.2 Hz, 2H), 3.44 (q, J=6.4 Hz,1H), 1.51-1.46 (m, 4H), 1.28-1.22 (m, 7H). MS (ESI), m/z: M⁻ 343.0.

Example 73

Synthesis of ethyl 1-((1-ethyl-2-oxo-1,2-dihydrobenzo[cd]indole-6-sulfonamido)methyl)cyclopentanecarboxylate

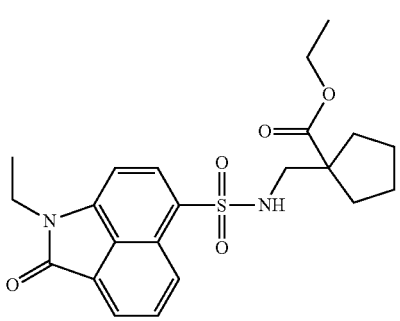 [SMILES: CCOC(=O)C1(CNS(=O)(=O)c2ccc3c4c(cccc24)C(=O)N3CC)CCCC1]

The synthesis can refer to Example 63. $^1$H-NMR (400 MHz, d-DMSO) δ 8.63 (d, J=8.4 Hz, 1H), 8.17 (d, J=7.6 Hz, 1H), 8.11 (d, J=7.2 Hz, 1H), 7.86(t, J=8.0 Hz, 1H), 6.93 (d, J=7.6 Hz, 1H), 5.36 (t, J=6.8 Hz, 1H), 4.04-3.96(m, 4H), 2.92 (d, J=7.2 Hz,2H), 1.93-1.89 (m, 2H), 1.71 (s,2H), 1.58-1.54 (m, 6H),1.39 (t, J=7.2 Hz, 3H), 1.16 (t, J=7.2 Hz, 3H). MS (ESI), m/z: M⁻ 429.0.

Example 74

Synthesis of 1-((1-ethyl-2-oxo-1,2-dihydrobenzo[cd]indole-6-sulfonamido)methyl)cyclopentanecarboxylic acid

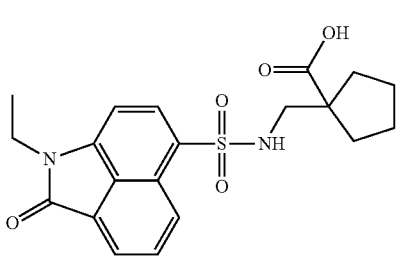 [SMILES: CCN1C(=O)c2cccc3c(S(=O)(=O)NCC4(C(=O)O)CCCC4)ccc1c23]

The synthesis of ethyl 1-((1-ethyl-2-oxo-1,2-dihydrobenzo[cd]indole-6-sulfonamido)methyl)cyclopentanecarboxylate can refer to Example 73.

Ethyl1-((1-ethyl-2-oxo-1,2-dihydrobenzo[cd]indole-6-sulfonamido)methyl)cyclopentanecarboxylate (100 mg, 0.23 mmol) was dissolved in THF (5 mL) and 2 mol/L NaOH aqueous solution (5 mL). The mixture was stirred at room temperature for 2 h. The solvent w as removed and diluted hydrochloric acid was added dropwise, and a yellow precipitate was formed. The precipitate was collected by filtration and washed with water (10 mL×2). The resulting crude product was purified by recrystallization with petroleum and ether/ethyl acetate to afford 1-((1-ethyl-2-oxo-1,2-dihydrobenzo[cd]indole-6-sulfonamido)methyl)cyclopentanecarboxylic acid (86 mg, 93%) as a yellow solid. $^1$H-NMR (400 MHz, d-DMSO) δ 8.63 (d, J=8.4 Hz, 1H), 8.17 (d, J=7.6 Hz, 1H), 8.11 (d, J=7.2 Hz, 1H), 7.86(t, J=8.0 Hz, 1H), 6.93 (d, J=7.6 Hz, 1H), 5.36 (t, J=6.8 Hz, 1H), 3.92 (m, 3H), 2.83 (s, 2H), 1.81 (m, 2H), 1.45 (m,6H), 1.25 (m, 4H).

Example 75

Synthesis of N-(4-(1-ethyl-2-oxo-1,2-dihydrobenzo[cd]indole-6-sulfonamido)phenyl)acetamide

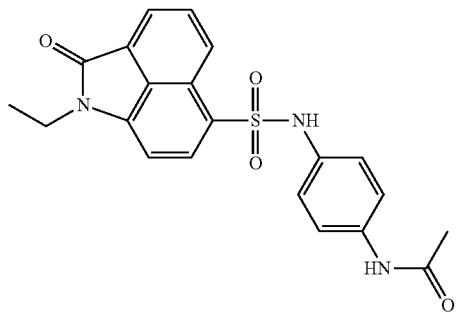 [SMILES: CCN1C(=O)c2cccc3c(S(=O)(=O)Nc4ccc(NC(C)=O)cc4)ccc1c23]

The synthesis can refer to Example 67. $^1$H NMR (400 MHz, d-DMSO) δ 10.33 (s, 1H), 9.79 (s, 1H), 8.68 (d, J=8.0 Hz, 1H), 8.10 (dd, J=14.4, 6.8 Hz, 2H), 7.92 (t, J=7.2 Hz, 1H), 7.34 (d, J=7.6 Hz, 2H), 7.23 (d, J=7.6 Hz, 1H), 6.94 (d, J=7.6 Hz, 2H), 3.88 (d, J=6.8 Hz, 2H), 1.95 (s, 3H), 1.23 (t, J=7.2 Hz, 3H).

Example 76

Synthesis of 2-(1-ethyl-2-oxo-1,2-dihydrobenzo[cd]indole-6-sulfonamido)benzoic acid

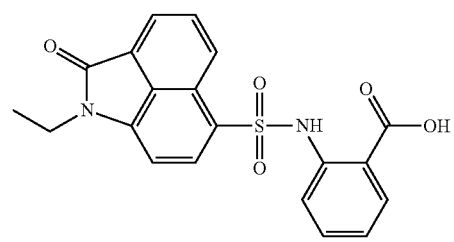 [SMILES: CCN1C(=O)c2cccc3c(S(=O)(=O)Nc4ccccc4C(=O)O)ccc1c23]

The synthesis can refer to Example 74. $^1$H NMR (400 MHz, d-DMSO) δ 11.96 (s, 1H), 8.52 (d, J=8.4 Hz, 1H), 8.26 (d, J=7.6 Hz, 1H), 8.13 (d, J=7.2 Hz, 1H), 8.02-7.84 (m, 1H), 7.80 (d, J=7.2 Hz, 1H), 7.63-7.41 (m, 2H), 7.28 (d, J=7.6 Hz, 1H), 7.02 (t, J=7.6 Hz, 1H), 3.89 (q, J=7.2 Hz, 2H), 1.23 (t, J=7.2 Hz, 3H).

Example 77

Synthesis of 1-ethyl-N-(4-fluorophenyl)-2-oxo-1,2-dihydrobenzo[cd]indole-6-sulfonamide

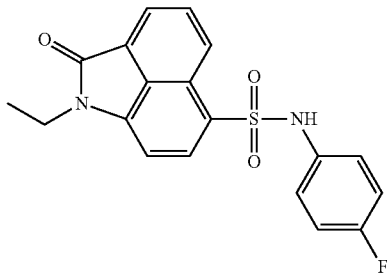 [SMILES: CCN1C(=O)c2cccc3c(S(=O)(=O)Nc4ccc(F)cc4)ccc1c23]

The synthesis can refer to Example 67. ¹H NMR (400 MHz, d-DMSO) δ 10.48 (s, 1H), 8.64 (d, J=8.4 Hz, 1H), 8.13-8.07 (m, 2H), 8.00-7.79 (m, 1H), 7.25 (d, J=7.6 Hz, 1H), 7.17-6.83 (m, 4H), 3.89 (q, J=7.2 Hz, 2H), 1.25 (t, J=7.2 Hz, 3H).

Example 78

Synthesis of N-butyl-1-ethyl-2-oxo-2-oxo-1,2-dihydrobenzo[cd]indole-6-sulfonamide

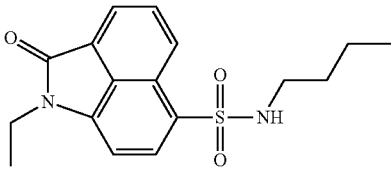 [SMILES: CCCCNS(=O)(=O)c1ccc2c3c(cccc13)C(=O)N2CC]

The synthesis can refer to Example 67. ¹H NMR (400 MHz, d-DMSO) δ 8.69 (d, J=8.4 Hz, 1H), 8.15 (d, J=7.2 Hz, 1H), 8.08 (d, J=7.6 Hz, 1H), 8.01-7.85 (m, 1H), 7.77 (t, J=6.0 Hz, 1H), 7.31 (d, J=7.6 Hz, 1H), 3.94 (q, J=7.2 Hz, 2H), 2.75 (dd, J=13.2, 6.8 Hz, 2H), 1.35-1.21 (m, 5H), 1.19-1.12 (m, 2H), 0.70 (t, J=7.2 Hz, 3H).

Example 79

Synthesis of N-(2-(1-ethyl-2-oxo-1,2-dihydrobenzo[cd]indole-6-sulfonamido)ethyl)acetamide

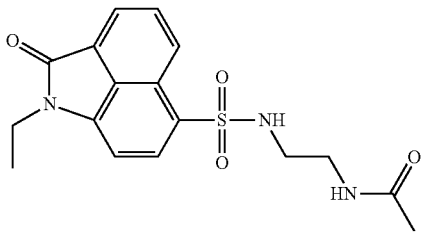 [SMILES: CCN1C(=O)c2cccc3c(S(=O)(=O)NCCNC(C)=O)ccc1c23]

The synthesis can refer to Example 67. ¹H NMR (400 MHz, d-DMSO) δ 8.65 (d, J=8.2 Hz, 1H), 8.14 (d, J=6.4 Hz, 1H), 8.06 (d, J=7.2 Hz, 1H), 7.94 (t, J=7.2 Hz, 1H), 7.87 (s, 1H), 7.76 (s, 1H), 7.30 (d, J=7.2 Hz, 1H), 3.93 (d, J=6.8 Hz, 2H), 3.01 (d, J=5.6 Hz, 2H), 2.77 (s, 2H), 1.65 (s, 3H), 1.26 (t, J=6.4 Hz, 3H).

Example 80

Synthesis of 1-ethyl-N-(2-(methyl sulfonyl)ethyl)-2-oxo-1,2-dihydrobenzo[cd]indole-6-sulfonamide

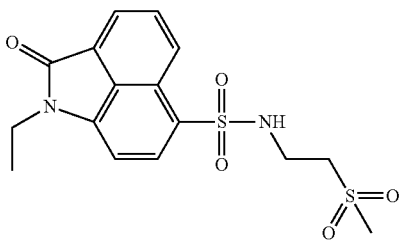 [SMILES: CCN1C(=O)c2cccc3c(S(=O)(=O)NCCS(C)(=O)=O)ccc1c23]

The synthesis can refer to Example 67. ¹H NMR (400 MHz, d-DMSO) δ 8.64 (d, J=8.4 Hz, 1H), 8.16-8.10 (m, 3H), 7.96 (t, J=7.6 Hz, 1H), 7.33 (d, J=7.6 Hz, 1H), 3.94 (q, J=6.8 Hz, 2H), 3.23 (t, J=6.8 Hz, 2H), 3.14 (t, J=6.8 Hz, 2H), 2.97 (s, 3H), 1.27 (t, J=7.2 Hz, 3H).

Example 81

Synthesis of 1-ethyl-2-oxo-N-(2-(2-oxoimidazolidin-1-yl)ethyl)-1,2-dihydrobenzo[cd]indole-6-sulfonamide

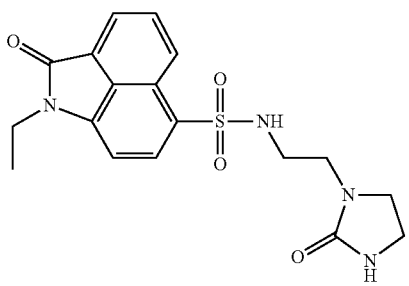 [SMILES: CCN1C(=O)c2cccc3c(S(=O)(=O)NCCN4CCNC4=O)ccc1c23]

The synthesis can refer to Example 67. ¹H NMR (400 MHz, d-DMSO) δ 8.66 (d, J=8.0 Hz, 1H), 8.14 (d, J=6.4 Hz, 1H), 8.08 (d, J=7.2 Hz, 1H), 7.92 (d, J=6.4 Hz, 2H), 7.29 (d, J=7.2 Hz, 1H), 6.23 (s, 1H), 3.93 (d, J=6.4 Hz, 2H), 3.18 (d, J=7.2 Hz, 2H), 3.09-3.02 (m, 4H), 2.86-2.84 (m, 2H), 1.26 (t, J=7.2 Hz, 3H).

Example 82

Synthesis of tert-butyl(4-(1-ethyl-2-oxo-1,2-dihydrobenzo[cd]indole-6-sulfonamido)butyl)carbamate

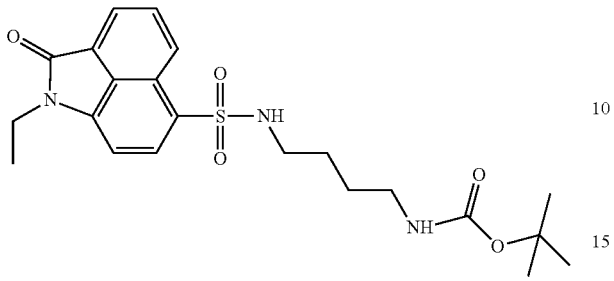

The synthesis can refer to Example 67. $^1$H NMR (400 MHz, d-DMSO) δ 8.67 (d, J=8.4 Hz, 1H), 8.13 (d, J=6.8 Hz, 1H), 8.06 (d, J=7.6 Hz, 1H), 7.93 (t, J=7.6 Hz, 1H), 7.76 (s, 1H), 7.29 (d, J=7.6 Hz, 1H), 6.67 (s, 1H), 3.92 (d, J=7.2 Hz, 2H), 2.91-2.64 (m, 4H), 1.26 (s, 9H), 1.25-1.24 (m, 4H), 1.24 (t, J=7.2 Hz, 3H).

Example 83

Synthesis of N-(5-(1-ethyl-2-oxo-1,2-dihydrobenzo[cd]indole-6-sulfonamido)pyridin-2-yl)acetamide

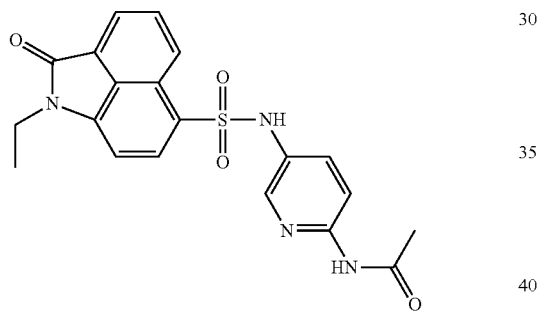

The synthesis can refer to Example 67. $^1$H NMR (400 MHz, d-DMSO) δ 10.48 (s, 1H), 10.34 (s, 1H), 8.62 (d, J=8.4 Hz, 1H), 8.12 (d, J=7.6 Hz, 1H), 8.06 (d, J=7.6 Hz, 1H), 7.99-7.70 (m, 3H), 7.41 (d, J=8.8 Hz, 1H), 7.23 (d, J=7.6 Hz, 1H), 3.88 (q, J=6.8 Hz, 2H), 1.98 (d, J=8.4 Hz, 3H), 1.22 (t, J=7.2 Hz, 3H).

Example 84

Synthesis of tert-butyl 3-(1-ethyl-2-oxo-1,2-dihydrobenzo[cd]indole-6-sulfonamido)pyrrolidine-1-carboxylate

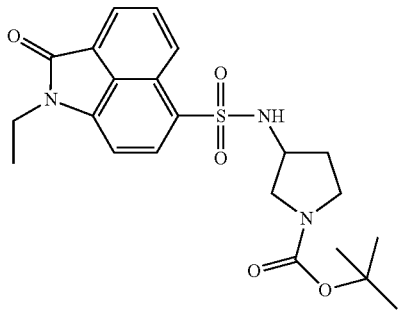 [SMILES: CCN1C(=O)c2cccc3c(S(=O)(=O)NC4CCN(C(=O)OC(C)(C)C)C4)ccc1c23]

The synthesis can refer to Example 67. $^1$H NMR (400 MHz, CDCl$_3$) δ 8.62 (d, J=8.4 Hz, 1H), 8.23 (d, J=7.6 Hz, 1H), 8.13 (d, J=7.2 Hz, 1H), 7.85 (t, J=7.6 Hz, 1H), 6.95 (d, J=7.6 Hz, 1H), 5.10 (d, J=7.2 Hz, 1H), 4.00 (q, J=7.2 Hz, 2H), 3.86 (d, J=4.8 Hz, 1H), 3.48-3.30 (m, 2H), 3.29-3.26 (m, 1H), 3.07-3.03 (m, 1H), 1.94-1.87 (m, 2H), 1.48-1.29 (m, 12H).

Example 85

Synthesis of tert-butyl 3-(1-ethyl-2-oxo-1,2-dihydrobenzo[cd]indole-6-sulfonamido)azetidine-1-carboxylate

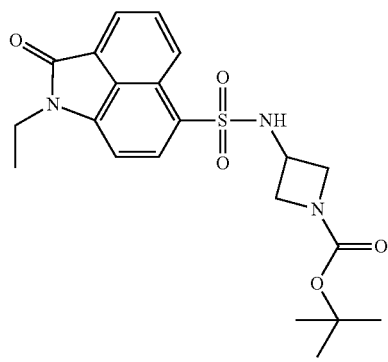 [SMILES: CCN1C(=O)c2cccc3c(S(=O)(=O)NC4CN(C(=O)OC(C)(C)C)C4)ccc1c23]

The synthesis can refer to Example 67. $^1$H NMR (400 MHz, CDCl$_3$) δ 8.60 (d, J=8.4 Hz, 1H), 8.14 (d, J=7.6 Hz, 1H), 8.12 (d, J=6.8 Hz, 1H) 7.85 (t, J=7.6 Hz, 1H), 6.92 (d, J=7.6 Hz, 1H), 5.31 (d, J=8.8 Hz, 1H), 4.11 (d, J=8.0 Hz, 1H), 4.01-3.95 (m, 4H), 3.56 (s, 2H), 1.44-1.30 (m, 12H).

Example 86

Synthesis of N-(2-cyclohexylethyl)-1-ethyl-2-oxo-1,2-dihydrobenzo[cd]indole-6-sulfonamide

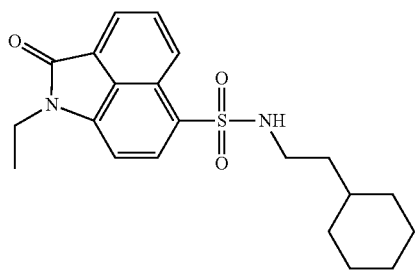

The synthesis can refer to Example 67. $^1$H NMR (400 MHz, CDCl$_3$) δ 8.64 (d, J=8.4 Hz, 1H), 8.19 (d, J=7.6 Hz, 1H), 8.12 (d, J=7.2 Hz, 1H), 7.84 (t, J=7.2 Hz, 1H), 6.93 (d, J=7.5 Hz, 1H), 4.41 (t, J=6.0 Hz, 1H), 3.99 (q, J=7.2 Hz, 2H), 2.97 (dd, J=13.2, 6.8 Hz, 2H), 1.39-1.37 (m, 4H), 1.28-1.25 (m, 6H), 1.13-1.08 (m, 2H), 1.02-0.97 (m, 2H), 0.96-0.89 (m, 2H).

Example 87

Synthesis of 1-ethyl-2-oxo-N-(pyrrolidin-3-yl)-1,2-dihydrobenzo[cd]indole-6-sulfonamide

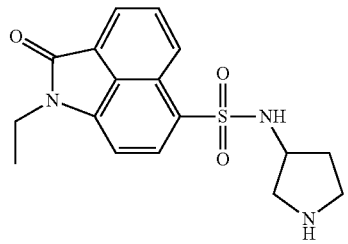 [SMILES: CCN1C(=O)c2cccc3c(S(=O)(=O)NC4CCNC4)ccc1c23]

The synthesis of tert-butyl 3-(1-ethyl-2-oxo-1,2-dihydrobenzo[cd]indole-6-sulfonamido)pyrrolidine-1-carboxylate can refer to 84.

Tert-butyl 3-(1-ethyl-2-oxo-1,2-dihydrobenzo[cd]indole-6-sulfonamido)pyrrolidine-1-carboxylate (50 mg, 0.112 mmol) was dissolved in DCM (20 mL) and trifluoroacetic acid (0.5 mL). The mixture was stirred at room temperature for 2 h. The solvent was removed and was purified by recrystallization with petroleum and ether/ethyl acetate to afford 1-ethyl-2-oxo-N-(pyrrolidin-3-yl)-1,2-dihydrobenzo[cd]indole-6-sulfonamide (37 mg, 95%) as a yellow solid. $^1$H NMR (400 MHz, d-DMSO) δ 8.74 (s, 1H), 8.65 (d, J=8.4 Hz, 1H), 8.29 (d, J=6.0 Hz, 1H), 8.18 (d, J=7.2 Hz, 1H), 8.13 (d, J=7.6 Hz, 1H), 8.03-7.86 (m, 1H), 7.34 (d, J=7.6 Hz, 1H), 3.94 (q, J=7.2 Hz, 1H), 3.74 (dd, J=12.0, 6.0 Hz, 1H), 3.18-3.12 (m, 1H), 3.11-2.99 (m, 1H), 2.93-2.89 (m, 1H), 1.90-1.83 (m, 1H), 1.69-1.66 (m, 1H), 1.27 (t, J=7.2 Hz, 2H).

Example 88

Synthesis of N-(azetidin-3-yl)-1-ethyl-2-oxo-1,2-dihydrobenzo[cd]indole-6-sulfonamide

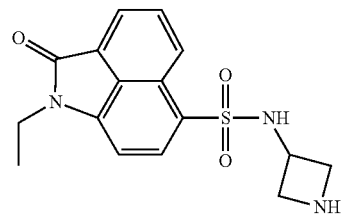 [SMILES: CCN1C(=O)c2cccc3c(S(=O)(=O)NC4CNC4)ccc1c23]

The synthesis can refer to Example 87. $^1$H NMR (400 MHz, d-DMSO) δ 8.78 (d, J=7.6 Hz, 1H), 8.61 (d, J=8.4 Hz, 2H), 8.18 (d, J=7.2 Hz, 1H), 8.10 (d, J=7.6 Hz, 1H), 7.99 (t, 7.2 Hz, 1H), 7.33 (d, J=7.6 Hz, 1H), 3.94 (q, J=7.2 Hz, 2H), 3.86 (t, J=9.2 Hz, 2H), 3.66 (s, 2H), 1.27 (t, J=7.2 Hz, 3H).

Example 89 ynthesis of 1-ethyl-N-hexyl-2-oxo-1,2-dihydrobenzo[cd]indole-6-sulfonamide

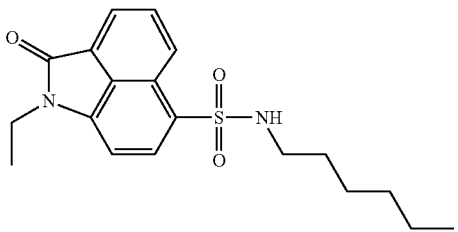 [SMILES: CCCCCCNS(=O)(=O)c1ccc2c3c(cccc13)C(=O)N2CC]

The synthesis can refer to Example 67. $^1$H NMR (400 MHz, d-DMSO) δ 8.68 (d, J=8.4 Hz, 1H), 8.14 (d, J=7.2 Hz, 1H), 8.07 (d, J=7.6 Hz, 1H), 8.00-7.83 (m, 1H), 7.76 (t, J=6.0 Hz, 1H), 7.29 (d, J=7.6 Hz, 1H), 3.93 (q, J=7.2 Hz, 2H), 2.75 (dd, J=12.8, 6.4 Hz, 2H), 1.35-1.12 (m, 6H), 1.09-0.88 (m, 6H), 0.67 (t, J=6.8 Hz, 3H).

Example 90

Synthesis of 1-ethyl-2-oxo-N-(2-(pyrrolidin-1-yl)ethyl)-1,2-dihydrobenzo[cd]indole-6-sulfonamide

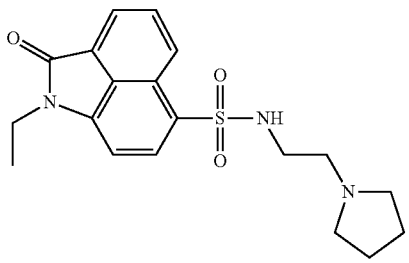 [SMILES: CCN1C(=O)c2cccc3c(S(=O)(=O)NCCN4CCCC4)ccc1c23]

The synthesis can refer to Example 67. $^1$H NMR (400 MHz, d-DMSO) δ 8.68 (d, J=8.2 Hz, 1H), 8.17 (d, J=6.8 Hz, 1H), 8.12 (d, J=7.6 Hz, 1H), 7.96 (t, J=7.6 Hz, 1H), 7.33 (d, J=7.6 Hz, 1H), 4.00-3.88 (m, 2H), 3.18-3.02 (m, 3H), 2.85 (s, 4H), 1.73 (s, 3H), 1.28 (t, J=7.2 Hz, 3H).

Example 91

Synthesis of 1-ethyl-2-oxo-N-(2-(tetrahydro-2H-pyran-4-yl)ethyl)-1,2-dihydrobenzo[cd]indole-6-sulfonamide

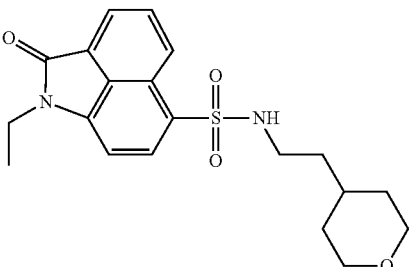

The synthesis can refer to Example 67. $^1$H NMR (400 MHz, d-DMSO) δ 8.69 (d, J=8.4 Hz, 1H), 8.16 (d, J=7.2 Hz, 1H), 8.08 (d, J=7.6 Hz, 1H), 7.96 (t, J=7.6 Hz, 1H), 7.78 (s, 1H), 7.30 (d, J=7.6 Hz, 1H), 3.93 (t, J=7.2 Hz, 2H), 3.63 (dd, J=11.2, 3.6 Hz, 2H), 2.89 (t, J=11.2 Hz, 2H), 2.80 (d, J=4.8 Hz, 2H), 1.35-1.10 (m, 8H), 0.90-0.86 (m, 2H).

Example 92

Synthesis of 1-ethyl-2-oxo-N-(tetrahydrofuran-3-yl)-1,2-dihydrobenzo[cd]indole-6-sulfonamide

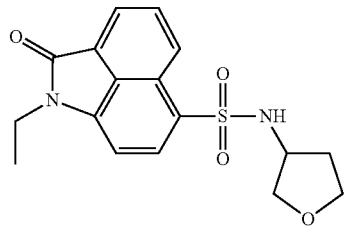 [SMILES: CCN1C(=O)c2cccc3c(S(=O)(=O)NC4CCOC4)ccc1c23]

The synthesis can refer to Example 67. $^1$H NMR (400 MHz, d-DMSO) δ 8.69 (d, J=8.4 Hz, 1H), 8.16 (d, J=6.0 Hz, 2H), 8.11 (d, J=7.6 Hz, 1H), 7.95 (t, J=7.6 Hz, 1H), 7.32 (d, J=7.6 Hz, 1H), 3.94 (q, J=7.2 Hz, 2H), 3.72 (s, 1H), 3.64 (dd, J=14.4, 7.2 Hz, 1H), 3.59-3.44 (m, 2H), 1.81-1.76 (m, 1H), 1.53 (dd, J=12.4, 6.0 Hz, 1H), 1.27 (t, J=7.2 Hz, 3H).

Example 93

Synthesis of N-(2-(4-chlorophenoxy)ethyl)-1-ethyl-2-oxo-1,2-dihydrobenzo[cd]indole-6-sulfonamide

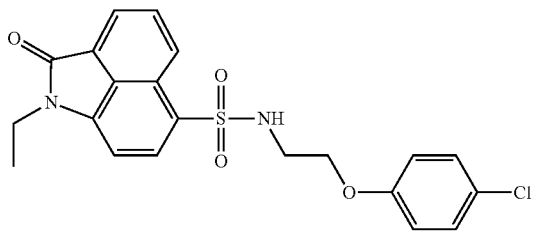 [SMILES: CCN1C(=O)c2cccc3c(S(=O)(=O)NCCOc4ccc(Cl)cc4)ccc1c23]

The synthesis can refer to Example 67. $^1$H NMR (400 MHz, CDCl$_3$) δ 8.61 (d, J=8.4 Hz, 1H), 8.19 (d, J=7.6 Hz, 1H), 8.09 (d, J=7.2 Hz, 1H), 7.82 (t, J=7.6 Hz, 1H), 7.10 (d, J=8.8 Hz, 2H), 6.88 (d, J=7.6 Hz, 1H), 6.51 (d, J=8.8 Hz, 2H), 5.08 (t, J=6.0 Hz, 1H), 3.97 (q, J=7.2 Hz, 2H), 3.88 (t, J=5.2 Hz, 2H), 3.37 (dd, J=10.8, 5.2 Hz, 2H), 1.38 (t, J=7.2 Hz, 3H).

Example 94

Synthesis of N,1-diethyl-2-oxo-1,2-dihydrobenzo[cd]indole-6-sulfonamide

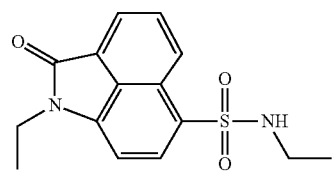 [SMILES: CCNS(=O)(=O)c1ccc2c3c(cccc13)C(=O)N2CC]

The synthesis can refer to Example 67. $^1$H NMR (400 MHz, CDCl$_3$) δ 8.65 (d, J=8.4 Hz, 1H), 8.20 (d, J=7.6 Hz, 1H), 8.12 (d, J=6.8 Hz, 1H), 7.84 (t, J=7.6 Hz, 1H), 6.93 (d, J=7.6 Hz, 1H), 4.52 (s, 1H), 3.99 (q, J=7.2 Hz, 2H), 3.02 (t, J=7.2 Hz, 2H), 1.39 (t, J=7.2 Hz, 3H), 1.08 (t, J=7.2 Hz, 3H).

Example 95

Synthesis of 1-ethyl-2-oxo-N-pentyl-1,2-dihydrobenzo[cd]indole-6-sulfonamide

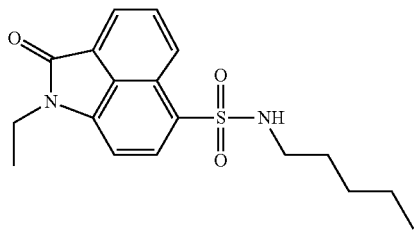 [SMILES: CCCCCNS(=O)(=O)c1ccc2c3c(cccc13)C(=O)N2CC]

The synthesis can refer to Example 67. $^1$H NMR (400 MHz, CDCl$_3$) δ 8.64 (d, J=8.4 Hz, 1H), 8.18 (d, J=7.6 Hz, 1H), 8.11 (d, J=6.8 Hz, 1H), 7.84 (t, J=7.6 Hz, 1H), 6.92 (d, J=7.6 Hz, 1H), 4.54 (d, J=6.0 Hz, 1H), 3.99 (q, J=7.2 Hz, 2H), 2.94 (q, J=6.8 Hz, 2H), 1.40 (q, J=7.2 Hz, 5H), 1.16 (d, J=6.4 Hz, 4H), 0.75 (t, J=7.2 Hz, 3H).

Example 96

Synthesis of 1-ethyl-N-methyl-2-oxo-1,2-dihydrobenzo[cd]indole-6-sulfonamide

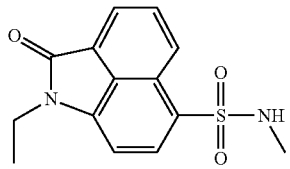 [SMILES: CCN1C(=O)c2cccc3c(S(=O)(=O)NC)ccc1c23]

The synthesis can refer to Example 67. $^1$H NMR (400 MHz, CDCl$_3$) δ 8.64 (d, J=8.4 Hz, 1H), 8.19 (d, J=7.6 Hz, 1H), 8.12 (d, J=7.2 Hz, 1H), 7.83 (t, J=7.6 Hz, 1H), 6.94 (d, J=7.6 Hz, 1H), 4.49 (d, J=5.2 Hz, 1H), 3.99 (q, J=7.2 Hz, 2H), 2.65 (d, J=5.2 Hz, 3H), 1.39 (t, J=7.2 Hz, 3H).

Example 97

Synthesis of N-cyclohexyl-1-ethyl-2-oxo-1,2-dihydrobenzo[cd]indole-6-sulfonamide

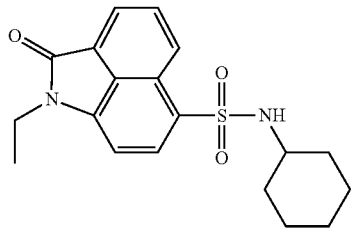 [SMILES: CCN1C(=O)c2cccc3c(S(=O)(=O)NC4CCCCC4)ccc1c23]

The synthesis can refer to Example 67. $^1$H NMR (400 MHz, CDCl$_3$) δ 8.61 (d, J=8.4 Hz, 1H), 8.20 (d, J=7.6 Hz, 1H), 8.11 (d, J=7.2 Hz, 1H), 7.84 (t, J=7.2 Hz, 1H), 6.92 (d, J=7.6 Hz, 1H), 4.52 (d, J=7.6 Hz, 1H), 3.99 (q, J=7.2 Hz, 2H), 3.29-2.92 (m, 1H), 1.75-1.63 (m, 2H), 1.58-1.50 (m, 1H), 1.49-1.46 (m, 1H), 1.40 (t, J=7.2 Hz, 3H), 1.25-1.05 (m, 6H).

Example 98

Synthesis of tert-butyl 3-(1-ethyl-2-oxo-1,2-dihydrobenzo[cd]indole-6-sulfonamido)piperidine-1-carboxylate

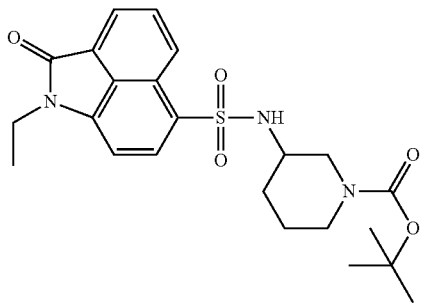 [SMILES: CCN1C(=O)c2cccc3c(S(=O)(=O)NC4CCCN(C(=O)OC(C)(C)C)C4)ccc1c23]

The synthesis can refer to Example 67. $^1$H NMR (400 MHz, CDCl$_3$) δ 8.60 (d, J=8.4 Hz, 1H), 8.21 (d, J=7.6 Hz, 1H), 8.11 (d, J=7.2 Hz, 1H), 7.84 (t, J=7.2 Hz, 1H), 6.92 (d, J=7.6 Hz, 1H), 4.87 (s, 1H), 3.98 (q, J=7.2 Hz, 2H), 3.47-3.16 (m, 4H), 3.02 (dd, J=13.2, 7.2 Hz, 1H), 1.67-1.53 (m, 2H), 1.47-1.25 (m, 14H).

Example 99

Synthesis of 1-ethyl-N-isobutyl-2-oxo-1,2-dihydrobenzo[cd]indole-6-sulfon amide

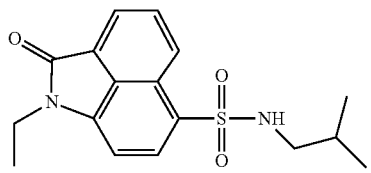 [SMILES: CCN1C(=O)c2cccc3c(S(=O)(=O)NCC(C)C)ccc1c23]

The synthesis can refer to Example 67. $^1$H NMR (400 MHz, CDCl$_3$) δ 8.64 (d, J=8.4 Hz, 1H), 8.18 (d, J=7.6 Hz, 1H), 8.11 (d, J=7.2 Hz, 1H), 7.84 (t, J=7.6 Hz, 1H), 6.92 (d, J=7.6 Hz, 1H), 4.61 (t, J=6.4 Hz, 1H), 3.99 (q, J=7.2 Hz, 2H), 2.75 (t, J=6.4 Hz, 2H), 1.67 (dt, J=13.2, 6.8 Hz, 1H), 1.39 (t, J=7.2 Hz, 3H), 0.81 (d, J=6.8 Hz, 6H).

Example 10

Synthesis of 1-ethyl-2-oxo-N-propyl-1,2-dihydrobenzo[cd]indole-6-sulfonamide

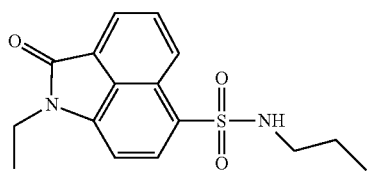 [SMILES: CCCNS(=O)(=O)c1ccc2c3c(cccc13)C(=O)N2CC]

The synthesis can refer to Example 67. $^1$H NMR (400 MHz, CDCl$_3$) δ 8.65 (d, J=8.4 Hz, 1H), 8.18 (d, J=7.6 Hz, 1H), 8.10 (d, J=7.2 Hz, 1H), 7.92-7.68 (m, 1H), 6.92 (d, J=7.6 Hz, 1H), 4.66 (t, J=6.0 Hz, 1H), 3.98 (q, J=7.2 Hz, 2H), 2.91 (dd, J=13.2, 6.8 Hz, 2H), 1.46 (dt, J=14.4, 7.2 Hz, 2H), 1.39 (t, J=7.2 Hz, 3H), 0.80 (t, J=7.2 Hz, 3H).

Example 101

Synthesis of 1-ethyl-N-(3-(4-methylpiperazin-1-yl)propyl)-2-oxo-1,2-dihydrobenzo[cd]indole-6-sulfonamide

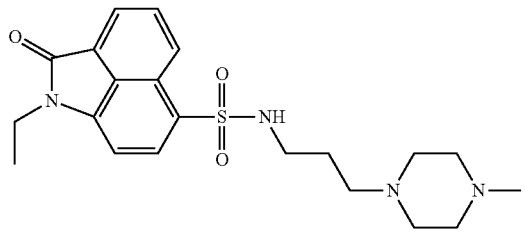 [SMILES: CCN1C(=O)c2cccc3c(S(=O)(=O)NCCCN4CCN(C)CC4)ccc1c23]

The synthesis can refer to Example 67. $^1$H NMR (400 MHz, d-DMSO) δ 8.68 (d, J=8.4 Hz, 1H), 8.16 (d, J=6.8 Hz, 1H), 8.08 (d, J=7.2 Hz, 1H), 7.95 (t, J=7.6 Hz, 1H), 7.78 (s, 1H), 7.31 (d, J=7.6 Hz, 1H), 3.94 (q, J=7.2 Hz, 2H), 2.79 (d, J=5.6 Hz, 2H), 2.23-1.86 (m, 11H), 1.48-1.33 (m, 2H), 1.28 (t, J=7.2 Hz, 3H).

Example 102

Synthesis of 1-ethyl-2-oxo-N-(2-(piperidin-1-yl)ethyl)-1,2-dihydrobenzo[cd]indole-6-sulfonamide

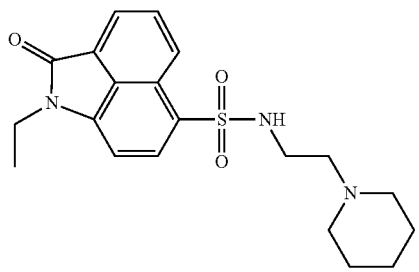 [SMILES: CCN1C(=O)c2cccc3c(S(=O)(=O)NCCN4CCCCC4)ccc1c23]

The synthesis can refer to Example 67. $^1$H NMR (400 MHz, d-DMSO) δ 8.68 (d, J=8.4 Hz, 1H), 8.15 (d, J=6.8 Hz, 1H), 8.10 (d, J=7.6 Hz, 1H), 7.94 (t, J=7.6 Hz, 1H), 7.67 (s, 1H), 7.30 (d, J=7.6 Hz, 1H), 3.94 (q, J=7.2 Hz, 2H), 2.88 (t, J=6.4 Hz, 2H), 2.23-2.11 (m, 2H), 2.10-2.01 (m, 3H), 1.30-1.22 (m, 7H), 0.94-0.65 (m, 2H).

Example 103

Synthesis of N-(4,4-diethoxybutyl)-1-ethyl-2-oxo-1,2-dihydrobenzo[cd]indole-6-sulfonamide

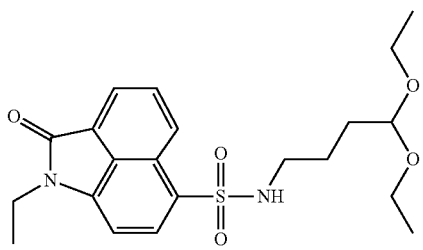 [SMILES: CCOC(CCCNS(=O)(=O)c1ccc2c3c(cccc13)C(=O)N2CC)OCC]

The synthesis can refer to Example 67. ¹H NMR (400 MHz, d-DMSO) δ 8.67 (d, J=8.4 Hz, 1H), 8.14 (d, J=6.8 Hz, 1H), 8.06 (d, J=7.6 Hz, 1H), 7.93 (t, J=7.6 Hz, 1H), 7.79 (t, J=5.2 Hz, 1H), 7.29 (d, J=7.6 Hz, 1H), 4.18 (s, 1H), 3.92 (q, J=6.8 Hz, 2H), 3.42-3.31 (m, 2H), 3.23-3.17 (m, 2H), 2.78 (d, J=5.2 Hz, 2H), 1.35-1.21 (m, 7H), 0.95 (t, J=6.8 Hz, 6H).

Example 104

Synthesis of ethyl 3-(1-ethyl-2-oxo-1,2-dihydrobenzo[cd]indole-6-sulfonamido)propanoate

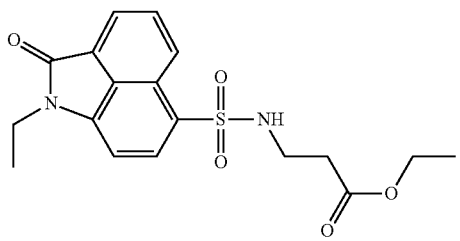 [SMILES: CCOC(=O)CCNS(=O)(=O)c1ccc2c3c(cccc13)C(=O)N2CC]

The synthesis can refer to Example 67. ¹H NMR (400 MHz, CDCl₃) δ 8.61 (d, J=8.4 Hz, 1H), 8.19 (d, J=7.6 Hz, 1H), 8.12 (d, J=7.2 Hz, 1H), 7.96-7.69 (m, 1H), 6.93 (d, J=7.6 Hz, 1H), 5.35 (t, J=6.4 Hz, 1H), 4.01-3.96 (m, 4H), 3.19 (dd, J=12.4, 6.4 Hz, 2H), 2.48 (t, J=6.0 Hz, 2H), 1.39 (t, J=7.2 Hz, 3H), 1.18 (t, J=7.2 Hz, 3H).

Example 105

Synthesis of 1-ethyl-N-((1-ethylpyrrolidin-2-yl)methyl)-2-oxo-1,2-dihydrobenzo[cd]indole-6-sulfonamide

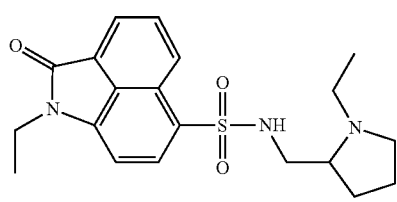 [SMILES: CCN1C(=O)c2cccc3c(S(=O)(=O)NCC4CCCN4CC)ccc1c23]

The synthesis can refer to Example 67. ¹H NMR (400 MHz, CDCl₃) δ 8.68 (d, J=8.4 Hz, 1H), 8.12 (dd, J=10.4, 7.2 Hz, 2H), 7.96-7.78 (m, 1H), 6.90 (d, J=7.6 Hz, 1H), 3.98 (q, J=7.2 Hz, 2H), 3.67 (d, J=5.6 Hz, 1H), 3.46 (s, 1H), 3.37 (dd, J=14.4, 7.6 Hz, 2H), 3.19 (dd, J=14.4, 3.2 Hz, 1H), 2.87 (s, 1H), 2.76 (s, 1H), 2.15-1.80 (m, 5H), 1.38 (t, J=7.2 Hz, 6H).

Example 106

Synthesis of 1-ethyl-N-(1-methylpiperidin-4-yl)-2-oxo-1,2-dihydrobenzo[cd]indole-6-sulfonamide

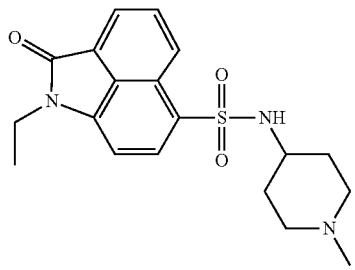 [SMILES: CCN1C(=O)c2cccc3c(S(=O)(=O)NC4CCN(C)CC4)ccc1c23]

The synthesis can refer to Example 67. ¹H NMR (400 MHz, d-DMSO) δ 8.68 (d, J=8.4 Hz, 1H), 8.14 (d, J=7.2 Hz, 1H), 8.09 (d, J=7.6 Hz, 1H), 7.93 (dd, J=12.4, 5.6 Hz, 2H), 7.29 (d, J=7.6 Hz, 1H), 3.93 (q, J=7.2 Hz, 2H), 2.93 (s, 1H), 2.58 (d, J=11.2 Hz, 2H), 2.06 (s, 3H), 1.82 (s, 2H), 1.44 (d, J=10.4 Hz, 2H), 1.38-1.35 (m, 2H), 1.27 (t, J=7.2 Hz, 3H).

Example 107

Synthesis of N-cycloheptyl-1-ethyl-2-oxo-1,2-dihydrobenzo[cd]indole-6-sulfonamide

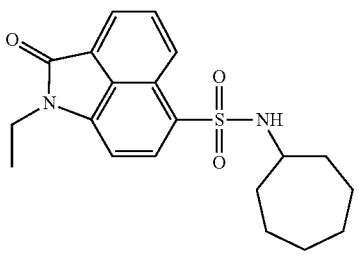 [SMILES: CCN1C(=O)c2cccc3c(S(=O)(=O)NC4CCCCCC4)ccc1c23]

The synthesis can refer to Example 67. ¹H NMR (400 MHz, CDCl₃) δ 8.63 (d, J=8.4 Hz, 1H), 8.21 (d, J=7.6 Hz, 1H), 8.13 (d, J=7.2 Hz, 1H), 7.93-7.60 (m, 1H), 6.94 (d, J=7.6 Hz, 1H), 4.55 (d, J=8.0 Hz, 1H), 4.01 (q, J=7.2 Hz, 2H), 3.50-3.20 (m, 1H), 1.73-1.69 (m, 2H), 1.55-0.99 (m, 15H).

Example 108

Synthesis of 1-ethyl-2-oxo-N-(tetrahydro-2H-pyran-4-yl)-1,2-dihydrobenzo[cd]indole-6-sulfonamide

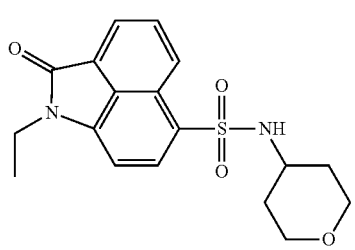 [SMILES: CCN1C(=O)c2cccc3c(S(=O)(=O)NC4CCOCC4)ccc1c23]

The synthesis can refer to Example 67. ¹H NMR (400 MHz, CDCl₃) δ 8.61 (d, J=8.4 Hz, 1H), 8.21 (d, J=7.6 Hz, 1H), 8.12 (d, J=7.2 Hz, 1H), 7.93-7.77 (m, 1H), 6.92 (d, J=7.6 Hz, 1H), 4.65 (d, J=8.0 Hz, 1H), 3.99 (q, J=7.2 Hz, 2H), 3.82 (d, J=12.0 Hz, 2H), 3.44-3.34 (m, 1H), 3.30 (t, J=10.8 Hz, 2H), 1.69 (d, J=13.2 Hz, 2H), 1.51-1.35 (m, 5H).

Example 64

Synthesis of tert-butyl 4-(2-(1-ethyl-2-oxo-1,2-dihydrobenzo[cd]indole-6-sulfonamido)ethyl)piperazine-1-carboxylate

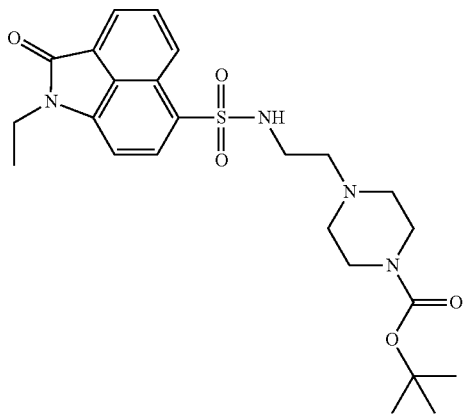 [SMILES: CCN1C(=O)c2cccc3c(S(=O)(=O)NCCN4CCN(C(=O)OC(C)(C)C)CC4)ccc1c23]

The synthesis can refer to Example 67. ¹H NMR (400 MHz, CDCl₃) δ 8.63 (d, J=8.4 Hz, 1H), 8.19 (d, J=7.6 Hz, 1H), 8.12 (d, J=7.2 Hz, 1H), 7.93-7.75 (m, 1H), 6.93 (d, J=7.6 Hz, 1H), 5.35 (s, 1H), 3.99 (q, J=7.2 Hz, 2H), 3.28-3.10 (m, 4H), 2.98 (s, 2H), 2.41-2.23 (m, 2H), 2.16-2.04 (m, 4H), 1.47-1.30 (m, 12H).

Example 110

Synthesis of N-cyclohexyl-1-methyl-2-oxo-1,2-dihydrobenzo[cd]indole-6-sulfonamide

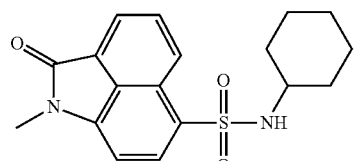

The synthesis can refer to Example 67. ¹H NMR (400 MHz, d-DMSO) δ 8.70 (d, J=8.4 Hz, 1H), 8.14 (d, J=7.6 Hz, 1H), 8.11 (d, J=7.2 Hz, 1H), 8.02-7.89 (m, 1H), 7.85 (d, J=7.6 Hz, 1H), 7.23 (d, J=7.6 Hz, 1H), 3.38 (s, 3H), 2.94 (s, 1H), 1.57-1.33 (m, 5H), 1.04-0.88 (m, 5H).

Example 64

Synthesis of N-butyl-1-methyl-2-oxo-1,2-dihydrobenzo[cd]indole-6-sulfonamide

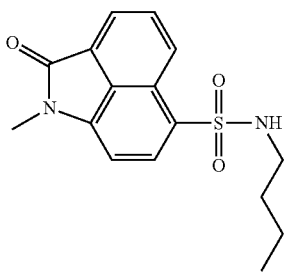 [SMILES: CCCCNS(=O)(=O)c1ccc2c3c(cccc13)C(=O)N2C]

The synthesis can refer to Example 67. ¹H NMR (400 MHz, d-DMSO) δ 8.68 (d, J=8.4 Hz, 1H), 8.15 (d, J=7.2 Hz, 1H), 8.08 (d, J=7.6 Hz, 1H), 7.99-7.83 (m, 1H), 7.77 (s, 1H), 7.25 (d, J=7.6 Hz, 1H), 3.39 (s, 3H), 2.74 (d, J=3.2 Hz, 2H), 1.27 (dd, J=14.8, 7.2 Hz, 2H), 1.15 (dd, J=14.8, 7.2 Hz, 2H), 0.70 (t, J=7.2 Hz, 3H).

Example 112

Synthesis of N-cyclohexyl-2-oxo-1-propyl-1,2-dihydrobenzo[cd]indole-6-sulfonamide

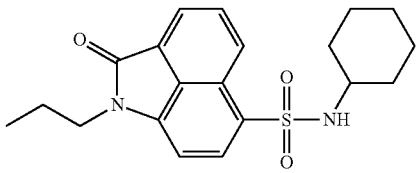 [SMILES: CCCN1C(=O)c2cccc3c(S(=O)(=O)NC4CCCCC4)ccc1c23]

The synthesis can refer to Example 67. ¹H NMR (400 MHz, CDCl₃) δ 8.62 (d, J=8.4 Hz, 1H), 8.18 (d, J=7.2 Hz, 1H), 8.11 (d, J=7.2 Hz, 1H), 7.83 (t, 7.2 Hz, 1H), 6.91 (d, J=7.6 Hz, 1H), 4.57 (d, J=7.6 Hz, 1H), 3.89 (t, J=7.2 Hz, 2H), 3.31-3.03 (m, 1H), 1.82 (dt, J=14.8, 7.2 Hz, 2H), 1.74-1.64 (m, 2H), 1.57-1.56 (m, 2H), 1.48 (d, J=12.4 Hz, 1H), 1.17-1.08 (m, 4H), 1.02 (t, J=7.2 Hz, 3H).

Example 113

Synthesis of 2-oxo-N,1-dipropyl-1,2-dihydrobenzo[cd]indole-6-sulfonamide

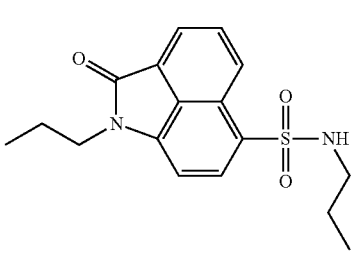 [SMILES: CCCNS(=O)(=O)c1ccc2c3c(cccc13)C(=O)N2CCC]

The synthesis can refer to Example 67. ¹H NMR (400 MHz, CDCl₃) δ 8.64 (d, J=8.4 Hz, 1H), 8.18 (d, J=7.6 Hz, 1H), 8.11 (d, J=7.2 Hz, 1H), 7.94-7.66 (m, 1H), 6.92 (d, J=7.6 Hz, 1H), 4.60 (t, J=6.0 Hz, 1H), 3.89 (t, J=7.2 Hz, 2H), 2.92 (d d, J=13.6, 6.8 Hz, 2H), 1.78 (dt, J=14.4, 7.2 Hz, 2H), 1.44 (dt, J=14.4, 7.2 Hz, 2H), 1.01 (t, J=7.2 Hz, 3H), 0.81 (t, J=7.2 Hz, 3H).

Example 114

Synthesis of N-butyl-2-oxo-1-propyl-1,2-dihydrobenzo[cd]indole-6-sulfonamide

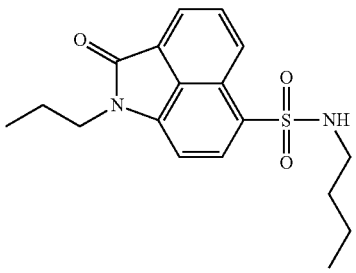 [SMILES: CCCCNS(=O)(=O)c1ccc2c3c(cccc13)C(=O)N2CCC]

The synthesis can refer to Example 67. $^1$H NMR (400 MHz, CDCl$_3$) δ 8.64 (d, J=8.4 Hz, 1H), 8.18 (d, J=7.6 Hz, 1H), 8.12 (d, J=7.2 Hz, 1H), 7.84 (dd, J=8.2, 7.2 Hz, 1H), 6.92 (d, J=7.6 Hz, 1H), 4.51 (t, J=6.0 Hz, 1H), 3.90 (t, J=7.2 Hz, 2H), 2.94 (dd, J=13.2, 6.8 Hz, 2H), 1.88-1.70 (m, 2H), 1.50-1.33 (m, 2H), 1.23 (dt, J=14.4, 7.2 Hz, 3H), 1.01 (t, J=7.2 Hz, 3H), 0.78 (t, J=7.2 Hz, 3H).

Example 115

Synthesis of N-butyl-2-oxo-1,2-dihydrobenzo[cd]indole-6-sulfonamide

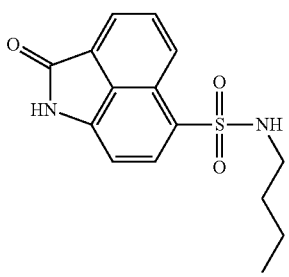 [SMILES: CCCCNS(=O)(=O)c1ccc2c3c(cccc13)C(=O)N2]

The synthesis can refer to Example 67. $^1$H NMR (400 MHz, d-DMSO) δ 11.13 (s, 1H), 8.68 (d, J=8.4 Hz, 1H), 8.11 (d, J=7.2 Hz, 1H), 8.03 (d, J=7.6 Hz, 1H), 7.98-7.87 (m, 1H), 7.74 (t, J=5.6 Hz, 1H), 7.06 (d, J=7.6 Hz, 1H), 2.74 (dd, J=13.2, 6.8 Hz, 2H), 1.35-1.19 (m, 2H), 1.19-0.98 (m, 2H), 0.69 (t, J=7.2 Hz, 3H).

Example 116

Synthesis of N-butyl-1-isobutyl-2-oxo-1,2-dihydrobenzo[cd]indole-6-sulfonamide

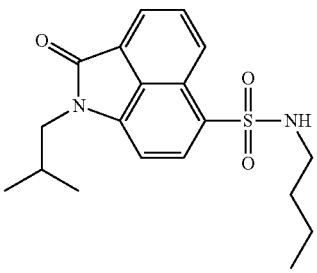 [SMILES: CCCCNS(=O)(=O)c1ccc2c3c(cccc13)C(=O)N2CC(C)C]

The synthesis can refer to Example 67. $^1$H NMR (400 MHz, d-DMSO) δ 8.69 (d, J=8.4 Hz, 1H), 8.16 (d, J=7.2 Hz, 1H), 8.06 (d, J=7.6 Hz, 1H), 8.03-7.83 (m, 1H), 7.77 (t, J=6.0 Hz, 1H), 7.30 (d, J=7.6 Hz, 1H), 3.72 (d, J=7.2 Hz, 2H), 2.76 (dd, J=12.8, 6.8 Hz, 2H), 2.15 (dt, J=13.2, 6.8 Hz, 1H), 1.37-1.21 (m, 2H), 1.18-1.10 (m, 2H), 0.93 (s, 3H), 0.91 (s, 3H), 0.68 (t, J=7.2 Hz, 3H).

Example 117

Synthesis of N-cyclohexyl-1-isobutyl-2-oxo-1,2-dihydrobenzo[cd]indole-6-sulfonamide

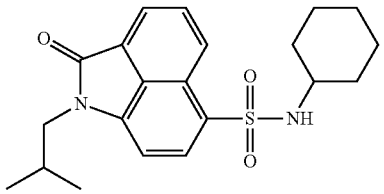 [SMILES: CC(C)CN1C(=O)c2cccc3c(S(=O)(=O)NC4CCCCC4)ccc1c23]

The synthesis can refer to Example 67. $^1$H NMR (400 MHz, d-DMSO) 8.70 (d, J=8.4 Hz, 1H), 8.12 (d, J=7.2 Hz, 1H), 8.08 (d, J=7.6 Hz, 1H), 8.08-7.93 (m, 1H), 7.85 (t, J=6.0 Hz, 1H), 7.30 (d, J=7.6 Hz, 1H), 3.71 (d, J=7.2 Hz, 2H), 2.94 (s, 1H), 2.08-1.96 (m, 1H), 1.47-1.36 (m, 5H), 1.05-0.90 (m, 5H).

Example 118

Synthesis of N-cyclohexyl-2-oxo-1,2-dihydrobenzo[cd]indole-6-sulfonamide

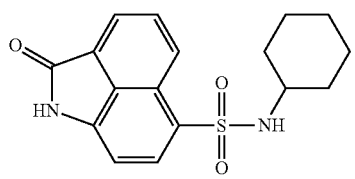 [SMILES: O=C1Nc2ccc(S(=O)(=O)NC3CCCCC3)c3cccc1c23]

The synthesis can refer to Example 67. $^1$H NMR (400 MHz, d-DMSO) δ 11.10 (s, 1H), 8.69 (d, J=8.4 Hz, 1H), 8.09 (d, J=6.8 Hz, 1H), 8.04 (d, J=7.6 Hz, 1H), 7.96-7.87 (m, 1H), 7.81 (d, J=7.6 Hz, 1H), 7.04 (d, J=7.6 Hz, 1H), 2.93 (s, 1H), 1.58-1.30 (m, 5H), 1.06-0.98 (m, 5H).

Example 119

Synthesis of N-(3-acetylphenyl)-1-ethyl-2-oxo-1,2-dihydrobenzo[cd]indole-6-sulfonamide

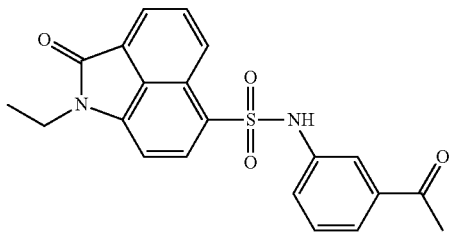 [SMILES: CCN1C(=O)c2cccc3c(S(=O)(=O)Nc4cccc(C(C)=O)c4)ccc1c23]

The synthesis can refer to Example 67. ¹H NMR (400 MHz, d-DMSO) δ 10.82 (s, 1H), 8.70 (d, J=8.4 Hz, 1H), 8.19 (d, J=7.6 Hz, 1H), 8.13 (d, J=6.8 Hz, 1H), 7.95 (t, J=7.6 Hz, 1H), 7.65-7.46 (m, 2H), 7.39-7.24 (m, 3H), 3.88 (q, J=6.8 Hz, 2H), 2.45 (s, 3H), 1.22 (t, J=7.2 Hz, 3H). ¹³C NMR (500 MHz, d-DMSO) δ 197.1, 166.6, 143.4, 138.0, 137.5, 133.5, 130.7, 129.6, 128.9, 127.4, 126.0, 125.2, 124.8, 123.9, 123.8, 123.2, 117.7, 103.9, 34.6, 26.5, 13.5.

Example 120

Synthesis of N-(4-chlorophenyl)-1-ethyl-2-oxo-1,2-dihydrobenzo[cd]indole-6-sulfonamide

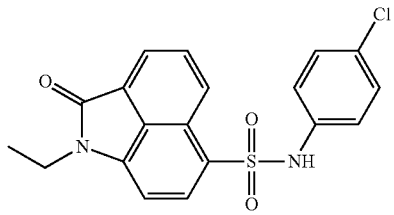 [SMILES: CCN1C(=O)c2cccc3c(S(=O)(=O)Nc4ccc(Cl)cc4)ccc1c23]

The synthesis can refer to Example 67. ¹H NMR (400 MHz, CDCl₃) δ 8.54 (d, J=8.4 Hz, 1H), 8.09 (d, J=7.6 Hz, 2H), 7.79 (t, J=7.6 Hz, 1H), 7.13 (d, J=8.4 Hz, 2H), 6.94 (d, J=8.4 Hz, 2H), 6.90 (s, 1H), 6.85 (d, J=7.6 Hz, 1H), 3.95 (q, J=7.2 Hz, 2H), 1.36 (t, J=7.2 Hz, 3H).

Example 121

Synthesis of 1-ethyl-2-oxo-N-phenyl-1,2-dihydrobenzo[cd]indole-6-sulfonamide

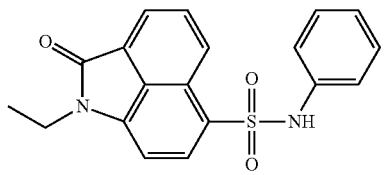 [SMILES: CCN1C(=O)c2cccc3c(S(=O)(=O)Nc4ccccc4)ccc1c23]

The synthesis can refer to Example 67. ¹H NMR (400 MHz, d-DMSO) δ 10.56 (s, 1H), 8.69 (d, J=8.4 Hz, 1H), 8.16-8.11 (m, 2H), 7.93 (t, J=7.6 Hz, 1H), 7.26 (d, J=7.6 Hz, 1H), 7.16 (t, J=7.6 Hz, 2H), 7.04 (d, J=7.6 Hz, 2H), 6.94 (t, J=7.2 Hz, 1H), 3.89 (q, J=7.2 Hz, 2H), 1.23 (t, J=7.2 Hz, 3H).

Example 122

Synthesis of N-(2-chlorophenyl)-1-ethyl-2-oxo-1,2-dihydrobenzo[cd]indole-6-sulfonamide

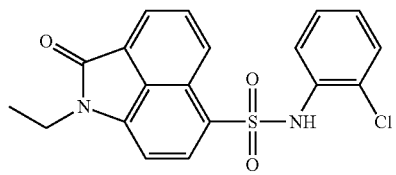 [SMILES: CCN1C(=O)c2cccc3c(S(=O)(=O)Nc4ccccc4Cl)ccc1c23]

The synthesis can refer to Example 67. ¹H NMR (400 MHz, CDCl₃) δ 8.51 (d, J=8.4 Hz, 1H), 8.14 (d, J=7.6 Hz, 1H), 8.07 (d, J=7.2 Hz, 1H), 7.77 (t, J=7.6 Hz, 1H), 7.66 (d, J=8.4 Hz, 1H), 7.22 (t, J=7.6 Hz, 1H), 7.13 (d, J=7.6 Hz, 2H), 6.99 (t, J=7.6 Hz, 1H), 6.84 (d, J=7.6 Hz, 1H), 3.94 (q, J=7.2 Hz, 2H), 1.35 (t, J=7.2 Hz, 3H).

Example 123

Synthesis of N-(3-chlorophenyl)-1-ethyl-2-oxo-1,2-dihydrobenzo[cd]indole-6-sulfonamide

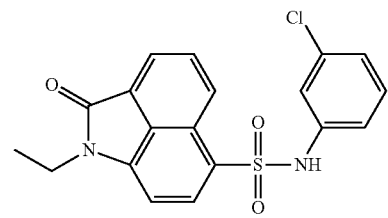 [SMILES: CCN1C(=O)c2cccc3c(S(=O)(=O)Nc4cccc(Cl)c4)ccc1c23]

The synthesis can refer to Example 67. ¹H NMR (400 MHz, CDCl₃) δ 8.55 (d, J=8.4 Hz, 1H), 8.16 (d, J=7.6 Hz, 1H), 8.10 (d, J=7.2 Hz, 1H), 7.80 (t, J=7.6 Hz, 1H), 7.16-7.01 (m, 3H), 6.93-6.82 (m, 2H), 3.96 (d, J=7.2 Hz, 2H), 1.37 (t, J=7.2 Hz, 3H).

Example 124

Activity test in vitro: the compounds of the present invention were conducted the AlphaScreen assay to confirm the ability of a ligand to disrupt the interaction of BRD(1) and its SRC1-4 peptide.

1. Purpose of AlphaScreen Assay

To test the ability of the compounds of the present invention inhibit BRD(1) protein.

2. Experimental Materials

BRD4(1) protein, 500 nM; buffer, (10×) MOPS (500 mM), CHAPS (0.5 mM), NaF (500 mM), BSA (1 mg/mL), PH (7.4); streptavidin donor beads 50 μg/mL, nickel acceptor beads 50 μg/mL, BRD4(1) ligand, biotinylated SRC1-4 peptide, H4KAc4-botin (SGRG{Lys-Ac}GG{Lys-Ac}GLG{Lys-Ac}GGA{Lys-Ac} RHR{Lys(biotin)}) 50 nM. 150 μL mix system: BRD4(1) protein, 15 μL; buffer, 15

µL; ddH$_2$O, 15 µL; compound, 15 µL; streptavidin donor beads, 15 µL; nickel acceptor beads, 15 µL; positive compound, (+)-JQ1.

3. Protocol

The BRD4(1) protein and biotinylated SRC1-4 peptide were added in ddH2O and buffer. The reaction mixture was incubated at 20° C. for 1.5 h, streptavidin donor beads and nickel acceptor beads was added. The reaction mixture was incubated at 20° C. in dark for 1 h. The reaction mixture (40 µL) was transferred to 384 well plates, and tested by PE Envison2104 multifunctional detection of microplate reader. Excitation wavelength, 680 nM; Emission wavelength, 520-620 nM.

Example 125

Activity test in vitro: the compounds of the present invention were conducted the TSA assay to determine the thermodynamic stability of BRD4(1).

1. Purpose of TSA Assay

To test the ability of the compounds of the present invention inhibit BRD(1) protein.

2. Experimental Materials

BRD4(1) protein, 100 µM; compounds, 400 µM, buffer, (10×) MOPS (50 mM), NaCl (150 mM), glycerin 10%, PH (7.5); Sypro Orange Protein Gel Stain (500×). Mix system: BRD4(1) protein, 2 µL; Sypro Orange Protein Gel Stain (500×), 2 µL; compound, 10 µL; buffer, 2 µL; ddH$_2$O, 2 µL, positive compound, (+)-JQ1.

3. Protocol

The 10 µL reaction mix was added to 96-well PCR plates. SYPRO Orange (Sigma) was added as a fluorescence probe at a dilution of 1:1000 and incubated with compounds on ice for 30 min. The total DMSO concentration was less than 2%. The TSA was carried out using the Bio-Rad CFX96 Real-Time PCR System. The temperature was raised at a step of 0.5° C. per minute from 30° C. to 80° C. The fluorescence readings were recorded at a 0.5° C. interval, and obtained the ΔTm.

The results come from the AlphaScreen assay and TSA assay in table 1-4.

TABLE 1

The activities of compounds of formula I

| Compounds | AlphaScreen (µM) | TSA ΔTm (° C.) |
|---|---|---|
| (+)-JQ1 | 0.18 | 11.5 |
| Example 1 | 0.53 | 7.4 |
| Example 2 | 0.51 | 7.1 |
| Example 3 | 1.08 | 7.5 |
| Example 4 | 0.52 | 8.5 |
| Example 5 | 0.14 | 10 |
| Example 6 | 1.70 | 6.5 |
| Example 7 | 0.84 | 6.0 |
| Example 8 | 0.24 | 9.5 |
| Example 9 | 0.41 | 9.5 |
| Example 10 | 1.68 | 8 |
| Example 11 | 2.08 | 5.5 |
| Example 12 | 5.59 | 6.5 |
| Example 13 | 6.29 | 6.0 |
| Example 14 | 5.71 | 6.5 |
| Example 15 | 6.05 | 3.0 |
| Example 16 | 4.00 | 5.0 |
| Example 17 | 2.27 | 7.0 |
| Example 18 | 0.56 | 9.0 |
| Example 19 | 0.47 | 9.5 |
| Example 20 | 1.25 | 7.0 |
| Example 21 | 0.34 | 8.1 |

TABLE 1-continued

The activities of compounds of formula I

| Compounds | AlphaScreen (µM) | TSA ΔTm (° C.) |
|---|---|---|
| Example 22 | 2.56 | 5.7 |
| Example 23 | 3.7 | 2.4 |
| Example 24 | 1.84 | 4.2 |
| Example 25 | 8.17 | 4.2 |
| Example 26 | 12.97 | 3 |
| Example 27 | 3.13 | 4.2 |
| Example 28 | 3.51 | 5.7 |
| Example 29 | 2.73 | 6.3 |
| Example 30 | 0.97 | 7.2 |
| Example 31 | 0.41 | 9 |
| Example 32 | 3.53 | 4 |
| Example 33 | 3.87 | 5 |
| Example 34 | >20 | 2.4 |
| Example 35 | 2.55 | 4.5 |
| Example 36 | 7.31 | 1.2 |
| Example 37 | 10.71 | 2.1 |
| Example 38 | >20 | 3.9 |
| Example 39 | >20 | 3.3 |
| Example 40 | >20 | 1.8 |
| Example 41 | 5.64 | 4.5 |
| Example 42 | 4.15 | 6 |
| Example 43 | 4.81 | 3.6 |
| Example 44 | >20 | 3 |
| Example 45 | 0.85 | 4.5 |

TABLE 2

The activities of compounds of formula II

| Compounds | Alphascreen (µM) | TSA(° C.) ΔTm (° C.) |
|---|---|---|
| Example 46 | >20 | 3 |
| Example 47 | >20 | 0 |
| Example 48 | >20 | 3.6 |
| Example 49 | >20 | 0 |
| Example50 | >20 | 1 |
| Example 51 | >20 | 2.4 |
| Example 52 | 14.51 | 4 |
| Example 53 | >20 | 0 |
| Example 54 | >20 | 0 |
| Example 55 | >20 | 0 |

TABLE 3

The activities of compounds of formula III

| Compounds | Alphascreen (µM) | TSA(° C.) ΔTm (° C.) |
|---|---|---|
| Example 56 | >20 | 0 |
| Example 57 | 11.18 | 4 |
| Example 58 | 2.7 | 2 |
| Example 59 | >20 | 1 |
| Example 60 | 1.77 | 2 |
| Example 61 | >20 | 2 |
| Example 62 | 2.49 | 2 |

TABLE 4

The activities of compounds of formula IV

| Compounds | Alphascreen (µM) | TSA(° C.) ΔTm (° C.) |
|---|---|---|
| Example 63 | 3.18 | 5 |
| Example 64 | 1.94 | 5 |
| Example 65 | 20.7 | 2.5 |

TABLE 4-continued

The activities of compounds of formula IV

| Compounds | Alphascreen (μM) | TSA(° C.) ΔTm (° C.) |
|---|---|---|
| Example 66 | 5.90 | 4 |
| Example 67 | 6.69 | 3 |
| Example 68 | 14.45 | 3.5 |
| Example 69 | 13.92 | 3.5 |
| Example 70 | 7.55 | 3.5 |
| Example 71 | 1.69 | 5.5 |
| Example 72 | 0.21 | 7 |
| Example 73 | 7.70 | 2 |
| Example 74 | 2.58 | 4 |
| Example 75 | 4.7 | 3.5 |
| Example 76 | 1.04 | 6.8 |
| Example 77 | 1.53 | 4.5 |
| Example 78 | 0.44 | 8 |
| Example 79 | >20 | 2.4 |
| Example 80 | >20 | 1.7 |
| Example 81 | >20 | 2.4 |
| Example 82 | 1.16 | 6.2 |
| Example 83 | 12.03 | 2.4 |
| Example 84 | 4.10 | 3.5 |
| Example 85 | 4.84 | 3.4 |
| Example 86 | 2.47 | 1.8 |
| Example 87 | >20 | 1.8 |
| Example 88 | >20 | 0.5 |
| Example 89 | >20 | 3.5 |
| Example 90 | >20 | 0.7 |
| Example 91 | 3.44 | 3.9 |
| Example 92 | 1.67 | 6.1 |
| Example 93 | >20 | 0.2 |
| Example 94 | 1.09 | 6.1 |
| Example 95 | 1.50 | 5.5 |
| Example 96 | >20 | 1 |
| Example 97 | 0.13 | 9 |
| Example 98 | 1.12 | 6 |
| Example 99 | 0.60 | 8 |
| Example 100 | 0.31 | 9 |
| Example 101 | 4.17 | 5 |
| Example 102 | >20 | 2 |
| Example 103 | >20 | 3 |
| Example 104 | >20 | 3 |
| Example 105 | >20 | 1.7 |
| Example 106 | >20 | 2 |
| Example 107 | 0.45 | 7 |
| Example 108 | 1.21 | 7 |
| Example 109 | 8.27 | 1 |
| Example 110 | >20 | 1 |
| Example 111 | 15.49 | 5 |
| Example 112 | 5.21 | 4 |
| Example 113 | >20 | 3 |
| Example 114 | >20 | 3 |
| Example 115 | >20 | 1 |
| Example 116 | >20 | 0 |
| Example 117 | >20 | 0 |
| Example 118 | >20 | 2 |
| Example 119 | 5.50 | 3 |
| Example 120 | 3.38 | 3.3 |
| Example 121 | 1.09 | 7.5 |
| Example 122 | 1.89 | 5.1 |
| Example 123 | 3.52 | 3.3 |

The compounds of the present invention, especially Examples 1, 2, 3, 4, 5, 8, 9, 10, 17, 18, 19, 20, 21, 30, 31, 78, 97, 99 and 100, showed similar potent when compared (+)-JQ1. The compounds of the present invention were chemically stable and easily prepared when compared positive compound. The use of a compound according to any one of Examples 1-123 in the manufacture of a medicament for the treatment of a disease or a condition for which a BET bromodomain inhibitor is indicated. These data indicated the compounds of the present invention may lead to a new therapeutics to treat cancera, cellar proliferative disorders, inflammatory conditions, autoimmune disorders, sepsis, or viral infections.

The embodiments above described illustrative of several embodiments of the invention, and these illusion are specific and detailed, but not to be construed as limiting the scope of the invention. It should be noted that various modifications and improvements can be made by those skilled in the art without departing from the spirit of the invention, which are within the scope of the present invention. Accordingly, the scope of protection of the present invention should be determined by the appended claims.

The invention claimed is:

1. A 2-oxo-1,2-dihydrobenzo[cd]indole compound having a structure represented by formula I, II, III or IV:

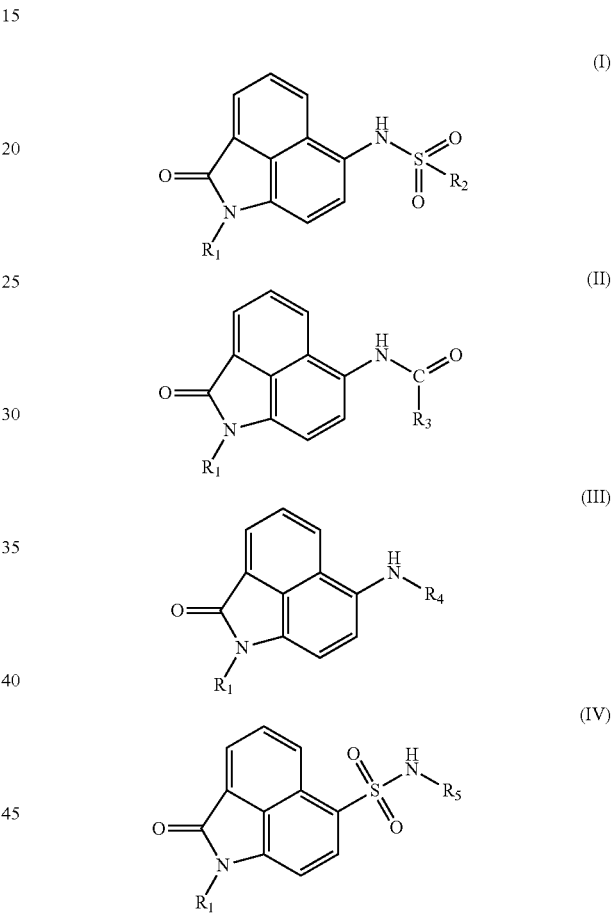

wherein, $R_1$ is selected from $C_1$-$C_4$ linear or branched alkyl, $R_2$ is selected from $C_1$-$C_7$ alkyl, $C_1$-$C_4$ alkylene-$R_6$, $C_1$-$C_4$ alkylene-$R_7$-cyclic ring, —$R_7$-cyclic ring or -cyclic ring, $R_3$ is selected from $C_1$-$C_7$ alkyl, $C_1$-$C_4$ alkylene-$R_{6'}$, $C_1$-$C_4$ alkylene-$R_7$-cyclic ring, —$R_7$-cyclic ring or -cyclic ring, $R_4$ is selected from $C_1$-$C_7$ alkyl, $C_1$-$C_4$ alkylene-$R_{6''}$, $C_1$-$C_4$ alkylene-$R_7$-cyclic ring, —$R_7$-cyclic ring or -cyclic ring, $R_5$ is selected from $C_1$-$C_7$ alkyl, $C_1$-$C_4$ alkylene-$R_{6''}$, $C_1$-$C_4$ alkylene-$R_7$-cyclic ring, —$R_7$-cyclic ring or -cyclic ring, wherein $R_6$ is selected from —$OR_8$, —$COR_8$, —$CONHR_8$, —$COOR_8$, —$S(O)_mR_8$, —$NHCOOR_8$, —$NHCOR_8$ or —$NH_2$, wherein m is 0 or 2, $R_{6'}$ is selected from —$OR_8$, —$COR_8$, —$CONHR_8$, —$COOR_8$ or —$S(O)_mR_8$, wherein m is 0 or 2, $R_{6''}$ is selected from —$OR_8$, —$COR_8$, —$CONHR_8$, —$COOR_8$, —$S(O)_mR_8$, —$NHCOOR_8$ or —$NHCOR_8$, wherein m is 0 or 2, $R_8$ is selected from hydrogen or $C_1$-$C_3$ alkyl, and $R_7$ is selected from —$COR_9$, —$COOR_9$ or —$OR_9$, wherein $R_9$ is selected from $C_1$-$C_3$ alkylene, wherein cyclic ring is selected from $C_3$-$C_{10}$ cycloalkyl, phenyl, or heterocyclic group, or a pharmaceutically acceptable salt, isomer, racemate, prodrug, cocyrstalline complex, hydrate or solvate thereof.

2. The compound according to claim 1, wherein $R_1$ is selected from methyl, ethyl, propyl, isopropyl or tert-butyl.

3. The compound according to claim 1, wherein the cyclic ring is selected from cyclopropane, cyclobutane, cyclopentane, cyclohexane, cycloheptane, phenyl, naphthyl, azetidine, oxetane, azacyclopentane, oxacyclopentane, azacyclohexane, oxacyclohexane, azacyclohexyl, imidazol-2-one ring, imidazolyl, furyl, thienyl, oxazolyl, isoxazolyl, pyrimidinyl, pyrrolyl, piperazinyl, tetrahydropyrrolyl, piperidinyl, morpholinyl, 1,3-dioxolanyl or benzo[d]thiazolyl, wherein the cyclic ring is substituted by 0, 1, 2 or 3 group(s) each independently selected from halogen, methyl, ethyl, propyl, isopropyl, tert-butyl, trifluoromethyl, cyano, nitro, amino, amide, —$COOR_{10}$, —$COR_{10}$, —$OR_{10}$, —$NHCOR_{10}$, —$NHCOR_{10}$, —$C_6H_5R_{11}$, morpholinyl, piperidinyl, tetrahydrofuranyl or pyridyl, wherein $R_{10}$ is selected from hydrogen, $C_1$-$C_4$ alkyl or phenyl, and RH is selected from $C_1$-$C_4$ alkyl, halogen, acetyl, methoxy or ethoxy.

4. The compound according to claim 1, wherein the compound is selected from a group consisting of:

N-(1-ethyl-2-oxo-1,2-dihydrobenzo[cd]indol-6-yl)butane-1-sulfonamide;

2-chloro-N-(1-ethyl-2-oxo-1,2-dihydrobenzo[cd]indol-6-yl)-4-fluorobenzenesulfonamide;

N-(1-ethyl-2-oxo-1,2-dihydrobenzo[cd]indol-6-yl)thiophene-2-sulfonamide;

5-chloro-N-(1-ethyl-2-oxo-1,2-dihydrobenzo[cd]indol-6-yl)-2-methoxybenzenesulfonamide;

N-(1-ethyl-2-oxo-1,2-dihydrobenzo[cd]indol-6-yl)cyclohexanesulfonamide;

2-(N-(1-ethyl-2-oxo-1,2-dihydrobenzo[cd]indol-6-yl)sulfamoyl)benzoate;

2-(N-(1-ethyl-2-oxo-1,2-dihydrobenzo[cd]indol-6-yl)sulfamoyl)benzoic acid;

N-(1-ethyl-2-oxo-1,2-dihydrobenzo[cd]indol-6-yl)benzenesulfonamide;

N-(1-ethyl-2-oxo-1,2-dihydrobenzo[cd]indol-6-yl)-4-fluorobenzenesulfonamide;

N-(1-ethyl-2-oxo-1,2-dihydrobenzo[cd]indol-6-yl)-3-fluorobenzenesulfonamide;

N-(1-ethyl-2-oxo-1,2-dihydrobenzo[cd]indol-6-yl)ethanesulfonamide;

N-(1-ethyl-2-oxo-1,2-dihydrobenzo[cd]indol-6-yl)-4-methoxybenzenesulfonamide;

4-cyano-N-(1-ethyl-2-oxo-1,2-dihydrobenzo[cd]indol-6-yl)benzenesulfonamide;

N-(1-ethyl-2-oxo-1,2-dihydrobenzo[cd]indol-6-yl)-4-nitrobenzenesulfonamide;

4-(tert-butyl)-N-(1-ethyl-2-oxo-1,2-dihydrobenzo[cd]indol-6-yl)benzenesulfonamide;

N-(1-ethyl-2-oxo-1,2-dihydrobenzo[cd]indol-6-yl)-4-(trifluoromethoxy)benzenesulfonamide;

3-chloro-N-(1-ethyl-2-oxo-1,2-dihydrobenzo[cd]indol-6-yl)-2-fluorobenzenesulfonamide;

N-(1-ethyl-2-oxo-1,2-dihydrobenzo[cd]indol-6-yl)-4-methylbenzenesulfonamide;

N-(1-ethyl-2-oxo-1,2-dihydrobenzo[cd]indol-6-yl)-2,4-difluorobenzenesulfonamide;

N-(1-ethyl-2-oxo-1,2-dihydrobenzo[cd]indol-6-yl)propane-1-sulfonamide;

N-(1-ethyl-2-oxo-1,2-dihydrobenzo[cd]indol-6-yl)cyclopentanesulfonamide;

N-(1-ethyl-2-oxo-1,2-dihydrobenzo[cd]indol-6-yl)-4-(trifluoromethyl)benzenesulfonamide;

N-(1-ethyl-2-oxo-1,2-dihydrobenzo[cd]indol-6-yl)-3-(methylsulfonyl)benzenesulfonamide;

N-(1-ethyl-2-oxo-1,2-dihydrobenzo[cd]indol-6-yl)naphthalene-2-sulfonamide;

4-(N-(1-ethyl-2-oxo-1,2-dihydrobenzo[cd]indol-6-yl)sulfamoyl)benzoate;

4-(N-(1-ethyl-2-oxo-1,2-dihydrobenzo[cd]indol-6-yl)sulfamoyl)benzoic acid;

3-(N-(1-ethyl-2-oxo-1,2-dihydrobenzo[cd]indol-6-yl)sulfamoyl)benzoate;

3-(N-(1-ethyl-2-oxo-1,2-dihydrobenzo[cd]indol-6-yl)sulfamoyl)benzoic acid;

N-(1-ethyl-2-oxo-1,2-dihydrobenzo[cd]indol-6-yl)-2,3-dihydrobenzo[b][1,4]dioxine-6-sulfonamide;

2-bromo-N-(1-ethyl-2-oxo-1,2-dihydrobenzo[cd]indol-6-yl)benzenesulfonamide;

5-bromo-N-(1-ethyl-2-oxo-1,2-dihydrobenzo[cd]indol-6-yl)-2-methoxybenzenesulfonamide;

2,6-dichloro-N-(1-ethyl-2-oxo-1,2-dihydrobenzo[cd]indol-6-yl)benzenesulfonamide;

N-(1-ethyl-2-oxo-1,2-dihydrobenzo[cd]indol-6-yl)-2,3-dimethoxybenzenesulfonamide;

3,5-dichloro-N-(1-ethyl-2-oxo-1,2-dihydrobenzo[cd]indol-6-yl)benzenesulfonamide;

2,3-dichloro-N-(1-ethyl-2-oxo-1,2-dihydrobenzo[cd]indol-6-yl)benzenesulfonamide;

4-((N-(1-ethyl-2-oxo-1,2-dihydrobenzo[cd]indol-6-yl)sulfamoyl)methyl)benzoate;

4-((N-(1-ethyl-2-oxo-1,2-dihydrobenzo[cd]indol-6-yl)sulfamoyl)methyl)benzoic acid;

N-(1-ethyl-2-oxo-1,2-dihydrobenzo[cd]indol-6-yl)-1-(3-fluorophenyl)methanesulfonamide;

3-((N-(1-ethyl-2-oxo-1,2-dihydrobenzo[cd]indol-6-yl)sulfamoyl)methyl)benzoate;

N-(1-ethyl-2-oxo-1,2-dihydrobenzo[cd]indol-6-yl)-1-(4-(trifluoromethyl)phenyl)methanesulfonamide;

N-(1-ethyl-2-oxo-1,2-dihydrobenzo[cd]indol-6-yl)-1-(p-tolyl)methanesulfonamide;

N-(1-ethyl-2-oxo-1,2-dihydrobenzo[cd]indol-6-yl)-1-(2-fluorophenyl)methanesulfonamide;

1-(4-chlorophenyl)-N-(1-ethyl-2-oxo-1,2-dihydrobenzo[cd]indol-6-yl)methanesulfonamide;

1-(4-cyanophenyl)-N-(1-ethyl-2-oxo-1,2-dihydrobenzo[cd]indol-6-yl)methanesulfonamide;

N-(1-ethyl-2-oxo-1,2-dihydrobenzo[cd]indol-6-yl)-1-(4-fluorophenyl)methanesulfonamide;

N-(1-ethyl-2-oxo-1,2-dihydrobenzo[cd]indol-6-yl)-4-fluorobenzamide;

2-(4-chlorophenyl)-N-(1-ethyl-2-oxo-1,2-dihydrobenzo[cd]indol-6-yl)acetamide;

2-(3,4-dimethoxyphenyl)-N-(1-ethyl-2-oxo-1,2-dihydrobenzo[cd]indol-6-yl)acetamide;

2-(2,4-dichlorophenyl)-N-(1-ethyl-2-oxo-1,2-dihydrobenzo[cd]indol-6-yl)acetamide;

N-(1-ethyl-2-oxo-1,2-dihydrobenzo[cd]indol-6-yl)-3-phenylpropanamide;
N-(1-ethyl-2-oxo-1,2-dihydrobenzo[cd]indol-6-yl)-4,4,4-trifluorobutanamide;
N-(1-ethyl-2-oxo-1,2-dihydrobenzo[cd]indol-6-yl)propionamide;
4-chloro-N-(1-ethyl-2-oxo-1,2-dihydrobenzo[cd]indol-6-yl)benzamide;
N-(1-ethyl-2-oxo-1,2-dihydrobenzo[cd]indol-6-yl)-2-(p-tolyl)acetamide;
(E)-N-(1-ethyl-2-oxo-1,2-dihydrobenzo[cd]indol-6-yl)-3-(furan-2-yl)acrylamide;
1-ethyl-6-((3-phenylpropyl)amino)benzo[cd]indol-2(1H)-one;
1-ethyl-6-((3-morpholinopropyl)amino)benzo[cd]indol-2(1H)-one;
1-ethyl-6-((4-methoxybenzyl)amino)benzo[cd]indol-2(1H)-one;
1-ethyl-64(4-methylbenzyl)amino)benzo[cd]indol-2(1H)-one;
1-ethyl-6-((4-(trifluoromethyl)benzyl)amino)benzo[cd]indol-2(1H)-one;
6-((4-chlorobenzyl)amino)-1-ethylbenzo[cd]indol-2(1H)-one;
1-ethyl-6-((4-fluorobenzyl)amino)benzo[cd]indol-2(1H)-one;
N-((1-acetylpiperidin-4-yl)methyl)-1-ethyl-2-oxo-1,2-dihydrobenzo[cd]indole-6-sulfonamide;
1-((1-ethyl-2-oxo-1,2-dihydrobenzo[cd]indole)-6-sulfonamido)cyclohexane-1-carboxamide;
1-ethyl-N-((3-isopropyl-4,5-dihydroisoxazol-5-yl)methyl)-2-oxo-1,2-dihydrobenzo[cd]indole-6-sulfonamide;
N-((3,5-dimethyl-4,5-dihydroisoxazol-5-yl)methyl)-1-ethyl-2-oxo-1,2-dihydrobenzo[cd]indole-6-sulfonamide;
N-(4-acetylphenyl)-1-ethyl-2-oxo-1,2-dihydrobenzo[cd]indole-6-sulfonamide;
N-(2-chlorobenzyl)-1-ethyl-2-oxo-1,2-dihydrobenzo[cd]indole-6-sulfonamide;
1-ethyl-N-(2-fluorobenzyl)-2-oxo-1,2-dihydrobenzo[cd]indole-6-sulfonamide;
N-(1-acetylpiperidin-4-yl)-1-ethyl-2-oxo-1,2-dihydrobenzo[cd]indole-6-sulfonamide;
Tert-butyl 4-(1-ethyl-2-oxo-1,2-dihydrobenzo[cd]indole-6-ulfonamido)piperidine-1-carboxylate;
N-cyclopentyl-1-ethyl-2-oxo-1,2-dihydrobenzo[cd]indole-6-sulfonamide;
Ethyl 1-((1-ethyl-2-oxo-1,2-dihydrobenzo[cd]indole-6-sulfonamido)methyl)cyclopentanecarboxylate;
1-((1-ethyl-2-oxo-1,2-dihydrobenzo[cd]indole-6-sulfonamido)methyl)cyclopentanecarboxylic acid;
N-(4-(1-ethyl-2-oxo-1,2-dihydrobenzo[cd]indole-6-sulfonamido)phenyl)acetamide;
2-(1-ethyl-2-oxo-1,2-dihydrobenzo[cd]indole-6-sulfonamido)benzoic acid;
1-ethyl-N-(4-fluorophenyl)-2-oxo-1,2-dihydrobenzo[cd]indole-6-sulfonamide;
N-butyl-1-ethyl-2-oxo-1,2-dihydrobenzo[cd]indole-6-sulfonamide;
N-(2-(1-ethyl-2-oxo-1,2-dihydrobenzo[cd]indole-6-sulfonamido)ethyl)acetamide;
1-ethyl-N-(2-(methylsulfonyl)ethyl)-2-oxo-1,2-dihydrobenzo[cd]indole-6-sulfonamide;
1-ethyl-2-oxo-N-(2-(2-oxoimidazolidin-1-yl)ethyl)-1,2-dihydrobenzo[cd]indole-6-sulfonamide;
Tert-butyl (4-(1-ethyl-2-oxo-1,2-dihydrobenzo[cd]indole-6-sulfonamido)butyl)carbamate;
N-(5-(1-ethyl-2-oxo-1,2-dihydrobenzo[cd]indole-6-sulfonamido)pyridin-2-yl)acetamide;
Tert-butyl 3-(1-ethyl-2-oxo-1,2-dihydrobenzo[cd]indole-6-sulfonamido)pyrrolidine-1-carboxylate;
Tert-butyl 3-(1-ethyl-2-oxo-1,2-dihydrobenzo[cd]indole-6-sulfonamido)azetidine-1-carboxylate;
N-(2-cyclohexylethyl)-1-ethyl-2-oxo-1,2-dihydrobenzo[cd]indole-6-sulfonamide;
1-ethyl-2-oxo-N-(pyrrolidin-3-yl)-1,2-dihydrobenzo[cd]indole-6-sulfonamide;
N-(azetidin-3-yl)-1-ethyl-2-oxo-1,2-dihydrobenzo[cd]indole-6-sulfonamide;
1-ethyl-N-hexyl-2-oxo-1,2-dihydrobenzo[cd]indole-6-sulfonamide;
1-ethyl-2-oxo-N-(2-(pyrrolidin-1-yl)ethyl)-1,2-dihydrobenzo[cd]indole-6-sulfonamide;
1-ethyl-2-oxo-N-(2-(tetrahydro-2H-pyran-4-yl)ethyl)-1,2-dihydrobenzo[cd]indole-6-sulfonamide;
1-ethyl-2-oxo-N-(tetrahydrofuran-3-yl)-1,2-dihydrobenzo[cd]indole-6-sulfonamide;
N-(2-(4-chlorophenoxy)ethyl)-1-ethyl-2-oxo-1,2-dihydrobenzo[cd]indole-6-sulfonamide;
N,1-diethyl-2-oxo-1,2-dihydrobenzo[cd]indole-6-sulfonamide;
1-ethyl-2-oxo-n-pentyl-1,2-dihydrobenzo[cd]indole-6-sulfonamide;
1-ethyl-N-methyl-2-oxo-1,2-dihydrobenzo[cd]indole-6-sulfonamide;
N-cyclohexyl-1-ethyl-2-oxo-1,2-dihydrobenzo[cd]indole-6-sulfonamide;
Tert-butyl 3-(1-ethyl-2-oxo-1,2-dihydrobenzo[cd]indole-6-sulfonamido)piperidine-1-carboxylate;
1-ethyl-N-isobutyl-2-oxo-1,2-dihydrobenzo[cd]indole-6-sulfonamide;
1-ethyl-2-oxo-N-propyl-1,2-dihydrobenzo[cd]indole-6-sulfonamide;
1-ethyl-N-(3-(4-methylpiperazin-1-yl)propyl)-2-oxo-1,2-dihydrobenzo[cd]indole-6-sulfonamide;
1-ethyl-2-oxo-N-(2-(piperidin-1-yl)ethyl)-1,2-dihydrobenzo[cd]indole-6-sulfonamide;
N-(4,4-diethoxybutyl)-1-ethyl-2-oxo-1,2-dihydrobenzo[cd]indole-6-sulfonamide;
Ethyl 3-(1-ethyl-2-oxo-1,2-dihydrobenzo[cd]indole-6-sulfonamido)propanoate;
1-ethyl-N-((1-ethylpyrrolidin-2-yl)methyl)-2-oxo-1,2-dihydrobenzo[cd]indole-6-sulfonamide;
1-ethyl-N-(1-methylpiperidin-4-yl)-2-oxo-1,2-dihydrobenzo[cd]indole-6-sulfonamide;
N-cycloheptyl-1-ethyl-2-oxo-1,2-dihydrobenzo[cd]indole-6-sulfonamide;
1-ethyl-2-oxo-N-(tetrahydro-2H-pyran-4-yl)-1,2-dihydrobenzo[cd]indole-6-sulfonamide;
Tert-butyl 4-(2-(1-ethyl-2-oxo-1,2-dihydrobenzo[cd]indole-6-sulfonamido)ethyl)piperazine-1-carboxylate;
N-cyclohexyl-1-methyl-2-oxo-1,2-dihydrobenzo[cd]indole-6-sulfonamide;
N-butyl-1-methyl-2-oxo-1,2-dihydrobenzo[cd]indole-6-sulfonamide;
N-cyclohexyl-2-oxo-1-propyl-1,2-dihydrobenzo[cd]indole-6-sulfonamide;
2-oxo-N,1-dipropyl-1,2-dihydrobenzo[cd]indole-6-sulfonamide;
N-butyl-2-oxo-1-propyl-1,2-dihydrobenzo[cd]indole-6-sulfonamide;

N-butyl-1-isobutyl-2-oxo-1,2-dihydrobenzo[cd]indole-6-sulfonamide;

N-cyclohexyl-1-isobutyl-2-oxo-1,2-dihydrobenzo[cd]indole-6-sulfonamide;

N-(3-acetylphenyl)-1-ethyl-2-oxo-1,2-dihydrobenzo[cd]indole-6-sulfonamide;

N-(4-chlorophenyl)-1-ethyl-2-oxo-1,2-dihydrobenzo[cd]indole-6-sulfonamide;

1-ethyl-2-oxo-N-phenyl-1,2-dihydrobenzo[cd]indole-6-sulfonamide;

N-(2-chlorophenyl)-1-ethyl-2-oxo-1,2-dihydrobenzo[cd]indole-6-sulfonamide; and

N-(3-chlorophenyl)-1-ethyl-2-oxo-1,2-dihydrobenzo[cd]indole-6-sulfonamide.

5. A pharmaceutical composition comprising a therapeutically effective amount of the compound according to claim 1 and a pharmaceutically acceptable carrier.

* * * * *